(12) United States Patent
Ito et al.

(10) Patent No.: US 11,730,054 B2
(45) Date of Patent: Aug. 15, 2023

(54) COMPOUND HAVING DIBENZOFURAN AND NAPHTHALENE STRUCTURES, AND ORGANIC ELECTROLUMINESCENT ELEMENT USING SAME

(71) Applicant: IDEMITSU KOSAN CO.,LTD., Tokyo (JP)

(72) Inventors: Hirokatsu Ito, Ichihara (JP); Tasuku Haketa, Chiba (JP); Yu Kudo, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 17/903,206

(22) Filed: Sep. 6, 2022

(65) Prior Publication Data

US 2023/0047512 A1    Feb. 16, 2023

Related U.S. Application Data

(63) Continuation of application No. 16/964,857, filed as application No. PCT/JP2019/002729 on Jan. 28, 2019.

(30) Foreign Application Priority Data

Jan. 29, 2018  (JP) ................. 2018-012793

(51) Int. Cl.
*H10K 85/60*   (2023.01)
*C07D 307/91*   (2006.01)
(Continued)

(52) U.S. Cl.
CPC ......... *H10K 85/636* (2023.02); *C07D 307/91* (2013.01); *C09K 11/06* (2013.01);
(Continued)

(58) Field of Classification Search
CPC .................................................... H10K 85/636
See application file for complete search history.

(56) References Cited

U.S. PATENT DOCUMENTS 9,087,997 B2     7/2015  Yabunouchi
10,177,333 B2 *  1/2019  Niu .................. H01L 51/5221
(Continued)

FOREIGN PATENT DOCUMENTS

CN     102596907     7/2012
CN     104903421     9/2015
(Continued)

OTHER PUBLICATIONS

International Search Report dated Feb. 26, 2019 in PCT/JP2019/002729 filed on Jan. 28, 2019, 3 pages.
(Continued)

*Primary Examiner* — Caleb E Henry
(74) *Attorney, Agent, or Firm* — Oblon, McClelland, Maier & Neustadt, L.L.P.

(57) ABSTRACT

A compound that is capable of achieving an organic EL device that has a high external quantum efficiency and a long lifetime is to be provided, and a compound represented by the following formula (1) is used (wherein in the formula, $R_{11}$ to $R_{17}$, $R_{21}$ to $R_{28}$, $R_{31}$ to $R_{38}$, $R_{41}$ to $R_{45}$, $R_{51}$ to $R_{55}$, $R_{61}$ to $R_{64}$, and $L_1$ are defined in the description).

(Continued)

US 11,730,054 B2
Page 2

| | | | |
|---|---|---|---|
| 2016/0133848 | A1 | 5/2016 | Balaganesan et al. |
| 2016/0133850 | A1 | 5/2016 | Matsuura et al. |
| 2016/0197283 | A1 | 7/2016 | Itoi et al. |
| 2016/0211457 | A1 | 7/2016 | Ito et al. |
| 2016/0351819 | A1* | 12/2016 | Kim ............... H01L 27/3206 |
| 2016/0372677 | A1 | 12/2016 | Miyake |
| 2017/0084843 | A1* | 3/2017 | Yun ................... C07D 307/91 |
| 2017/0244047 | A1 | 8/2017 | Lee et al. |
| 2017/0317290 | A1 | 11/2017 | Lee et al. |
| 2017/0331048 | A1 | 11/2017 | Cho et al. |
| 2017/0369773 | A1 | 12/2017 | Parham et al. |
| 2018/0083197 | A1* | 3/2018 | Park ................. H01L 51/0059 |
| 2018/0134951 | A1 | 5/2018 | Matsuura et al. |
| 2018/0222844 | A1 | 8/2018 | Kato et al. |
| 2018/0226585 | A1* | 8/2018 | Park ................. C07D 307/91 |
| 2019/0189946 | A1 | 6/2019 | Kim et al. |
| 2019/0028021 | A1 | 9/2019 | Yoon et al. |
| 2019/0273220 | A1 | 9/2019 | Kim et al. |
| 2019/0305254 | A1* | 10/2019 | Kim ................. H01L 51/0061 |
| 2019/0386225 | A1* | 12/2019 | Nakano ............. H10K 85/633 |
| 2020/0290985 | A1* | 9/2020 | Kudo ................. H10K 85/631 |
| 2023/0047512 | A1* | 2/2023 | Ito ..................... H10K 85/6572 |

FOREIGN PATENT DOCUMENTS

| | | |
|---|---|---|
| CN | 105541790 | 5/2016 |
| CN | 105712962 | 6/2016 |
| EP | 2 182 040 A2 | 5/2010 |
| JP | 2000-273056 A | 10/2000 |
| JP | 2008-7424 A | 1/2008 |
| JP | 2008-300503 A | 12/2008 |
| JP | 2009-10364 A | 1/2009 |
| JP | 2010-6818 A | 1/2010 |
| JP | 2010-222268 A | 10/2010 |
| JP | 2010-238924 A | 10/2010 |
| JP | 2016-509368 A | 3/2016 |
| JP | 2016-86155 A | 5/2016 |
| JP | 2016-92297 A | 5/2016 |
| JP | 2017-8023 A | 1/2017 |
| JP | 2017-22194 A | 1/2017 |
| JP | 2017-22195 A | 1/2017 |
| KR | 10-1579490 | 12/2015 |
| KR | 10-2016-0149879 A | 12/2016 |
| KR | 10-2017-0100709 A | 9/2017 |
| KR | 10-2018-0042944 A | 4/2018 |
| KR | 10-2019-0057229 A | 5/2019 |
| WO | WO 2009/145016 A1 | 12/2009 |
| WO | WO 2011/059099 A1 | 5/2011 |
| WO | WO 2014/163228 A1 | 10/2014 |
| WO | WO 2015/046982 A2 | 4/2015 |
| WO | WO 2016/009823 A1 | 1/2016 |
| WO | WO 2016/064111 A1 | 4/2016 |
| WO | WO 2016/175533 A2 | 11/2016 |
| WO | WO 2016/178544 A2 | 11/2016 |
| WO | WO 2016/190600 A1 | 12/2016 |
| WO | WO 2016/208862 A1 | 12/2016 |

OTHER PUBLICATIONS

Extended European Search Report dated May 21, 2021 in European Patent Application No. 19743869.0, 6 pages.

Japanese Office Action dated Sep. 13, 2022, in Japanese Patent Application No. 2019-567202 (with English Translation).

Chinese Office Action dated Mar. 1, 2023, in Chinese Patent Application No. 201980010449.7 (with English Translation).

* cited by examiner

17 Claims, 1 Drawing Sheet

(51) Int. Cl.
  *C09K 11/06* (2006.01)
  *H10K 50/11* (2023.01)
  *H10K 50/15* (2023.01)
  *H10K 101/10* (2023.01)

(52) U.S. Cl.
  CPC .... *H10K 85/633* (2023.02); *C09K 2211/1018* (2013.01); *H10K 50/11* (2023.02); *H10K 50/156* (2023.02); *H10K 85/626* (2023.02); *H10K 85/6574* (2023.02); *H10K 2101/10* (2023.02)

(56) References Cited

U.S. PATENT DOCUMENTS

| | | | |
|---|---|---|---|
| 10,367,163 | B2* | 7/2019 | Kim ................... H01L 51/5088 |
| 2006/0232198 | A1 | 10/2006 | Kawamura et al. |
| 2007/0205715 | A1 | 9/2007 | Saitoh et al. |
| 2009/0115320 | A1 | 5/2009 | Kawamura et al. |
| 2009/0230846 | A1 | 9/2009 | Yabe et al. |
| 2010/0001636 | A1 | 1/2010 | Yabunouchi |
| 2011/0114927 | A1 | 5/2011 | Obana et al. |
| 2012/0161119 | A1 | 6/2012 | Yabunouchi |
| 2012/0205635 | A1 | 8/2012 | Baba et al. |
| 2012/0205639 | A1 | 8/2012 | Nakasu et al. |
| 2012/0248426 | A1* | 10/2012 | Kato .................... C09B 57/00 257/E51.026 |
| 2012/0295381 | A1 | 11/2012 | Obana et al. |
| 2015/0236261 | A1 | 8/2015 | Stoessel et al. |
| 2015/0236267 | A1 | 8/2015 | Hiroaki et al. |
| 2015/0280136 | A1 | 10/2015 | Ryu et al. |
| 2016/0043325 | A1 | 2/2016 | Gorohmaru et al. |
| 2016/0118596 | A1* | 4/2016 | Sakamoto ........... H01L 51/5064 257/40 |
| 2016/0118597 | A1 | 4/2016 | Itoi et al. |

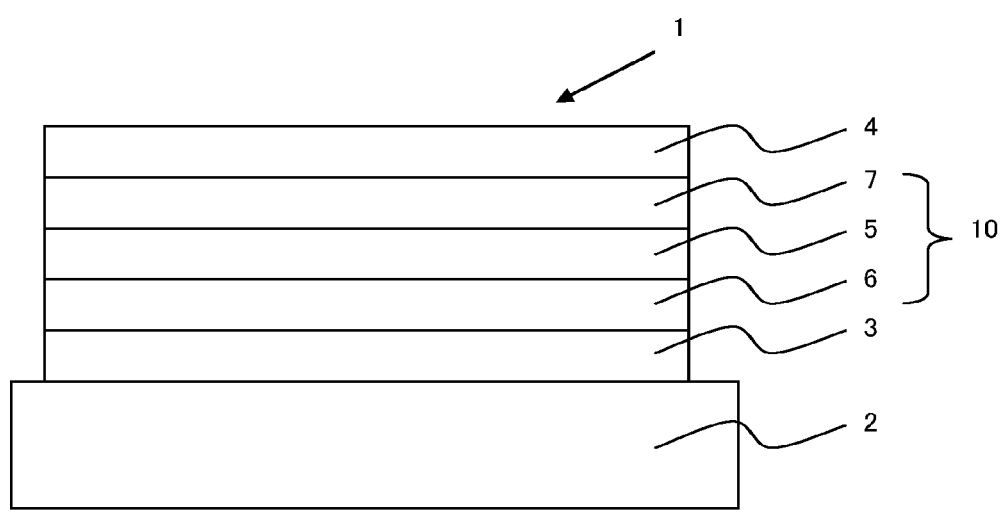

COMPOUND HAVING DIBENZOFURAN AND NAPHTHALENE STRUCTURES, AND ORGANIC ELECTROLUMINESCENT ELEMENT USING SAME

CROSS-REFERENCE TO RELATED APPLICATIONS

This application is a continuation of U.S. patent application Ser. No. 16/964,857, which is a National Stage of International Application No. PCT/JP2019/002729 filed on Jan. 28, 2019, and claims priority to Japanese Application No. 2018-012793 filed on Jan. 29, 2018, the disclosures of all of which are incorporated herein by reference in their entireties.

TECHNICAL FIELD

The present invention relates to a compound and an organic electroluminescence device using the same.

BACKGROUND ART

An organic electroluminescence (EL) device is generally constituted by an anode, a cathode, and one or more layer of an organic thin film layer held between the anode and the cathode. On application of a voltage between the electrodes, electrons are injected from the cathode and holes are injected from the anode into a light emission region, the injected electrons and holes are recombined with each other to form an excited state, and light is emitted in returning the excited state to the ground state. Accordingly, the development of a compound that is capable of efficiently transporting electrons or holes to the light emission region and capable of facilitating the recombination of electrons and holes is important for the achievement of a high efficiency organic EL device. Associated with the recent spread of smartphones, organic EL television sets, organic EL illuminations, and the like using an organic EL device, there is a demand of a compound that satisfies a high efficiency and a sufficient device lifetime simultaneously.

For example, PTLs 1 to 7 describe the compounds represented by the following formulae (C-1) to (C-8) having a dibenzofuran structure and an aryl group.

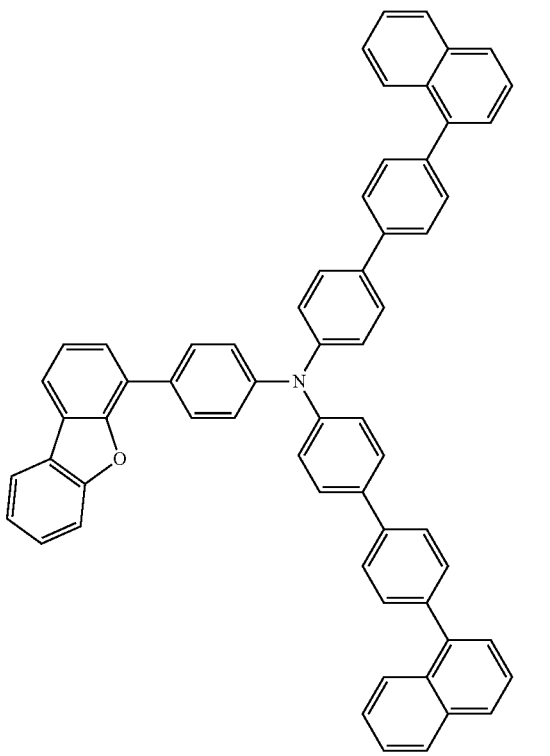

(C-1)

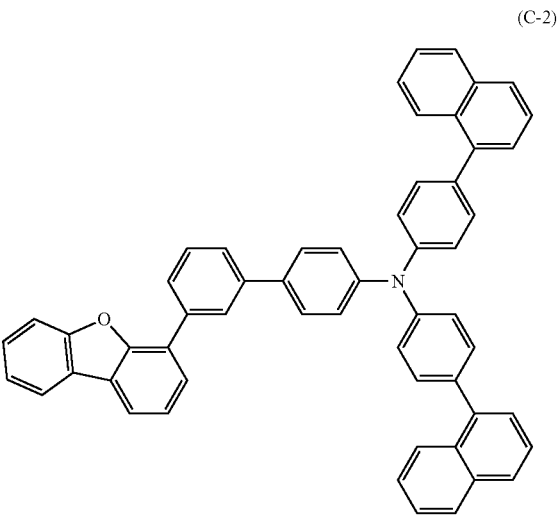

(C-2)

(C-3)
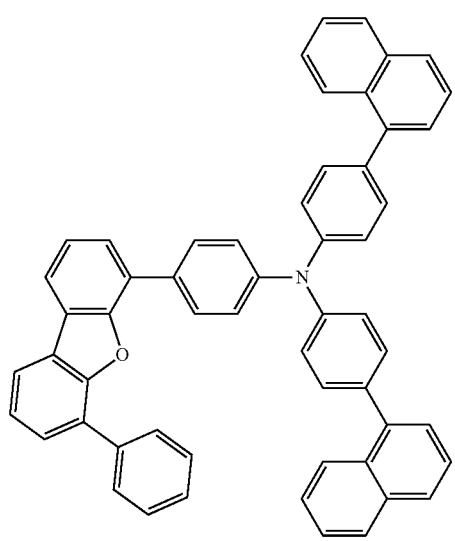
(C-4)
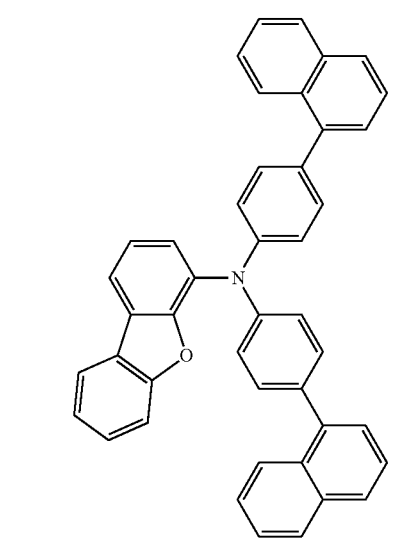
(C-5)
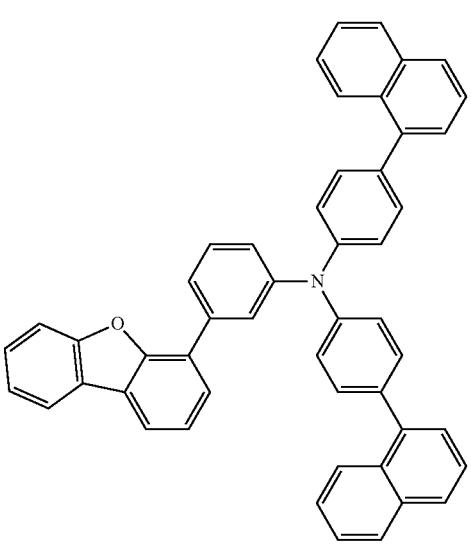
(C-6)
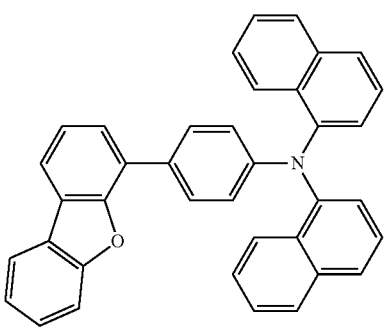
(C-7)
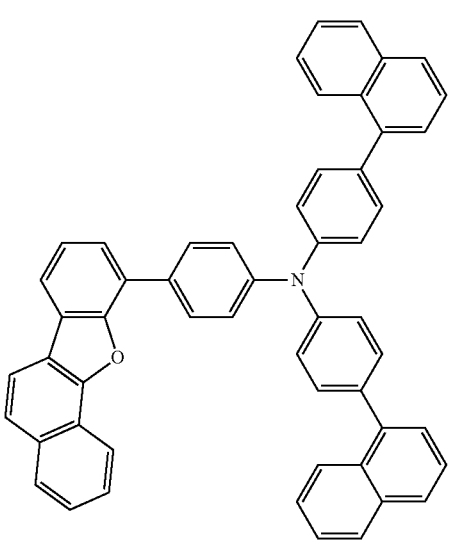
(C-8)
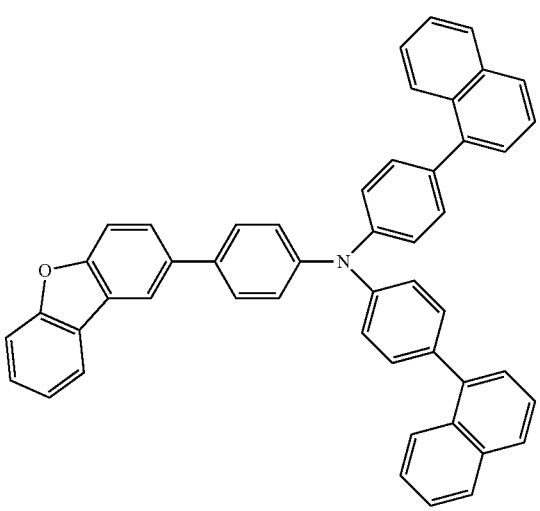
However, the compounds described in these literatures are insufficient in light emission efficiency and lifetime in the use, for example, as a hole transport layer of an organic EL device, and therefore the development of a compound that has a higher light emission efficiency and a longer lifetime has been demanded.

CITATION LIST

Patent Literatures

PTL 1: WO 2009/145016
PTL 2: Korean Patent No. 1,579,490
PTL 3: JP 2016-86155 A
PTL 4: WO 2016/064111
PTL 5: US 2016/133848 A
PTL 6: US 2016/118596 A
PTL 7: WO 2016/190600

SUMMARY OF INVENTION

Technical Problem

The present invention has been made for solving the problem, and is to provide an organic EL device that has a high external quantum efficiency and a long lifetime, and a compound that is capable of achieving the same.

Solution to Problem

As a result of the cumulative earnest investigations for achieving the object, the present inventors have found that a compound represented by the formula (1) can efficiently confine excitons in a light emitting layer while enhancing the tolerance (i.e., the suppression of the electron acceptability in the molecule), as compared to compounds represented by the formulae (C-1) to (C-8) described above. The present inventors have also found that the use of the compound having the characteristics can provide an organic EL device that has a high external quantum efficiency and a long lifetime.

One embodiment of the present invention provides a compound represented by the following formula (1) (which may be hereinafter referred to as a "compound (1)").

A compound represented by the following formula (1):

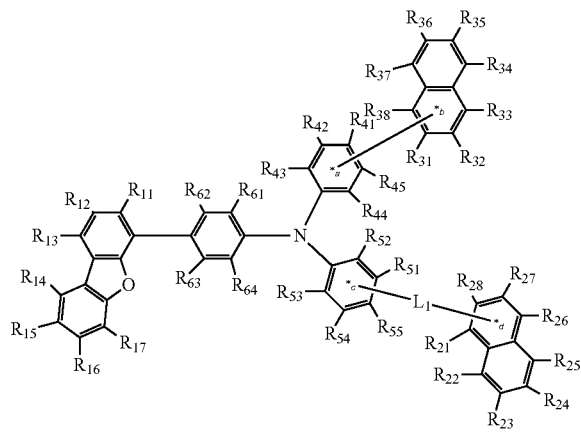

(1)

wherein in the formula (1), $R_{11}$ to $R_{17}$ and $R_{61}$ to $R_{64}$ each independently represent a hydrogen atom, an unsubstituted alkyl group having 1 to 20 carbon atoms, or an unsubstituted heteroaryl group having 3 to 50 ring carbon atoms, one of $R_{41}$ to $R_{45}$ represents a single bond bonded to *a, and the others of $R_{41}$ to $R_{45}$ than the single bond bonded to *a each independently represent a hydrogen atom, an unsubstituted alkyl group having 1 to 20 carbon atoms, or an unsubstituted heteroaryl group having 3 to 50 ring atoms, one of $R_{51}$ to $R_{55}$ represents a single bond bonded to *c, and the others of $R_{51}$ to $R_{55}$ than the single bond bonded to *c each independently represent a hydrogen atom, an unsubstituted alkyl group having 1 to 20 carbon atoms, or an unsubstituted heteroaryl group having 3 to 50 ring atoms, one of $R_{21}$ to $R_{28}$ represents a single bond bonded to *d, and the others of $R_{21}$ to $R_{28}$ than the single bond bonded to *d each independently represent a hydrogen atom, a substituted or unsubstituted alkyl group having 1 to 20 carbon atoms, a substituted or unsubstituted aryl group having 6 to 50 ring carbon atoms, or a substituted or unsubstituted heteroaryl group having 3 to 50 ring atoms, one of $R_{31}$ to $R_{38}$ represents a single bond bonded to *b, and the others of $R_{31}$ to $R_{38}$ than the single bond bonded to *b each independently represent a hydrogen atom, a substituted or unsubstituted alkyl group having 1 to 20 carbon atoms, a substituted or unsubstituted aryl group having 6 to 50 ring carbon atoms, or a substituted or unsubstituted heteroaryl group having 3 to 50 ring atoms, and $L_1$ represents a single bond, a substituted or unsubstituted phenylene group, or a substituted or unsubstituted biphenylene group, provided that in $R_{11}$ to $R_{17}$, $R_{21}$ to $R_{28}$, $R_{31}$ to $R_{38}$, $R_{44}$ to $R_{45}$, $R_{51}$ to $R_{55}$, and $R_{61}$ to $R_{64}$, substituents adjacent to each other are not bonded to each other and do not form a ring.

Another embodiment of the present invention provides a material for an organic EL device, containing the compound (1).

Still another embodiment of the present invention provides an organic electroluminescence device including an anode, a cathode, and an organic layer between the anode and the cathode, the organic layer including a light emitting layer, at least one layer of the organic layer including the compound (1).

Still another embodiment of the present invention provides an electronic equipment including the organic EL device.

Advantageous Effects of Invention

The use of the compound (1) can provide an organic EL device that has a high external quantum efficiency and a long lifetime.

BRIEF DESCRIPTION OF DRAWING

FIG. 1 is a schematic illustration showing a structure of one example of an organic electroluminescence device according to an embodiment of the present invention.

DESCRIPTION OF EMBODIMENTS

In the description herein, in the expression "XX to YY carbon atoms" in "substituted or unsubstituted ZZ group having XX to YY carbon atoms" means the number of carbon atoms in the case where the ZZ group is unsubstituted, which does not include the number of carbon atoms of the substituent in the case where the group is substituted.

In the description herein, in the expression "XX to YY atoms" in "substituted or unsubstituted ZZ group having XX to YY atoms" means the number of atoms in the case where the ZZ group is unsubstituted, which does not include the number of atoms of the substituent in the case where the group is substituted.

In the description herein, the number of ring carbon atoms means the number of carbon atoms among atoms constituting a ring itself of a compound having a structure of atoms that are bonded in the form of a ring (such as a monocyclic compound, a condensed ring compound, a crosslinked compound, a carbocyclic compound, and a heterocyclic compound). In the case where the ring is substituted by a substituent, carbon included in the substituent is not included in the number of ring carbon atoms. For the "number of ring carbon atoms" described hereinafter, the rule is similarly applied unless otherwise described. For example, a benzene ring has 6 ring carbon atoms, a naphthalene ring has 10 ring carbon atoms, a pyridinyl group has 5 ring carbon atoms, and a furanyl group has 4 ring carbon atoms. In the case where a benzene ring or a naphthalene ring is substituted, for example, by an alkyl group as a substituent, the number of carbon atoms of the alkyl group is not included in the number of ring carbon atoms. In the case where a fluorene ring has, for example, a fluorene ring bonded thereto as a substituent (including a spirofluorene ring), the number of carbon atoms of the fluorene ring as the substituent is not included in the number of ring carbon atoms.

In the description herein, the number of ring atoms means the number of atoms constituting a ring itself of a compound having a structure of atoms that are bonded in the form of a ring (such as a monocyclic ring, a condensed ring, and a ring aggregation) (such as a monocyclic compound, a condensed ring compound, a crosslinked compound, a carbocyclic compound, and a heterocyclic compound). The atom that does not constitute the ring and, in the case where the ring is substituted by a substituent, the atom included in the substituent are not included in the number of ring atoms. For the "number of ring atoms" described hereinafter, the rule is similarly applied unless otherwise described. For example, a pyridine ring has 6 ring atoms, a quinazoline ring has 10 ring atoms, and a furan ring has 5 ring atoms. The hydrogen atom and the atom constituting a substituent that each are bonded to the carbon atom of a pyridine ring or a quinazoline ring are not included in the number of ring atoms. In the case where a fluorene ring has, for example, a fluorene ring bonded thereto as a substituent (including a spirofluorene ring), the number of atoms of the fluorene ring as the substituent is not included in the number of ring atoms.

In the description herein, the "hydrogen atom" encompasses isotopes having different numbers of neutrons, i.e., protium, deuterium, and tritium.

In the description herein, the "heteroaryl group", the "heteroarylene group", and the "heterocyclic group" each are a group that has at least one heteroatom as a ring atom, and the heteroatom is preferably one or more kind selected from a nitrogen atom, an oxygen atom, a sulfur atom, a silicon atom, and a selenium atom.

In the description herein, the "substituted or unsubstituted carbazolyl group" means the following carbazolyl groups, and a substituted carbazolyl group including the following group having an arbitrary substituent.

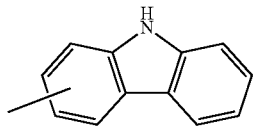

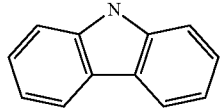

The substituted carbazolyl group may form a condensed ring by bonding arbitrary substituents to each other, and may include a heteroatom, such as a nitrogen atom, an oxygen atom, a sulfur atom, a silicon atom, and a selenium atom, and the bonding site may be any of the 1- to 9-positions. Specific examples of the substituted carbazolyl group include the following groups.

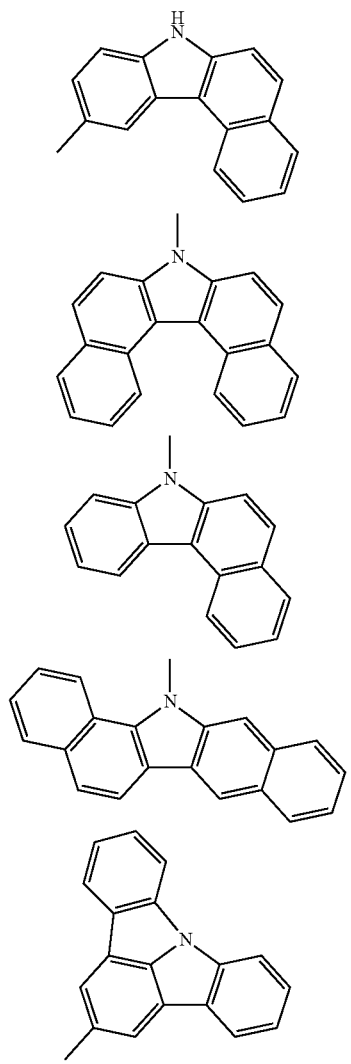

In the description herein, the "substituted or unsubstituted dibenzofuranyl group" and the "substituted or unsubstituted dibenzothiophenyl group" mean the following dibenzofuranyl group and the following dibenzothiophenyl group, and a substituted dibenzofuranyl group and a substituted dibenzothiophenyl group including the following groups having an arbitrary substituent.

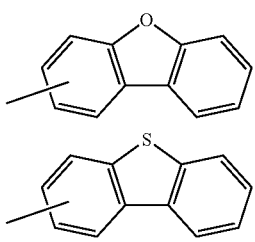

The substituted dibenzofuranyl group and the substituted dibenzothiophenyl group each may form a condensed ring by bonding arbitrary substituents to each other, and may include a heteroatom, such as a nitrogen atom, an oxygen atom, a sulfur atom, a silicon atom, and a selenium atom, and the bonding site may be any of the 1- to 8-positions. Specific examples of the substituted dibenzofuranyl group and the substituted dibenzothiophenyl group include the following groups.

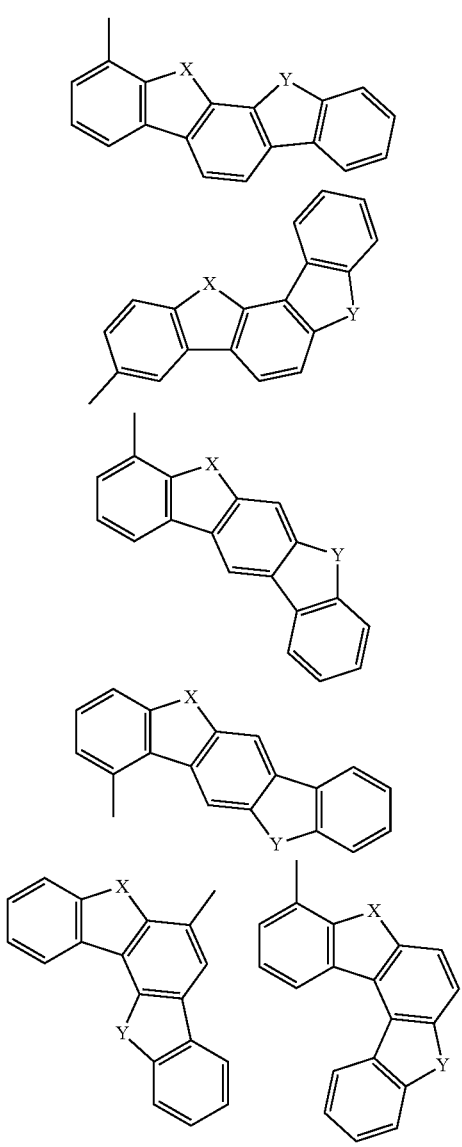

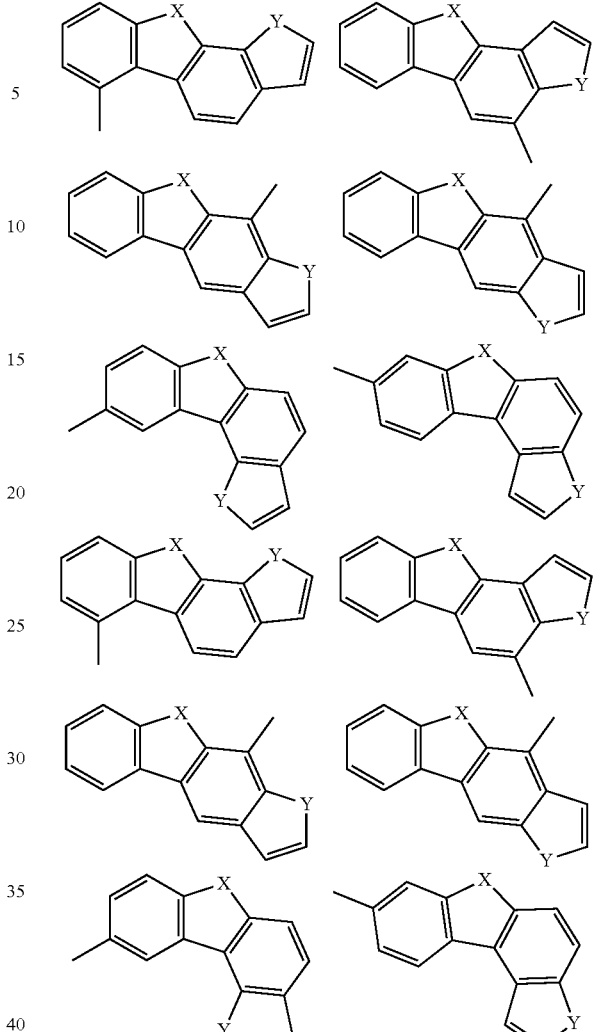

wherein X represents an oxygen atom or a sulfur atom, and Y represents an oxygen atom, a sulfur atom, NH, NR$^a$ (wherein R$^a$ represents an alkyl group or an aryl group), CH$_2$, or CR$^b_2$ (wherein R$^b$ represents an alkyl group or an aryl group.

The "substituent" and the substituent in the expression "substituted or unsubstituted" each are preferably at least one selected from the group consisting of an alkyl group having 1 to 50 (preferably 1 to 18, and more preferably 1 to 8) carbon atoms; a cycloalkyl group having 3 to 50 (preferably 3 to 10, more preferably 3 to 8, and further preferably 5 or 6) ring carbon atoms; an aryl group having 6 to 50 (preferably 6 to 25, and more preferably 6 to 18) ring carbon atoms; an aralkyl group having 7 to 51 (preferably 7 to 30, and more preferably 7 to 20) carbon atoms having an aryl group having 6 to 50 (preferably 6 to 25, and more preferably 6 to 18) ring carbon atoms; an amino group; a mono-substituted or disubstituted amino group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; an alkoxy group having an alkyl group having 1 to 50 (preferably 1 to 18, and more preferably 1 to 8) carbon atoms; an aryloxy group having an aryl group having 6 to 50 (preferably 6 to 25, and more preferably 6 to 18) ring carbon atoms; a monosubstituted, disubstituted, or trisubstituted silyl group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; a heteroaryl group having 5 to 50 (preferably 5 to 24, and more preferably 5 to 13) ring atoms; a haloalkyl group having 1 to 50 (preferably 1 to 18, and more preferably 1 to 8) carbon atoms; a halogen atom (such as a fluorine atom, a chlorine atom, a bromine atom, and an iodine atom); a cyano group; a nitro group; a sulfonyl group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; a disubstituted phosphoryl group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxy group; an alkyl-substituted or aryl-substituted carbonyl group; a carboxy group; a vinyl group; a (meth)acryloyl group; an epoxy group; and an oxetanyl group, unless otherwise defined, and each are not particularly limited thereto.

These substituents each may be further substituted by an arbitrary substituent above. These substituents may form a ring by bonding plural substituents to each other.

The expression "unsubstituted" in "substituted or unsubstituted" means that the substituent is not substituted, but has a hydrogen atom bonded thereto.

The substituent is more preferably a substituted or unsubstituted alkyl group having 1 to 50 (preferably 1 to 18, and more preferably 1 to 8) carbon atoms; a substituted or unsubstituted cycloalkyl group having 3 to 50 (preferably 3 to 10, more preferably 3 to 8, and further preferably 5 or 6) ring carbon atoms; a substituted or unsubstituted aryl group having 6 to 50 (preferably 6 to 25, and more preferably 6 to 18) ring carbon atoms; a monosubstituted or disubstituted amino group having a substituent selected from a substituted or unsubstituted alkyl group having 1 to 50 (preferably 1 to 18, and more preferably 1 to 8) carbon atoms and a substituted or unsubstituted aryl group having 6 to 50 (preferably 6 to 25, and more preferably 6 to 18) ring carbon atoms; a substituted or unsubstituted heteroaryl group having 5 to 50 (preferably 5 to 24, and more preferably 5 to 13) ring atoms, a halogen atom, or a cyano group.

Examples of the alkyl group having 1 to 50 carbon atoms include a methyl group, an ethyl group, a n-propyl group, an isopropyl group, a n-butyl group, an isobutyl group, a s-butyl group, a t-butyl group, pentyl groups (including isomeric groups), hexyl groups (including isomeric groups), heptyl groups (including isomeric groups), octyl groups (including isomeric groups), nonyl groups (including isomeric groups), decyl groups (including isomeric groups), undecyl groups (including isomeric groups), and dodecyl groups (including isomeric groups). Among these, a methyl group, an ethyl group, a n-propyl group, an isopropyl group, a n-butyl group, an isobutyl group, a s-butyl group, a t-butyl group, and pentyl groups (including isomeric groups) are preferred, a methyl group, an ethyl group, a n-propyl group, an isopropyl group, a n-butyl group, an isobutyl group, a s-butyl group, and a t-butyl group are more preferred, and a methyl group, an ethyl group, an isopropyl group, and a t-butyl group are particularly preferred.

Examples of the cycloalkyl group having 3 to 50 ring carbon atoms include a cyclopropyl group, a cyclobutyl group, a cyclopentyl group, a cyclohexyl group, a cycloheptyl group, a cyclooctyl group, and an adamantyl group. Among these, a cyclopentyl group and a cyclohexyl group are preferred.

Examples of the aryl group having 6 to 50 ring carbon atoms include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group. Among these, a phenyl group, a biphenylyl group, a terphenylyl group, a naphthyl group, an anthryl group, a pyrenyl group, and a fluoranthenyl group are preferred, a phenyl group, a biphenylyl group, and a terphenylyl group are more preferred, and a phenyl group is further preferred.

Specific examples of the aralkyl group having 7 to 51 carbon atoms having an aryl group having 6 to 50 ring carbon atoms include groups having the aryl group moiety that is the specific examples of the aryl group having 6 to 50 ring carbon atoms, and also include groups having the alkyl group moiety that is the specific examples of the alkyl group having 1 to 50 carbon atoms. Preferred examples of the aralkyl group having 7 to 51 carbon atoms include groups having the aryl group moiety that is the preferred examples of the aryl group having 6 to 50 ring carbon atoms, and also include groups having the alkyl group moiety that is the preferred examples of the alkyl group having 1 to 50 carbon atoms. More preferred specific examples and further preferred specific examples thereof are also the same.

Specific examples of the monosubstituted or disubstituted amino group having a substituent selected from an alkyl group having 1 to 50 carbon atoms and an aryl group having 6 to 50 ring carbon atoms include groups having the aryl group moiety that is the specific examples of the aryl group having 6 to 50 ring carbon atoms, and also include groups having the alkyl group moiety that is the specific examples of the alkyl group having 1 to 50 carbon atoms. Preferred examples of the monosubstituted or disubstituted amino group having a substituent selected from an alkyl group having 1 to 50 carbon atoms and an aryl group having 6 to 50 ring carbon atoms include groups having the aryl group moiety that is the preferred examples of the aryl group having 6 to 50 ring carbon atoms, and also include groups having the alkyl group moiety that is the preferred examples of the alkyl group having 1 to 50 carbon atoms. More preferred specific examples, further preferred specific examples, and particularly preferred examples thereof are also the same.

Specific examples of the alkoxy group having an alkyl group having 1 to 50 carbon atoms include groups having the alkyl group moiety that is the specific examples of the alkyl group having 1 to 50 ring carbon atoms. Preferred examples of the alkoxy group having an alkyl group having 1 to 50 carbon atoms include groups having an alkyl group moiety that is the preferred examples of the alkyl group having 1 to 50 ring carbon atoms. More preferred specific examples, further preferred specific examples, and particularly preferred examples thereof are also the same.

Specific examples of the aryloxy group having an aryl group having 6 to 50 ring carbon atoms include groups having the aryl group moiety that is the specific examples of the aryl group having 6 to 50 ring carbon atoms. Preferred examples of the aryloxy group having an aryl group having 6 to 50 ring carbon atoms include groups having the aryl group moiety that is the preferred examples of the aryl group having 6 to 50 ring carbon atoms. More preferred specific examples and further preferred specific examples thereof are also the same.

Examples of the monosubstituted, disubstituted, or trisubstituted silyl group having a substituent selected from an alkyl group having 1 to 50 carbon atoms and an aryl group having 6 to 50 ring carbon atoms include a monoalkylsilyl group, a dialkylsilyl group, and a trialkylsilyl group; a monoarylsilyl group, a diarylsilyl group, and a triarylsilyl group; and a monoalkyldiarylsilyl group and dialkylmonoarylsilyl group, and also include examples of these groups having the alkyl group moiety and the aryl group moiety that are specific examples of the aryl group having 6 to 50 ring carbon atoms and the alkyl group having 1 to 50 carbon atoms respectively. Preferred examples of the monosubstituted, disubstituted, or trisubstituted silyl group having a substituent selected from an alkyl group having 1 to 50 carbon atoms and an aryl group having 6 to 50 ring carbon atoms include a monoalkylsilyl group, a dialkylsilyl group, and a trialkylsilyl group; a monoarylsilyl group, a diarylsilyl group, and a triarylsilyl group; and a monoalkyldiarylsilyl group and dialkylmonoarylsilyl group having the alkyl group moiety and the aryl group moiety that are preferred examples of the aryl group having 6 to 50 ring carbon atoms and the alkyl group having 1 to 50 carbon atoms respectively. More preferred specific examples, further preferred specific examples, and particularly preferred examples thereof are also the same.

Examples of the heteroaryl group having 5 to 50 include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a 9-phenylcarbazolyl group, a phenanthridinyl group, an acridinyl group, a phenanthrolinyl group, a phenazinyl group, a phenothiazinyl group, a phenoxazinyl group, and a xanthenyl group. Among these, a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a 9-phenylcarbazolyl group, a phenanthrolinyl group, and a quinazolinyl group are preferred.

Examples of the halogen atom include a fluorine atom, a chlorine atom, a bromine atom, and an iodine atom.

Specific examples of the haloalkyl group having 1 to 50 carbon atoms include examples of the alkyl group having 1 to 50 carbon atoms having the hydrogen atom that is substituted by the halogen atom, and preferred examples of the alkyl group in this case include the preferred examples of the alkyl group having 1 to 50 carbon atoms. More preferred specific examples, further preferred specific examples, and particularly preferred examples thereof are also the same.

Examples of the sulfonyl group having a substituent selected from an alkyl group having 1 to 50 carbon atoms and an aryl group having 6 to 50 ring carbon atoms, the disubstituted phosphoryl group having a substituent selected from an alkyl group having 1 to 50 carbon atoms and an aryl group having 6 to 50 ring carbon atoms, the alkylsulfonyloxy group, the arylsulfonyloxy group, the alkylcarbonyloxy group, the arylcarbonyloxy group, and the alkyl-substituted or aryl-substituted carbonyl group include these groups having the aryl group moiety and the alkyl group moiety that are the specific examples of the aryl group having 6 to 50 ring carbon atoms and the alkyl group having 1 to 50 carbon atoms respectively. Preferred examples of the sulfonyl group having a substituent selected from an alkyl group having 1 to 50 carbon atoms and an aryl group having 6 to 50 ring carbon atoms, the disubstituted phosphoryl group having a substituent selected from an alkyl group having 1 to 50 carbon atoms and an aryl group having 6 to 50 ring carbon atoms, the alkylsulfonyloxy group, the arylsulfonyloxy group, the alkylcarbonyloxy group, the arylcarbonyloxy group, and the alkyl-substituted or aryl-substituted carbonyl group include these groups having the aryl group moiety and the alkyl group moiety that are the preferred examples of the aryl group having 6 to 50 ring carbon atoms and the alkyl group having 1 to 50 carbon atoms respectively. More preferred specific examples, further preferred specific examples, and particularly preferred examples thereof are also the same.

In the description herein, the preferred embodiments (such as compounds, various groups, and numerical ranges) may be arbitrarily combined with all the embodiments (such as compounds, various groups, and numerical ranges), and combinations of the preferred embodiments (including the more preferred embodiments, the further preferred embodiments, and the particularly preferred embodiments) are more preferred.

The compound (1) is represented by the following formula (1).

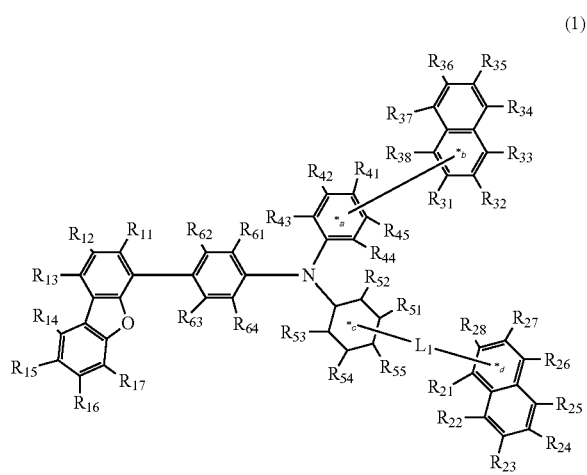

In the formula (1), $R_{11}$ to $R_{17}$ and $R_{31}$ to $R_{64}$ each independently represent a hydrogen atom, an unsubstituted alkyl group having 1 to 20, preferably 1 to 5, and more preferably 1 to 4, carbon atoms, or an unsubstituted heteroaryl group having 3 to 50, preferably 3 to 24, and more preferably 3 to 12, ring carbon atoms.

One of $R_{41}$ to $R_{45}$ represents a single bond bonded to *a, and the others of $R_{41}$ to $R_{45}$ than the single bond bonded to *a each independently represent a hydrogen atom, an unsubstituted alkyl group having 1 to 20, preferably 1 to 5, and more preferably 1 to 4, carbon atoms, or an unsubstituted heteroaryl group having 3 to 50, preferably 3 to 24, and more preferably 3 to 12, ring atoms.

One of $R_{51}$ to $R_{55}$ represents a single bond bonded to *c, and the others of $R_{51}$ to $R_{55}$ than the single bond bonded to *c each independently represent a hydrogen atom, an unsubstituted alkyl group having 1 to 20, preferably 1 to 5, and more preferably 1 to 4, carbon atoms, or an unsubstituted heteroaryl group having 3 to 50, preferably 3 to 24, and more preferably 3 to 12, ring atoms.

One of $R_{21}$ to $R_{28}$ represents a single bond bonded to *d, and the others of $R_{21}$ to $R_{28}$ than the single bond bonded to *d each independently represent a hydrogen atom, a substituted or unsubstituted alkyl group having 1 to 20, preferably 1 to 5, and more preferably 1 to 4, carbon atoms, a substituted or unsubstituted aryl group having 6 to 50, preferably 6 to 24, and more preferably 6 to 12, ring carbon atoms, or a substituted or unsubstituted heteroaryl group having 3 to 50, preferably 3 to 24, and more preferably 3 to 12, ring atoms.

One of $R_{31}$ to $R_{38}$ represents a single bond bonded to *b, and the others of $R_{31}$ to $R_{38}$ than the single bond bonded to *b each independently represent a hydrogen atom, a substituted or unsubstituted alkyl group having 1 to 20, preferably 1 to 5, and more preferably 1 to 4, carbon atoms, a substituted or unsubstituted aryl group having 6 to 50, preferably 6 to 24, and more preferably 6 to 12, ring carbon atoms, or a substituted or unsubstituted heteroaryl group having 3 to 50, preferably 3 to 24, and more preferably 3 to 12, ring atoms.

$L_1$ represents a single bond, a substituted or unsubstituted phenylene group, or a substituted or unsubstituted biphenylene group.

In $R_{11}$ to $R_{17}$, $R_{21}$ to $R_{28}$, $R_{31}$ to $R_{38}$, $R_{41}$ to $R_{45}$, $R_{51}$ to $R_{55}$, and $R_{61}$ to $R_{64}$, substituents adjacent to each other are not bonded to each other and do not form a ring.

In the formula (1), it is preferred that $R_{11}$ to $R_{17}$ are all hydrogen atoms, and it is more preferred that $R_{11}$ to $R_{17}$, $R_{41}$ to $R_{45}$ other than the single bond bonded to *a, $R_{51}$ to $R_{55}$ other than the single bond bonded to *c, and $R_{61}$ to $R_{64}$ are all hydrogen atoms.

In the formula (1), it is preferred that $R_{21}$ to $R_{28}$ other than the single bond bonded to *d and $R_{31}$ to $R_{38}$ other than the single bond bonded to *b are all hydrogen atoms.

In the formula (1), it is particularly preferred that $R_{11}$ to $R_{17}$, $R_{61}$ to $R_{64}$, $R_{41}$ to $R_{45}$, $R_{51}$ to $R_{55}$, $R_{21}$ to $R_{28}$, and $R_{31}$ to $R_{38}$ are all hydrogen atoms.

In the formula (1), $L_1$ preferably represents a single bond, an unsubstituted phenylene group, or an unsubstituted biphenylene group, more preferably a single bond or an unsubstituted phenylene group, and further preferably a single bond.

Examples of the unsubstituted alkyl group having 1 to 20 carbon atoms in $R_{11}$ to $R_{17}$, $R_{41}$ to $R_{45}$ other than the single bond bonded to *a, $R_{51}$ to $R_{55}$ other than the single bond bonded to *c, and $R_{61}$ to $R_{64}$, and the substituted or unsubstituted alkyl group having 1 to 20 carbon atoms in $R_{21}$ to $R_{28}$ other than the single bond bonded to *d and $R_{31}$ to $R_{38}$ other than the single bond bonded to *b include a methyl group, an ethyl group, a n-propyl group, an isopropyl group, a n-butyl group, an isobutyl group, a s-butyl group, a t-butyl group, pentyl groups (including isomeric groups), hexyl groups (including isomeric groups), heptyl groups (including isomeric groups), octyl groups (including isomeric groups), nonyl groups (including isomeric groups), decyl groups (including isomeric groups), undecyl groups (including isomeric groups), and dodecyl groups (including isomeric groups); a methyl group, an ethyl group, a n-propyl group, an isopropyl group, a n-butyl group, an isobutyl group, a s-butyl group, a t-butyl group, and pentyl groups (including isomeric groups) are preferred; a methyl group, an ethyl group, a n-propyl group, an isopropyl group, a n-butyl group, an isobutyl group, a s-butyl group, and a t-butyl group are more preferred; and a methyl group and a t-butyl group are further preferred.

The heteroaryl group having 3 to 50 ring atoms includes at least one, and preferably 1 to 3, the same or different heteroatoms (such as a nitrogen atom, a sulfur atom, and an oxygen atom).

Examples of the unsubstituted heteroaryl group having 3 to 50 ring atoms in $R_{11}$ to $R_{17}$, $R_{41}$ to $R_{45}$ other than the single bond bonded to *a, $R_{51}$ to $R_{55}$ other than the single bond bonded to *c, and $R_{61}$ to $R_{64}$, and the substituted or unsubstituted heteroaryl group having 3 to 50 ring atoms in $R_{21}$ to $R_{28}$ other than the single bond bonded to *d and $R_{31}$ to $R_{38}$ other than the single bond bonded to *b include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, and a xanthenyl group; a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, a dibenzothiophenyl group, and a carbazolyl group are preferred; and a benzofuranyl group, a benzothiophenyl group, a dibenzofuranyl group, a dibenzothiophenyl group, and a carbazolyl group are more preferred.

Examples of the substituted or unsubstituted aryl group having 6 to 50 ring carbon atoms in $R_{21}$ to $R_{28}$ other than the single bond bonded to *d and $R_{31}$ to $R_{38}$ other than the single bond bonded to *b include a phenyl group, a naphthylphenyl group, a biphenylyl group, a terphenylyl group, a biphenylenyl group, a naphthyl group, a phenylnaphthyl group, an acenaphthyl group, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group; a phenyl group, a naphthylphenyl group, a biphenylyl group, a terphenylyl group, a naphthyl group, and a 9,9-dimethylfluorenyl group are preferred; a phenyl group, a biphenylyl group, a naphthyl group, and a 9,9-dimethylfluorenyl group are more preferred; and a phenyl group is further preferred.

In one embodiment of the present invention, the compound (1) is preferably represented by the following formula (2-1) or (2-2).

(2-1)

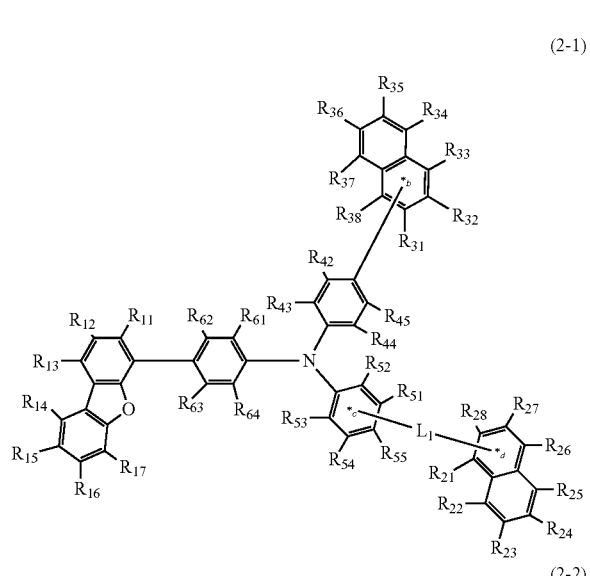

(2-2)

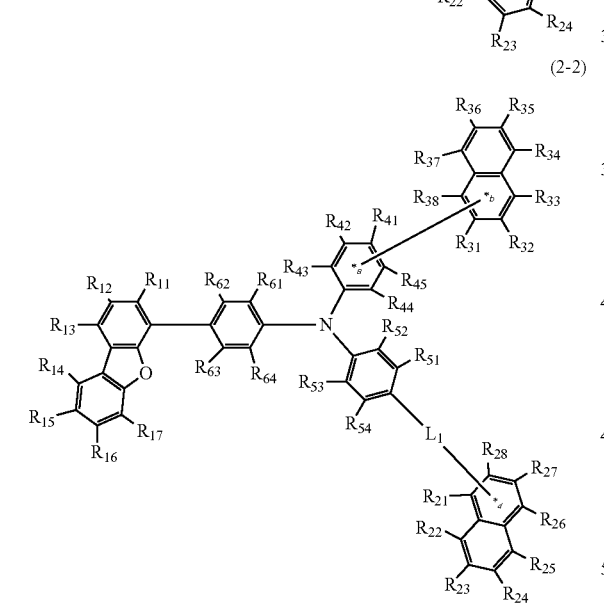

wherein in the formulae (2-1) and (2-2), $R_{11}$ to $R_{17}$, $R_{21}$ to $R_{28}$, $R_{31}$ to $R_{38}$, $R_{41}$ to $R_{45}$, $R_{51}$ to $R_{55}$, $R_{61}$ to $R_{64}$, and $L_1$ are the same as above.

In the formulae (2-1) and (2-2), specific examples, preferred number of carbon atoms and preferred number of atoms, and the like of the groups represented by $R_{11}$ to $R_{17}$, $R_{21}$ to $R_{28}$, $R_{31}$ to $R_{38}$, $R_{41}$ to $R_{45}$, $R_{51}$ to $R_{55}$, $R_{61}$ to $R_{64}$, and $L_1$ are the same as above. In $R_{11}$ to $R_{17}$, $R_{21}$ to $R_{28}$, $R_{31}$ to $R_{38}$, $R_{41}$ to $R_{45}$, $R_{51}$ to $R_{55}$, and $R_{61}$ to $R_{64}$, substituents adjacent to each other are not bonded to each other and do not form a ring.

In one embodiment of the present invention, the compound (1) is more preferably represented by the following formula (3-1).

(3-1)

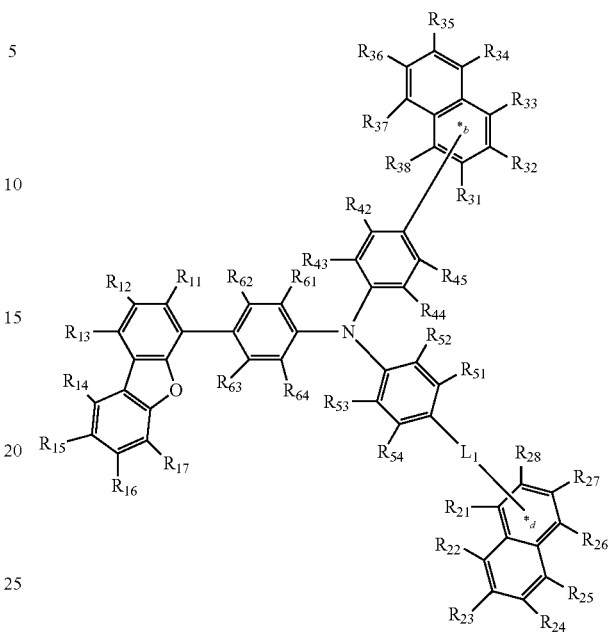

wherein in the formula (3-1), $R_{11}$ to $R_{17}$, $R_{21}$ to $R_{28}$, $R_{31}$ to $R_{38}$, $R_{42}$ to $R_{45}$, $R_{51}$ to $R_{54}$, $R_{61}$ to $R_{64}$, and $L_1$ are the same as above.

In the formula (3-1), specific examples, preferred number of carbon atoms and preferred number of atoms, and the like of the groups represented by $R_{11}$ to $R_{17}$, $R_{21}$ to $R_{28}$, $R_{31}$ to $R_{38}$, $R_{42}$ to $R_{45}$, $R_{51}$ to $R_{54}$, $R_{61}$ to $R_{64}$, and $L_1$ are the same as above. In $R_{11}$ to $R_{17}$, $R_{21}$ to $R_{28}$, $R_{31}$ to $R_{38}$, $R_{42}$ to $R_{45}$, $R_{51}$ to $R_{54}$, and $R_{61}$ to $R_{64}$, substituents adjacent to each other are not bonded to each other and do not form a ring.

In one embodiment of the present invention, the compound (1) is more preferably represented by any of the following formulae (3-2) to (3-9).

(3-2)

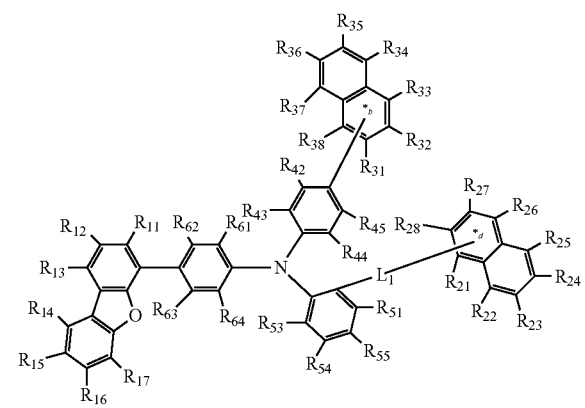

(3-3)

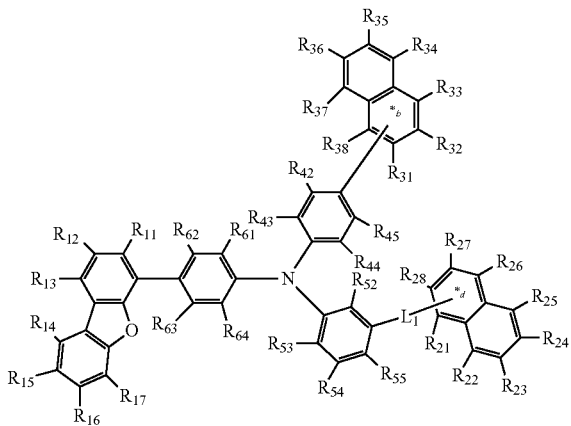

(3-5)

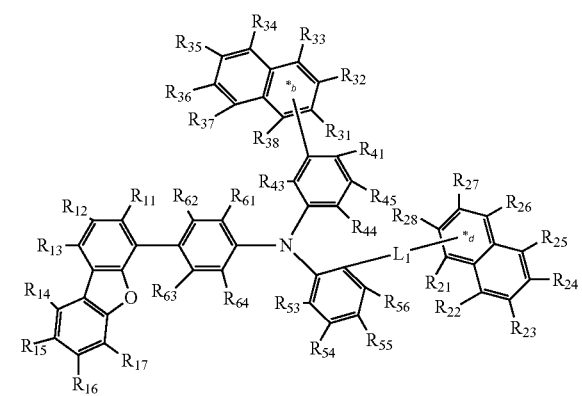

wherein in the formulae (3-2) and (3-3), $R_{11}$ to $R_{17}$, $R_{21}$ to $R_{28}$, $R_{31}$ to $R_{38}$, $R_{42}$ to $R_{45}$, $R_{51}$ to $R_{55}$, $R_{61}$ to $R_{64}$, and $L_1$ are the same as above.

In the formulae (3-2) and (3-3), specific examples, preferred number of carbon atoms and preferred number of atoms, and the like of the groups represented by $R_{11}$ to $R_{17}$, $R_{21}$ to $R_{28}$, $R_{31}$ to $R_{38}$, $R_{42}$ to $R_{45}$, $R_{51}$ to $R_{55}$, $R_{61}$ to $R_{64}$, and $L_1$ are the same as above. In $R_{11}$ to $R_{17}$, $R_{21}$ to $R_{28}$, $R_{31}$ to $R_{38}$, $R_{42}$ to $R_{45}$, $R_{51}$ to $R_{55}$, and $R_{61}$ to $R_{64}$, substituents adjacent to each other are not bonded to each other and do not form a ring.

(3-4)

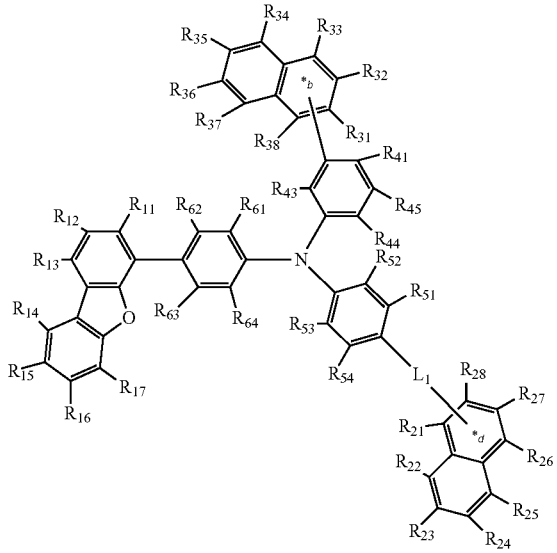

(3-6)

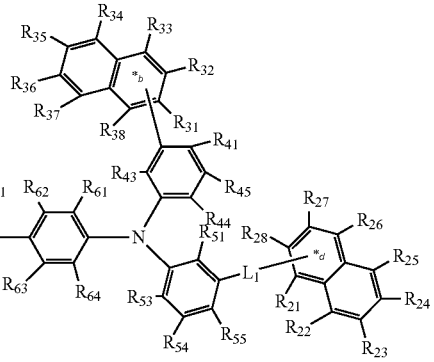

wherein in the formulae (3-4), (3-5), and (3-6), $R_{11}$ to $R_{17}$, $R_{21}$ to $R_{28}$, $R_{31}$ to $R_{38}$, $R_{41}$, $R_{43}$ to $R_{45}$, $R_{53}$ to $R_{56}$, $R_{61}$ to $R_{64}$, and $L_1$ are the same as above.

In the formulae (3-4), (3-5), and (3-6), specific examples, preferred number of carbon atoms and preferred number of atoms, and the like of the groups represented by $R_{11}$ to $R_{17}$, $R_{21}$ to $R_{28}$, $R_{31}$ to $R_{38}$, $R_{41}$, $R_{43}$ to $R_{45}$, $R_{53}$ to $R_{56}$, $R_{61}$ to $R_{64}$, and $L_1$ are the same as above. In $R_{11}$ to $R_{17}$, $R_{21}$ to $R_{28}$, $R_{31}$ to $R_{38}$, $R_{41}$, $R_{43}$ to $R_{45}$, $R_{53}$ to $R_{56}$, and $R_{61}$ to $R_{64}$, substituents adjacent to each other are not bonded to each other and do not form a ring.

(3-7)

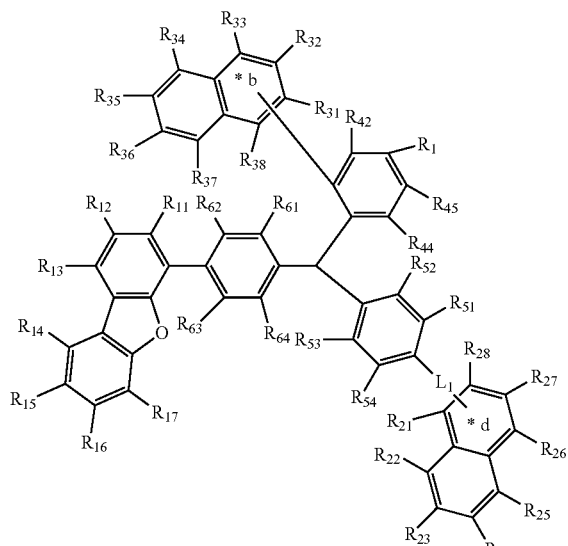

(3-8)

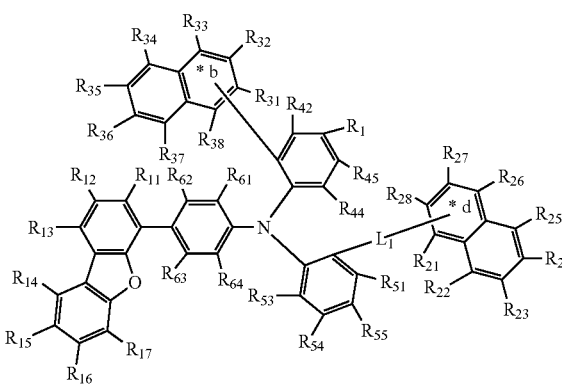

(3-9)

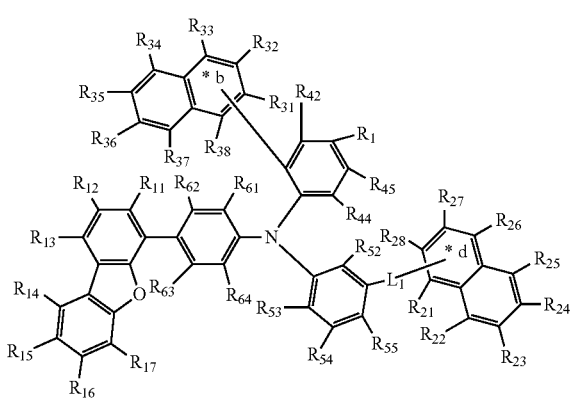

wherein in the formulae (3-7), (3-8), and (3-9), $R_{11}$ to $R_{17}$, $R_{21}$ to $R_{28}$, $R_{31}$ to $R_{38}$, $R_{41}$, $R_{42}$, $R_{44}$, $R_{45}$, $R_{51}$ to $R_{55}$, $R_{61}$ to $R_{64}$, and $L_1$ are the same as above.

In the formulae (3-7), (3-8), and (3-9), specific examples, preferred number of carbon atoms and preferred number of atoms, and the like of the groups represented by $R_{11}$ to $R_{17}$, $R_{21}$ to $R_{28}$, $R_{31}$ to $R_{38}$, $R_{41}$, $R_{42}$, $R_{44}$, $R_{45}$, $R_{51}$ to $R_{55}$, $R_{61}$ to $R_{64}$, and $L_1$ are the same as above. In $R_{11}$ to $R_{17}$, $R_{21}$ to $R_{28}$, $R_{31}$ to $R_{38}$, $R_{41}$, $R_{42}$, $R_{44}$, $R_{45}$, $R_{51}$ to $R_{55}$, $R_{61}$ to $R_{64}$, substituents adjacent to each other are not bonded to each other and do not form a ring.

In one embodiment of the present invention, the compound (1) is further preferably represented by any of the following formulae (3-1-1) to (3-1-4).

(3-1-1)

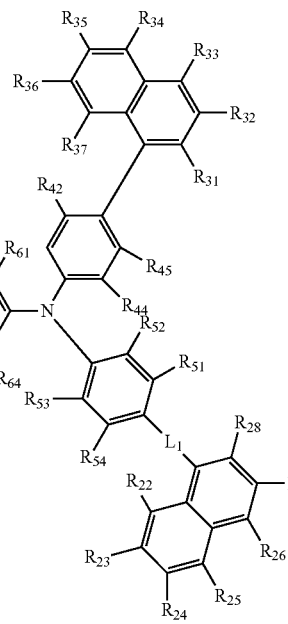

(3-1-2)

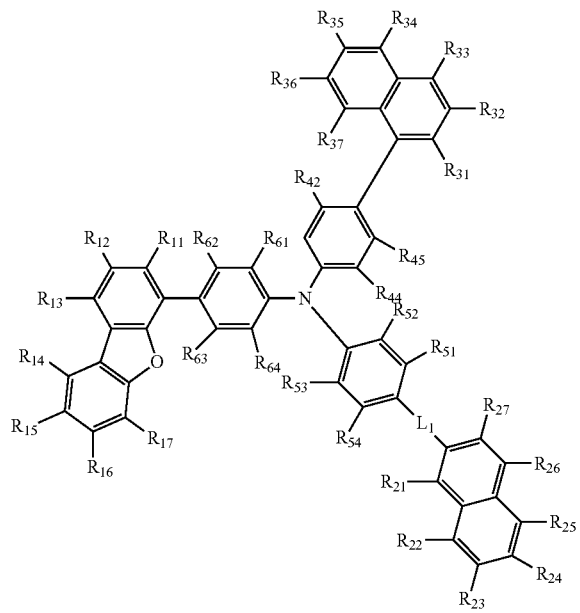

-continued (3-1-3)

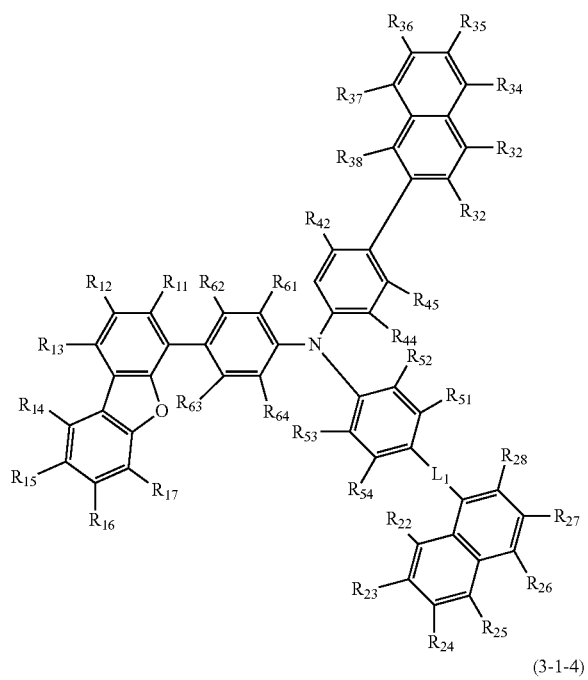

(3-1-4)

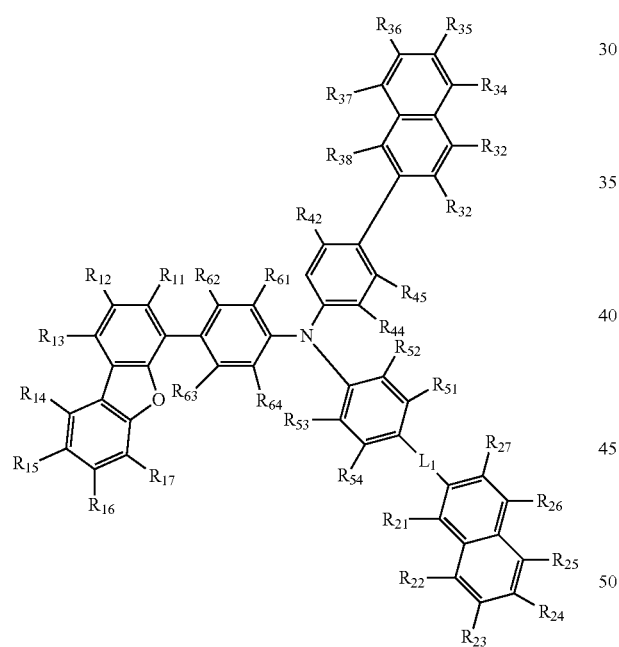

wherein in the formulae (3-1-1), (3-1-2), (3-1-3), and (3-1-4), $R_{11}$ to $R_{17}$, $R_{21}$ to $R_{28}$, $R_{31}$ to $R_{38}$, $R_{42}$ to $R_{45}$, $R_{51}$ to $R_{54}$, $R_{61}$ to $R_{64}$, and $L_1$ are the same as above.

In the formulae (3-1-1), (3-1-2), (3-1-3), and (3-1-4), preferred number of carbon atoms and preferred number of atoms, and the like of the groups represented by $R_{11}$ to $R_{17}$, $R_{21}$ to $R_{28}$, $R_{31}$ to $R_{38}$, $R_{42}$ to $R_{45}$, $R_{51}$ to $R_{54}$, $R_{61}$ to $R_{64}$, and $L_1$ are the same as above. In $R_{11}$ to $R_{17}$, $R_{21}$ to $R_{28}$, $R_{31}$ to $R_{38}$, $R_{42}$ to $R_{45}$, $R_{51}$ to $R_{54}$, and $R_{61}$ to $R_{64}$, substituents adjacent to each other are not bonded to each other and do not form a ring.

In $R_{11}$ to $R_{17}$, $R_{21}$ to $R_{28}$, $R_{31}$ to $R_{38}$, $R_{41}$ to $R_{45}$, $R_{51}$ to $R_{55}$, and $R_{61}$ to $R_{64}$, substituents adjacent to each other are not bonded to each other.

Accordingly, in $R_{11}$ to $R_{17}$, $R_{21}$ to $R_{28}$, $R_{31}$ to $R_{38}$, $R_{41}$ to $R_{45}$, $R_{51}$ to $R_{55}$, and $R_{61}$ to $R_{64}$, substituents adjacent to each other do not form a ring.

Specific examples of the compound according to the present invention are shown below, but the compound is not particularly limited thereto.

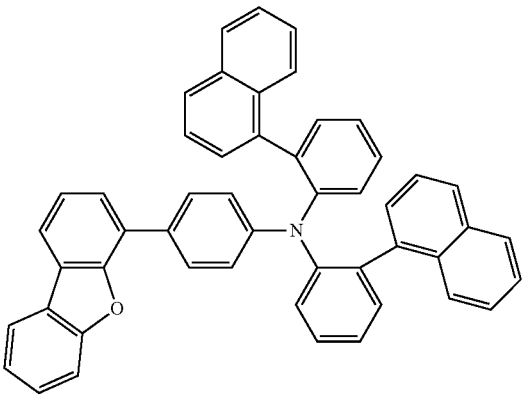

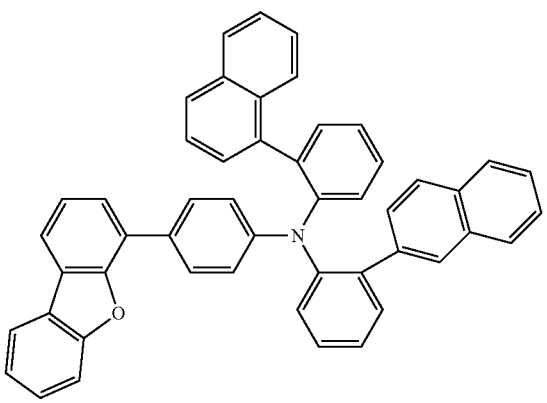

-continued
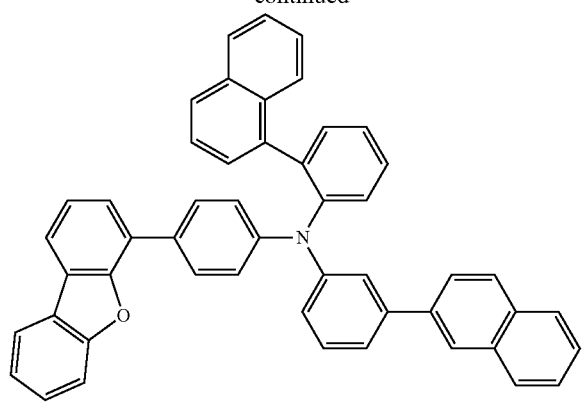
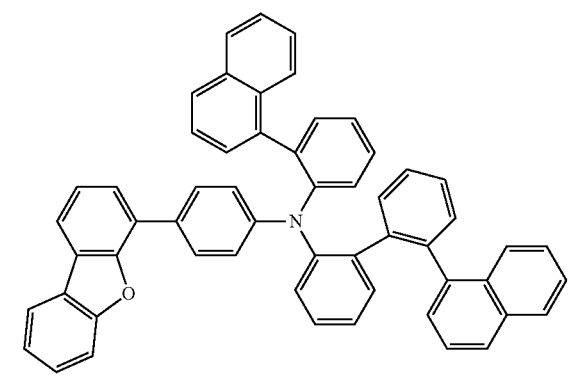
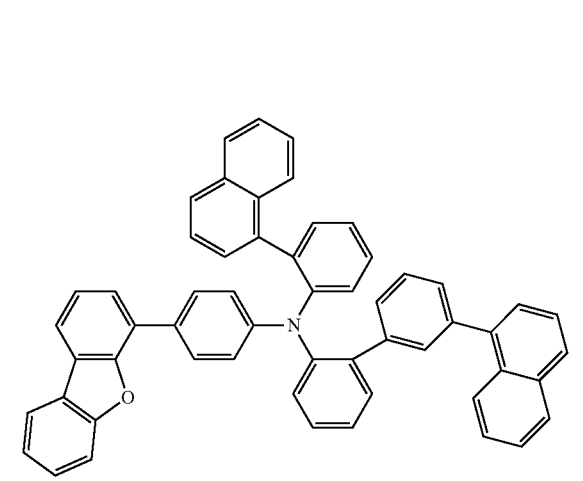
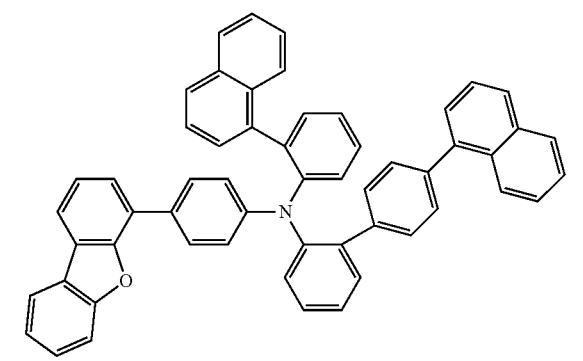
-continued
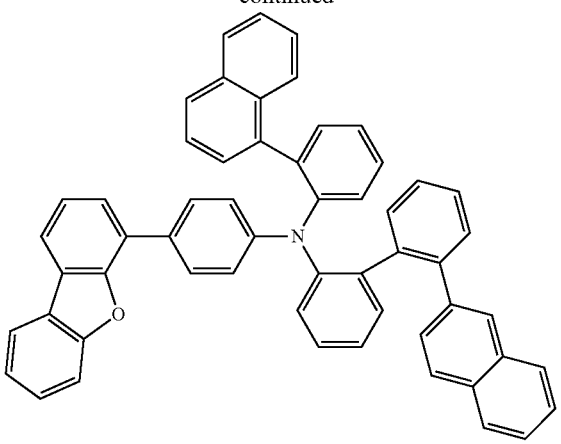
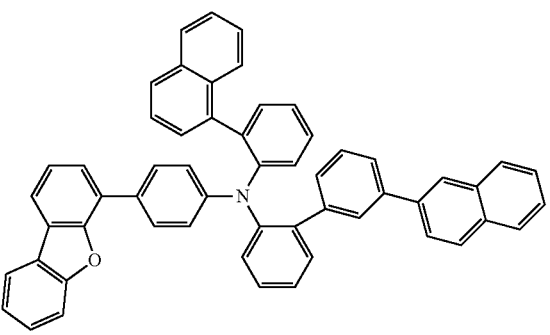
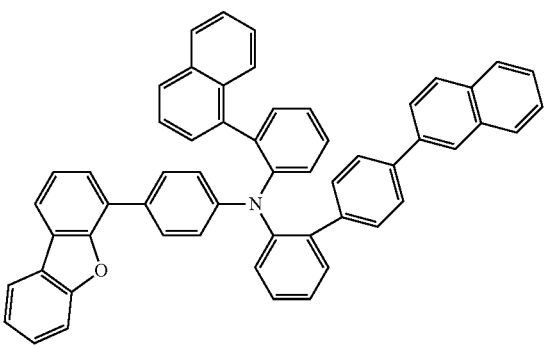
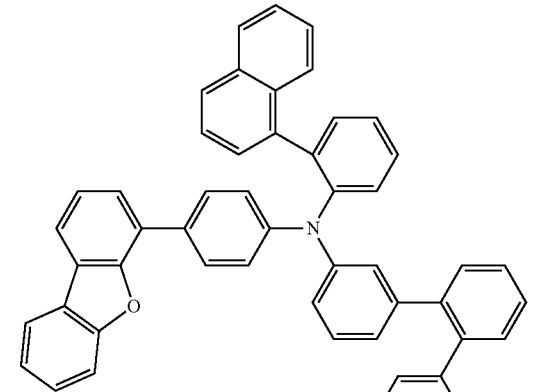

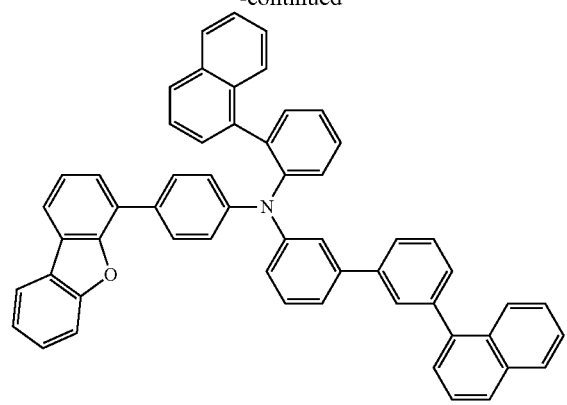
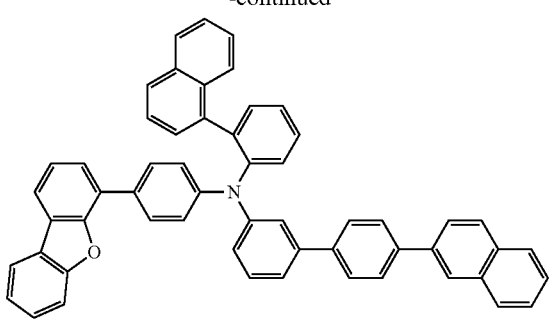
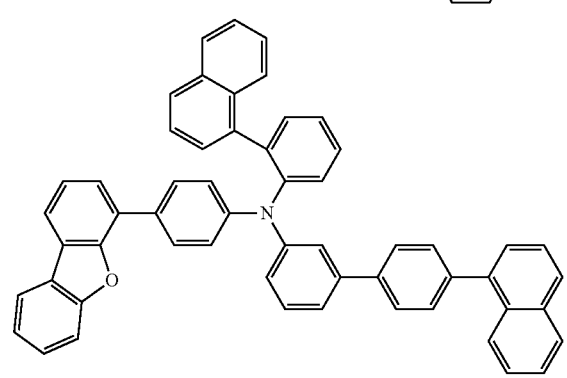
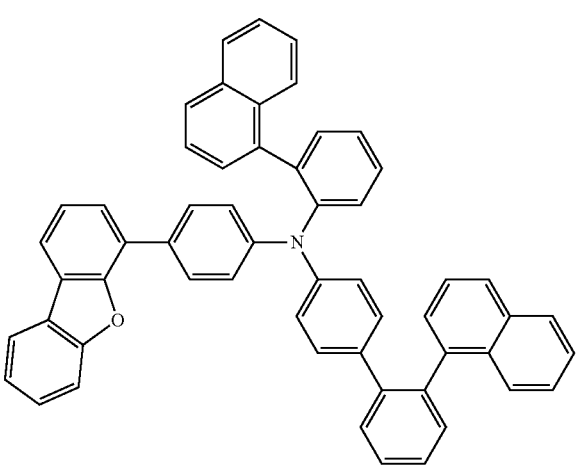
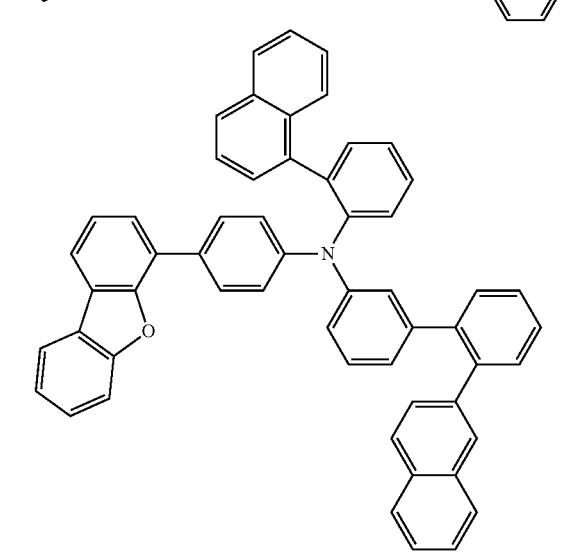
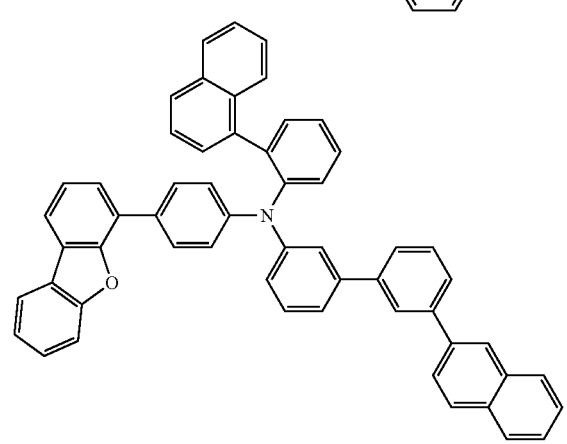

-continued
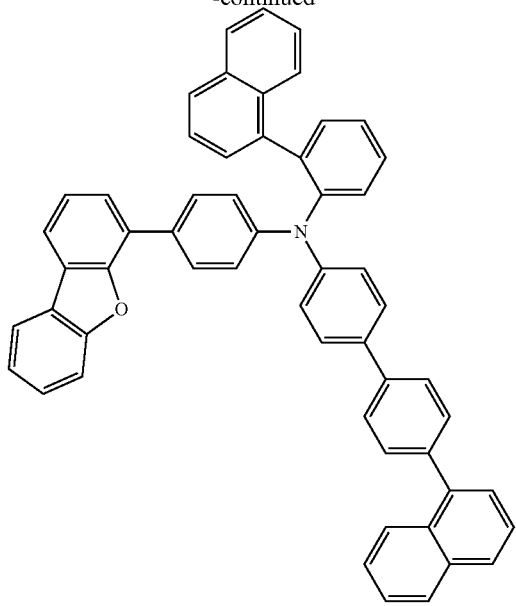
-continued
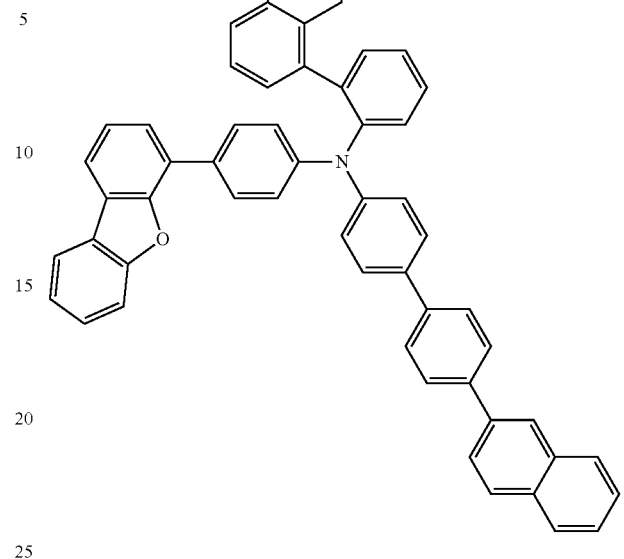
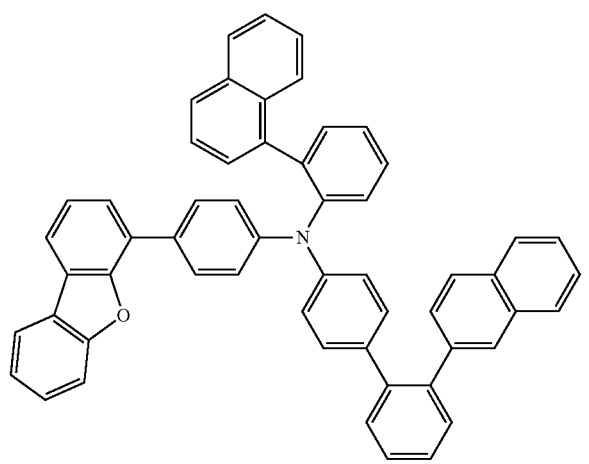
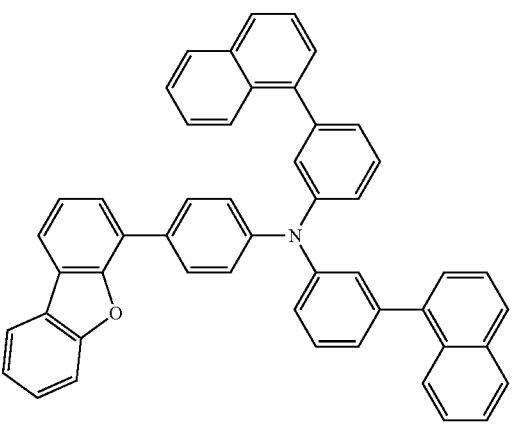
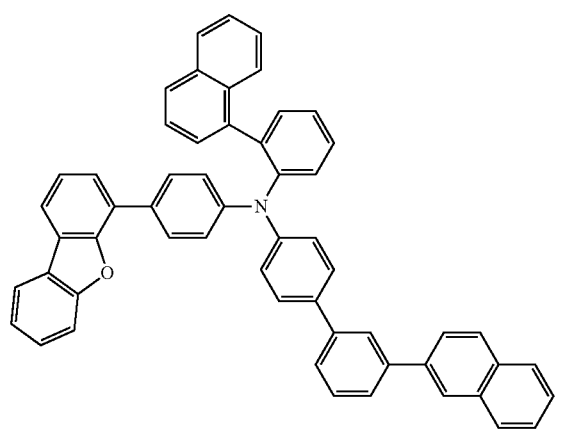
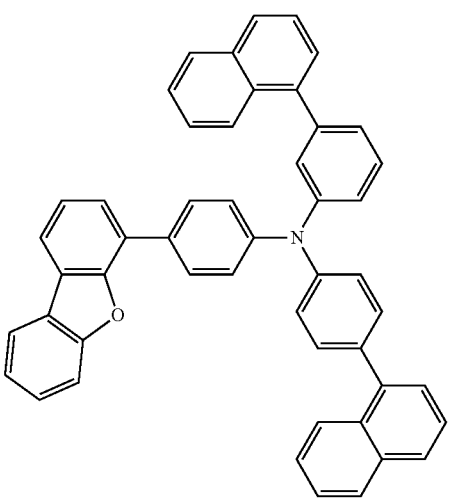

31
-continued
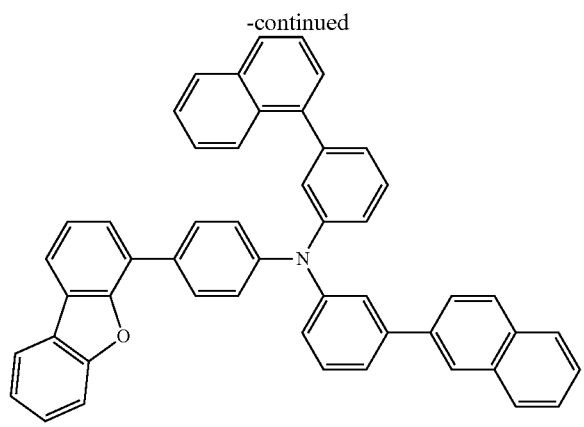
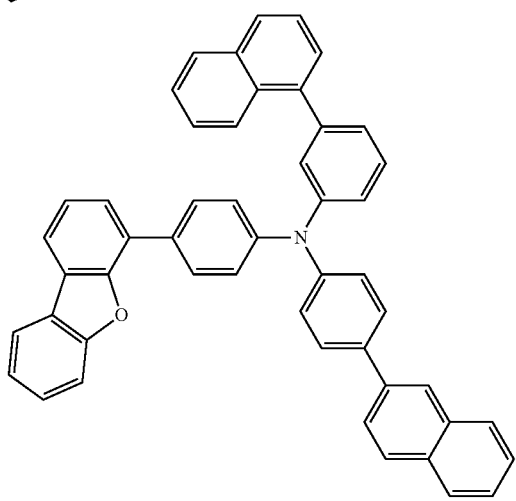
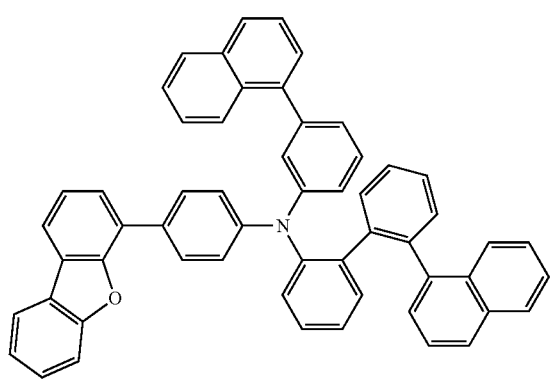
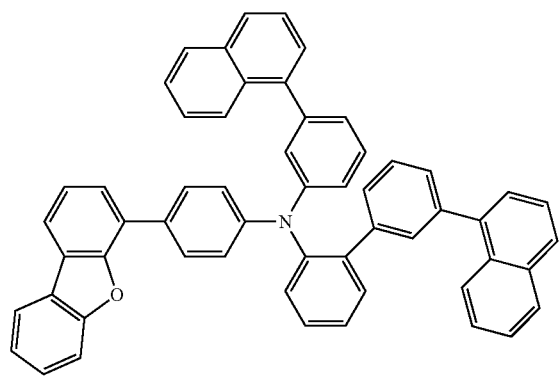
32
-continued
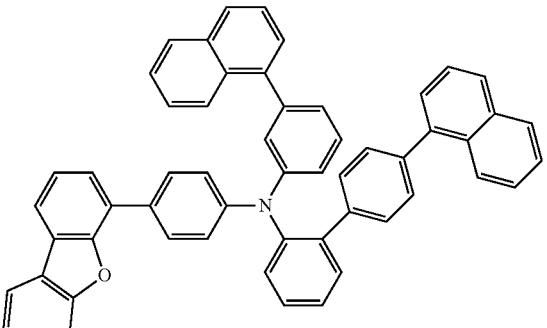
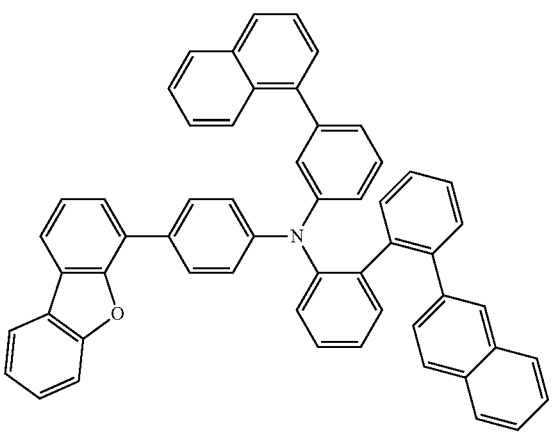
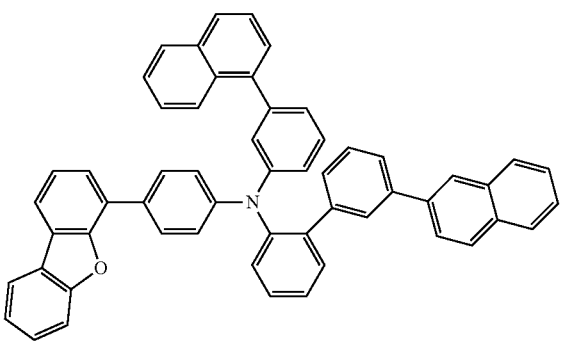
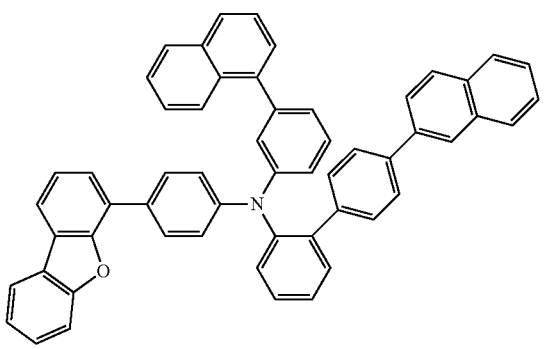

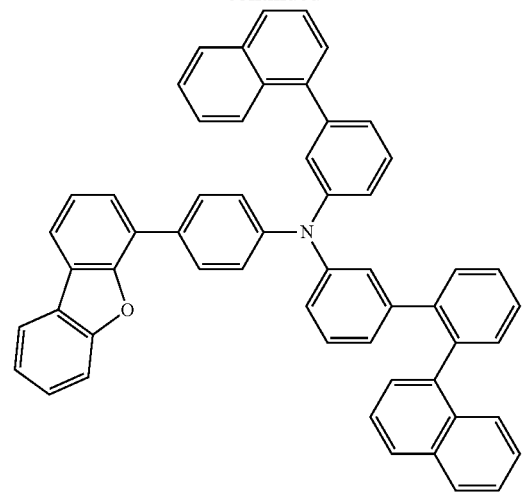
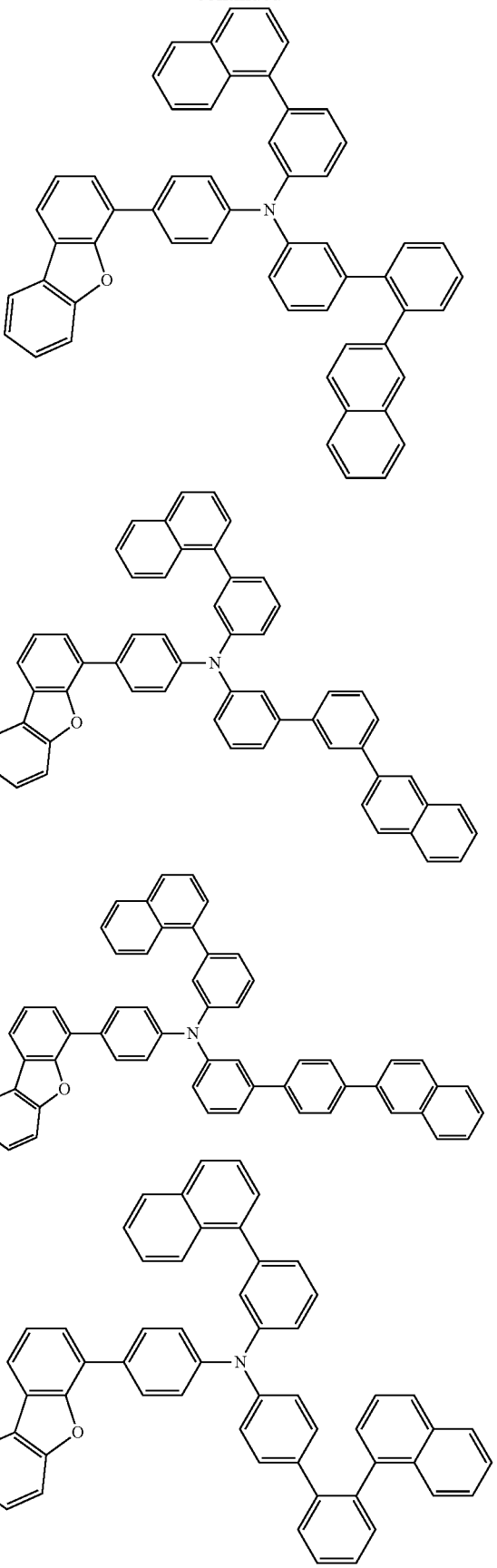

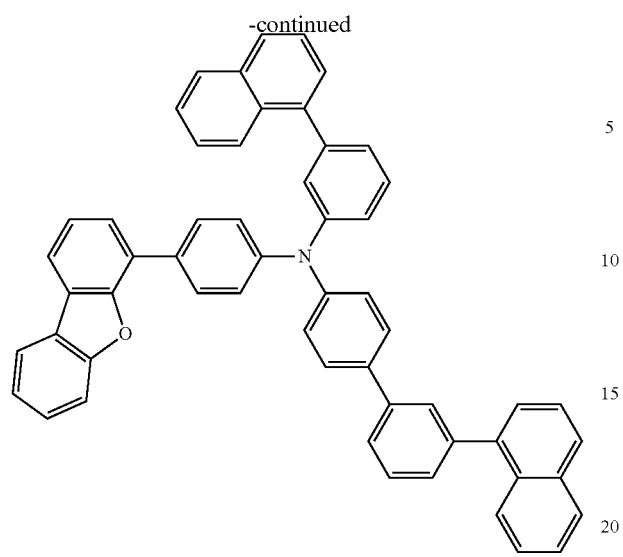
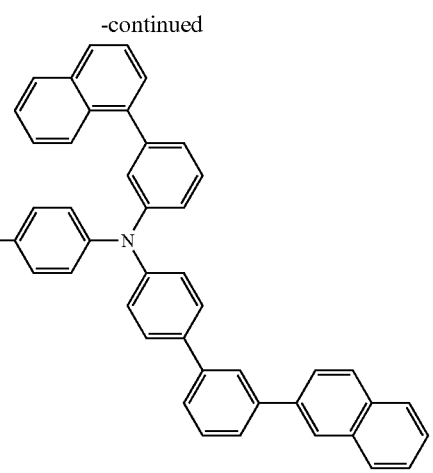
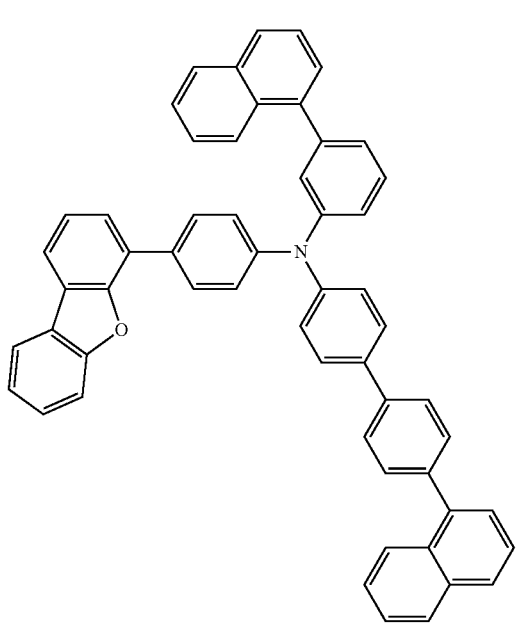
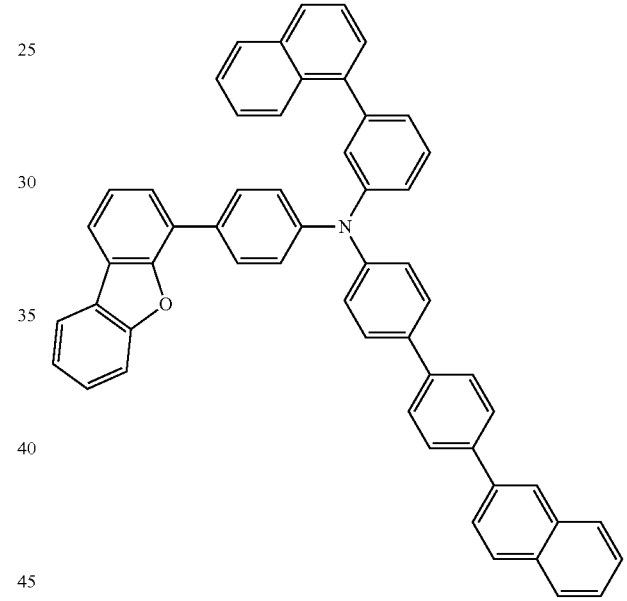
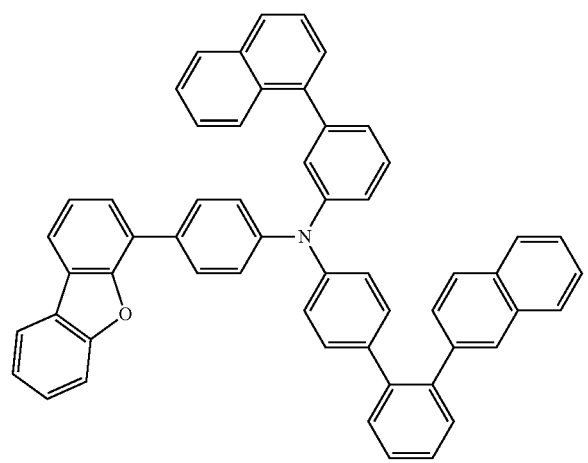
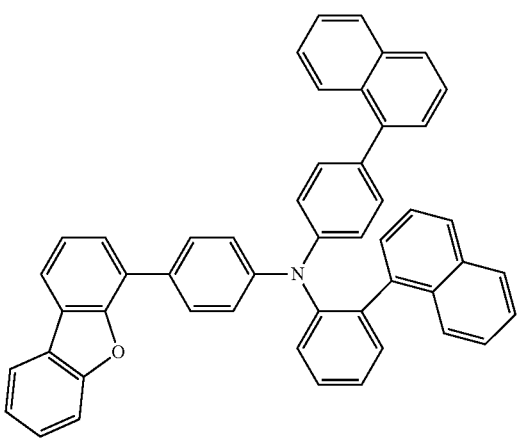

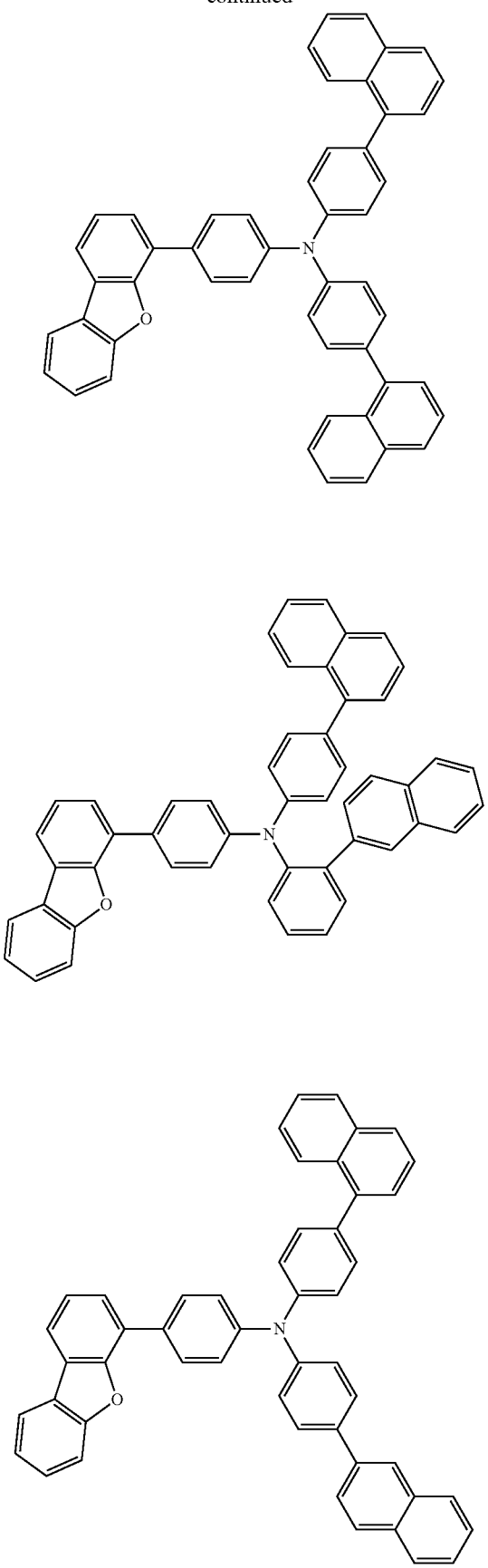
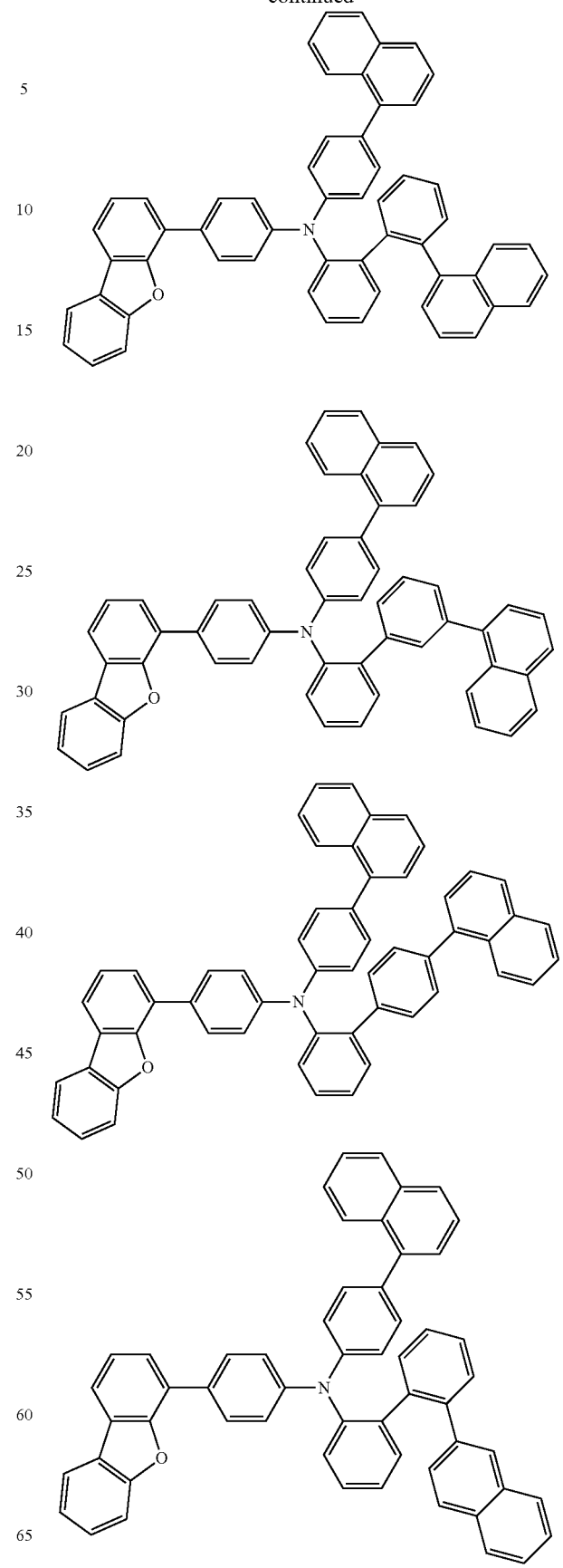

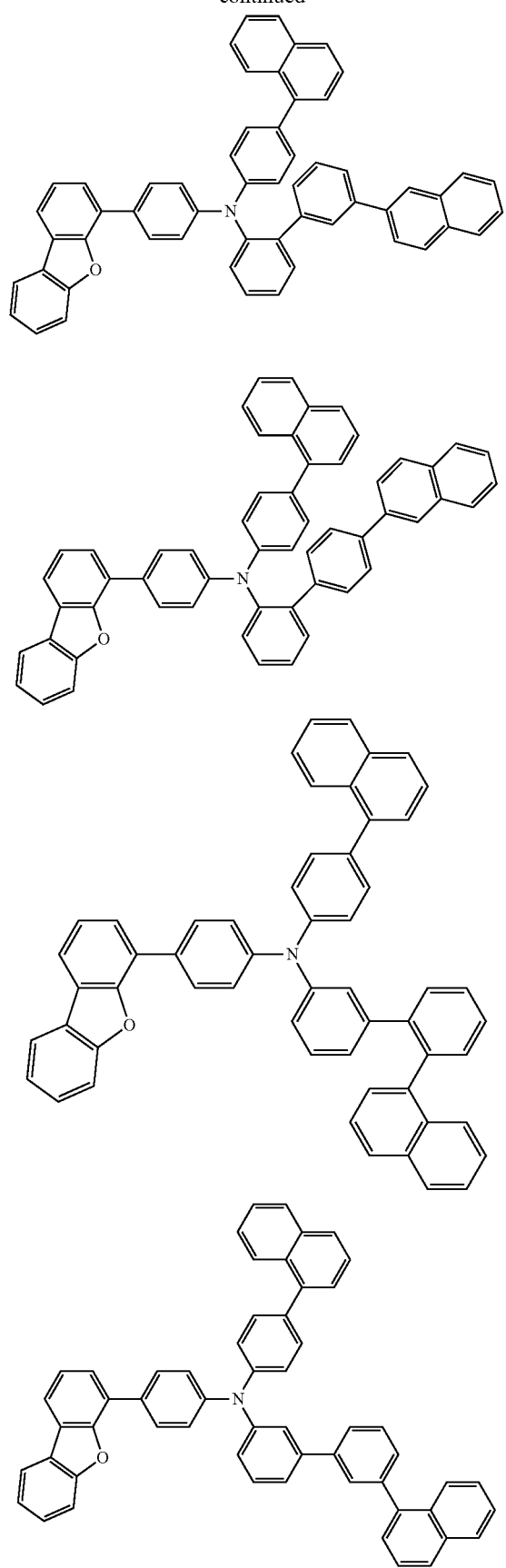
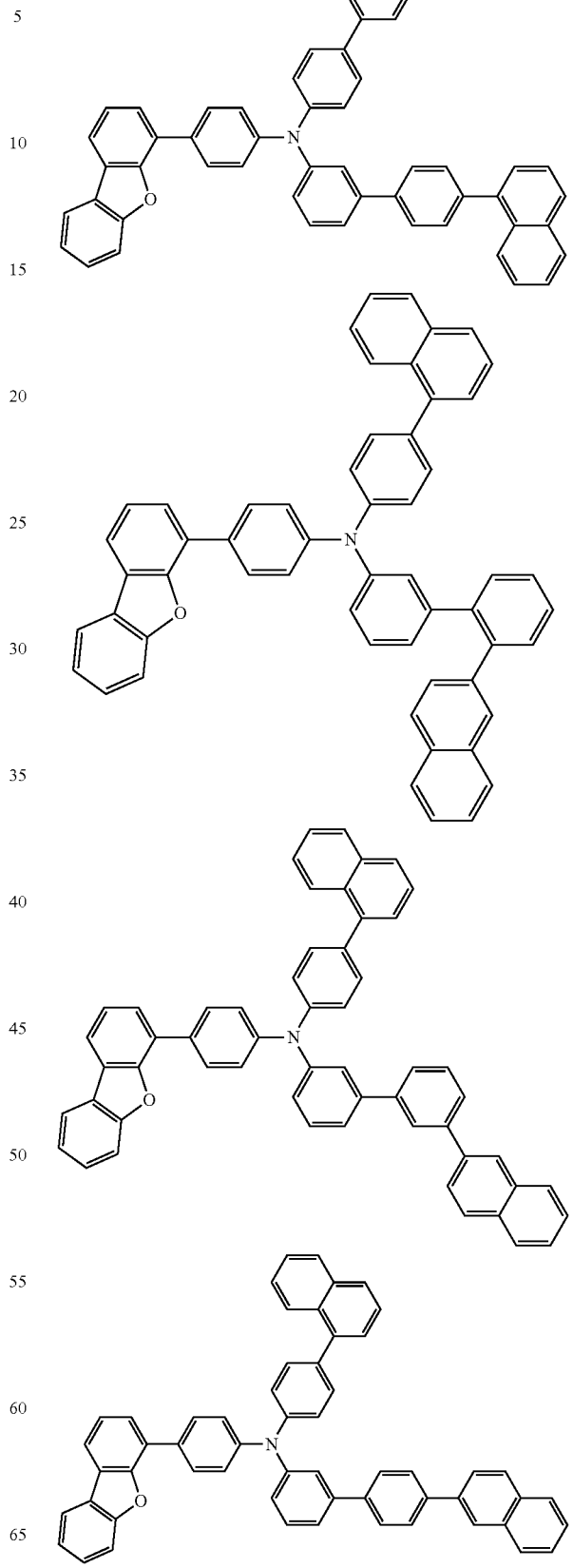

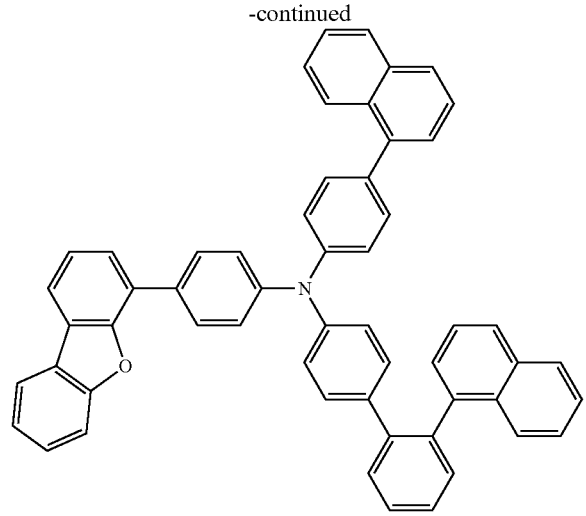
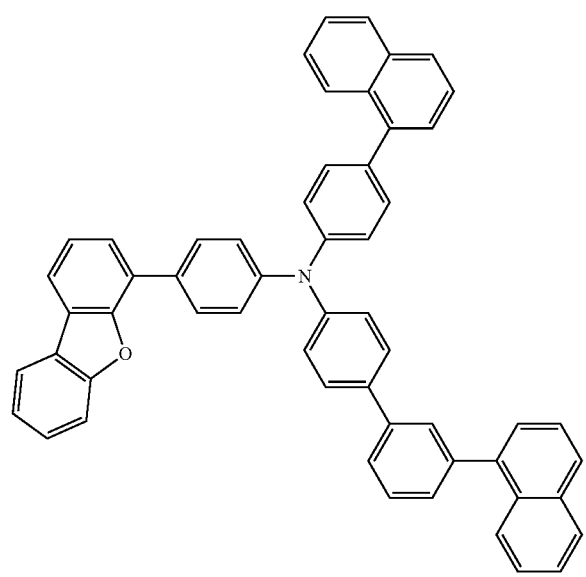
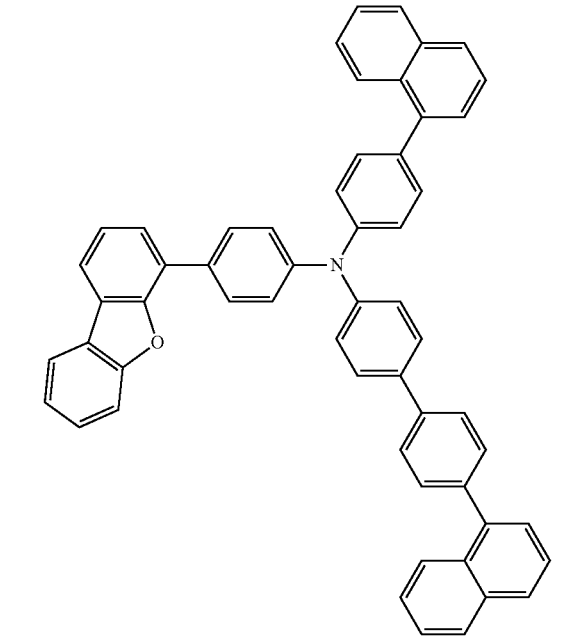
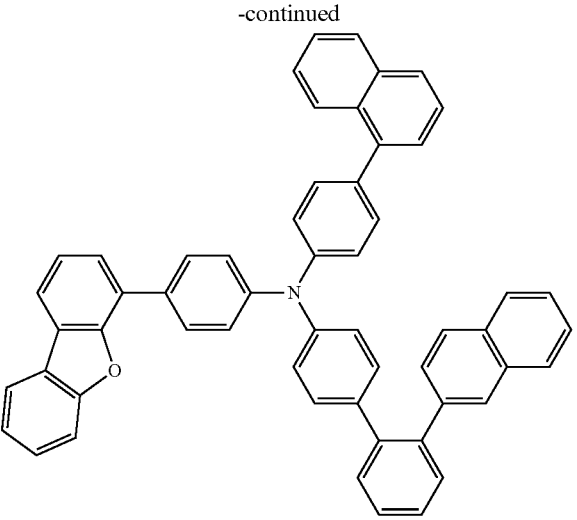
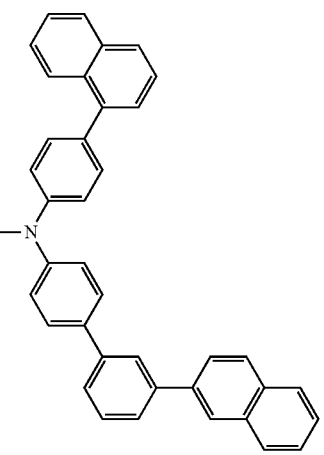
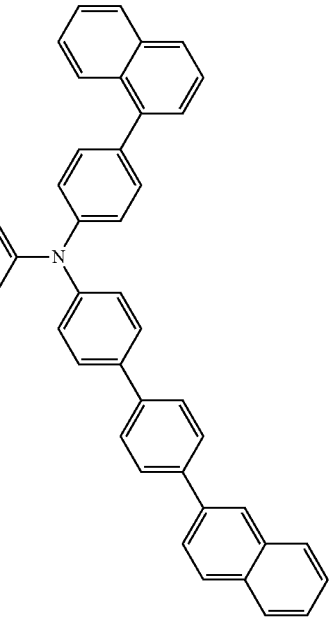

-continued
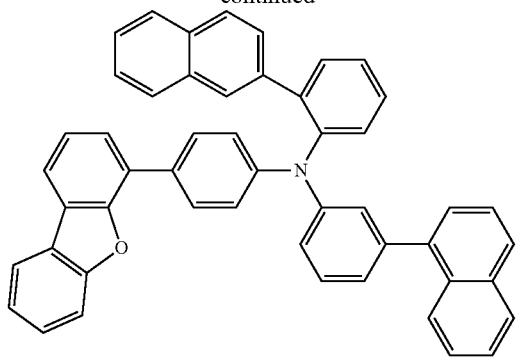
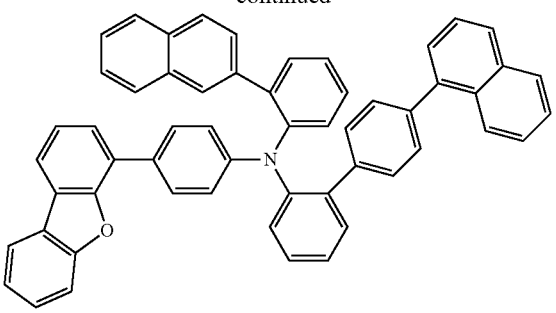
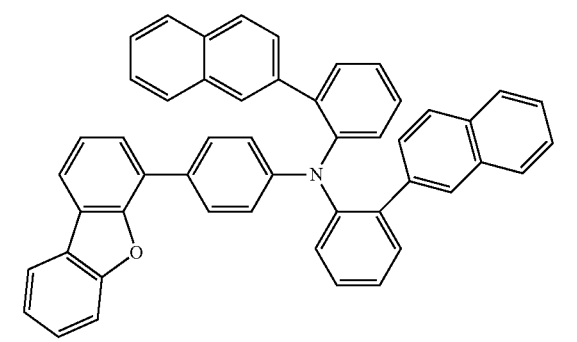
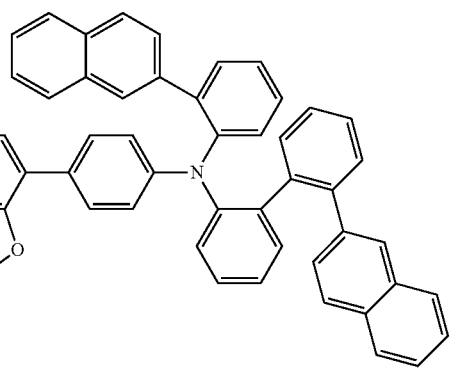
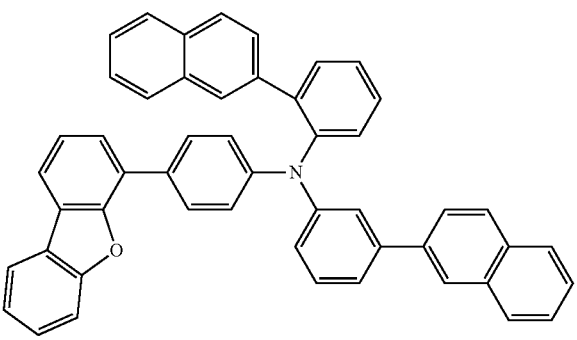
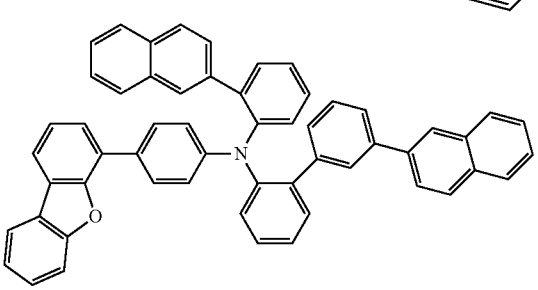
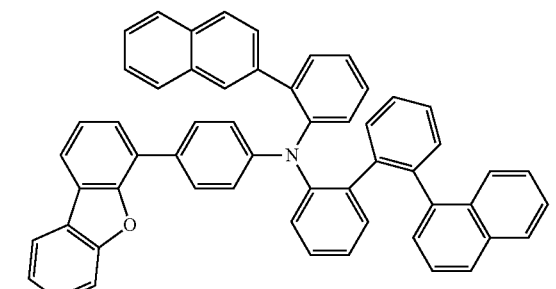
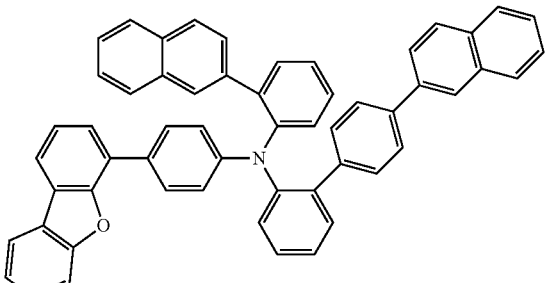
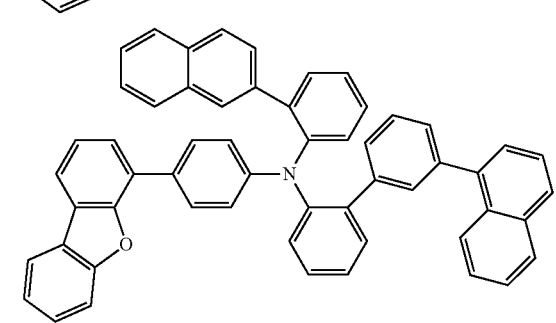
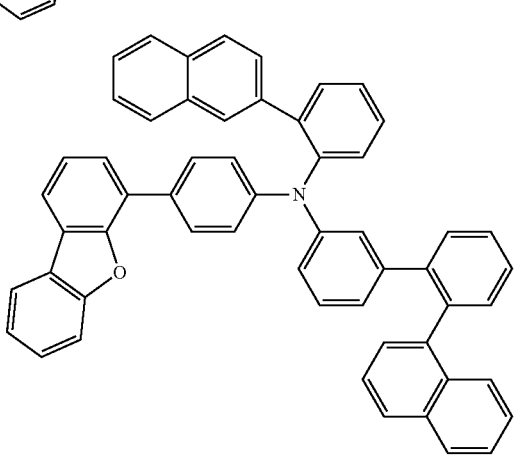

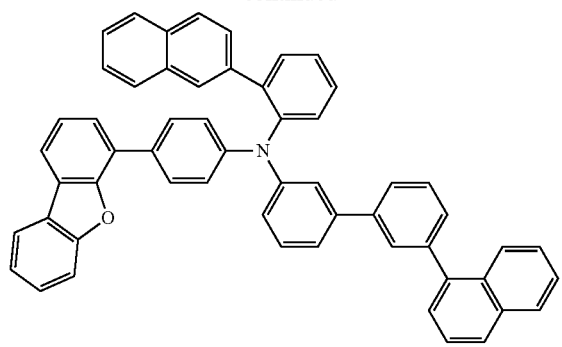
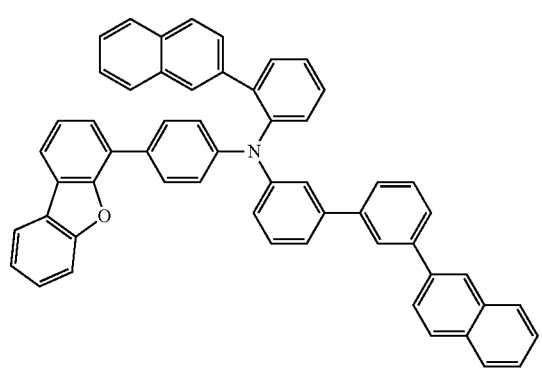
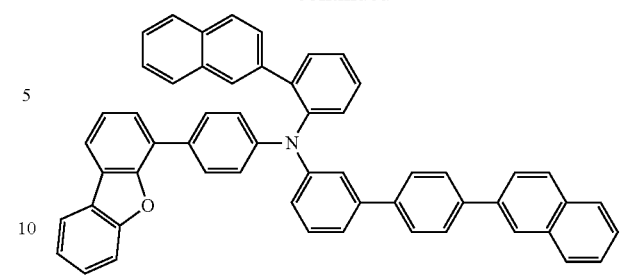
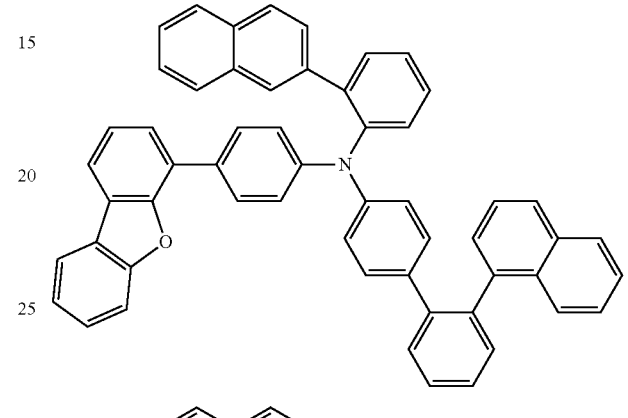
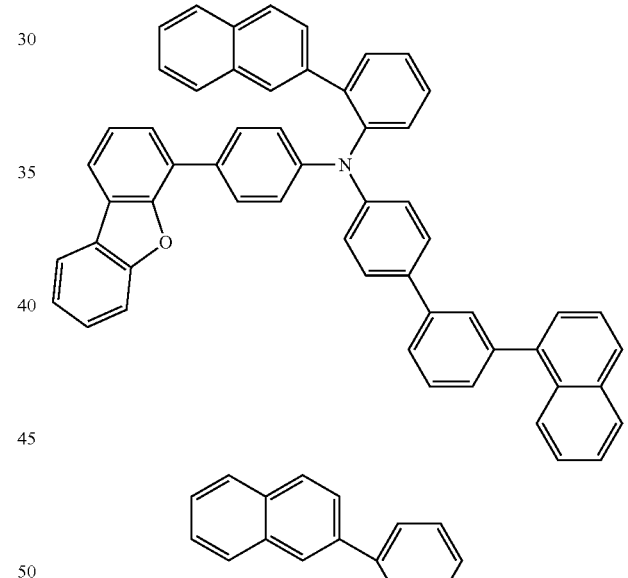
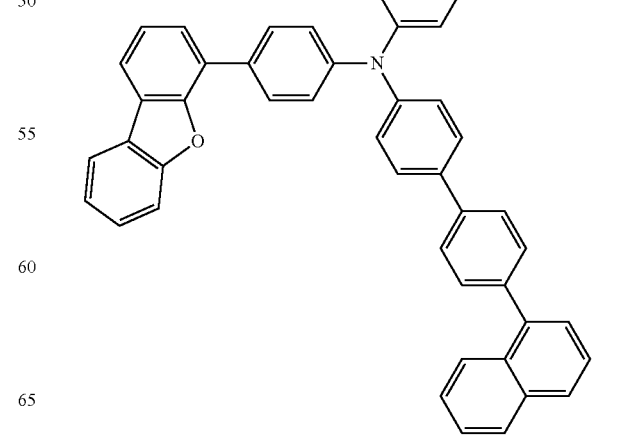

47
-continued
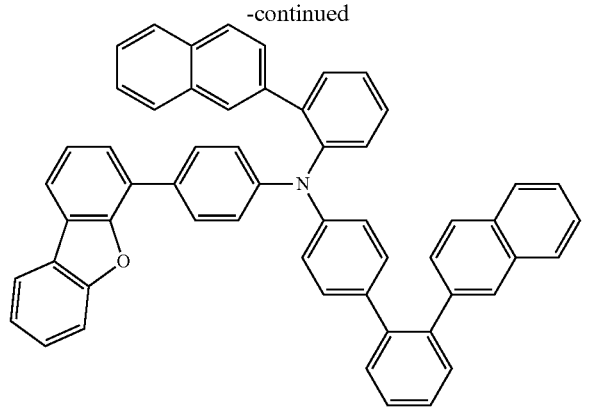
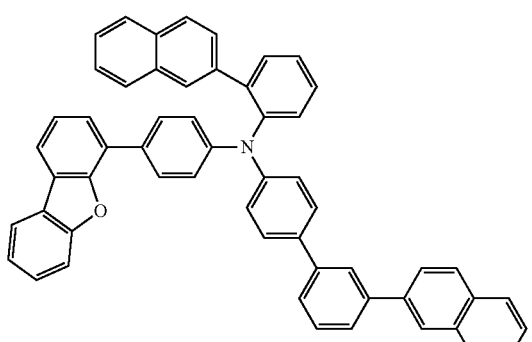
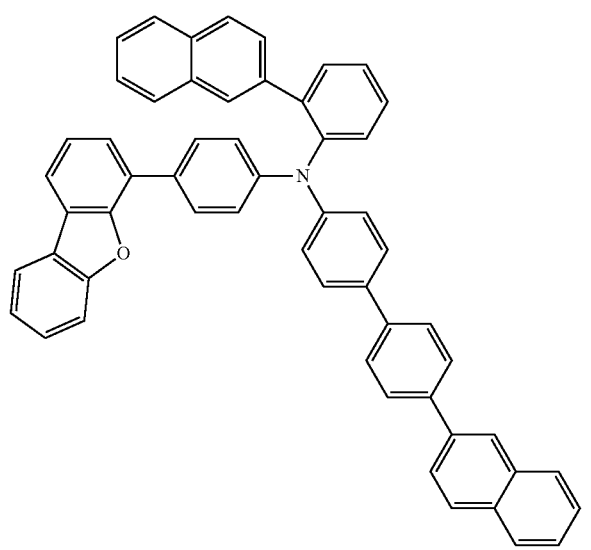
48
-continued
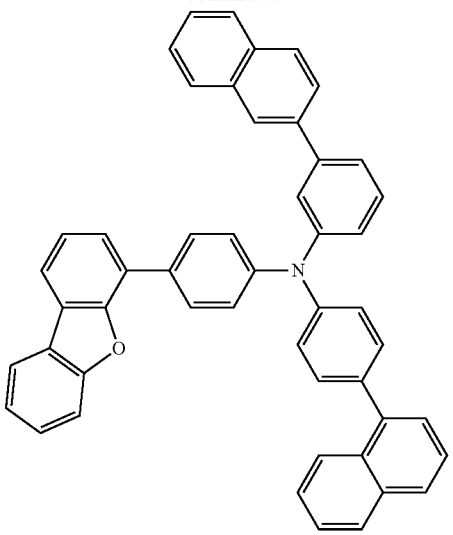
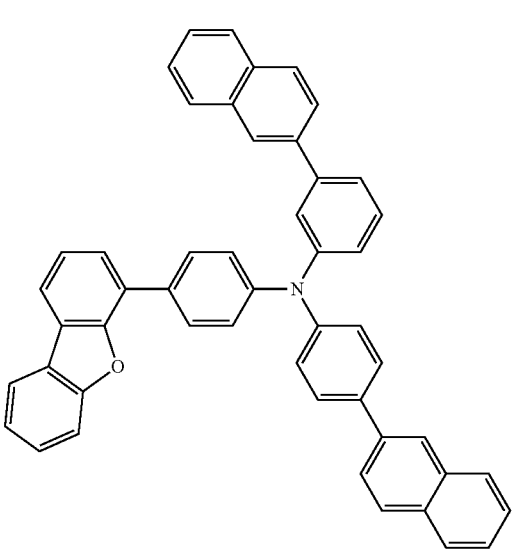

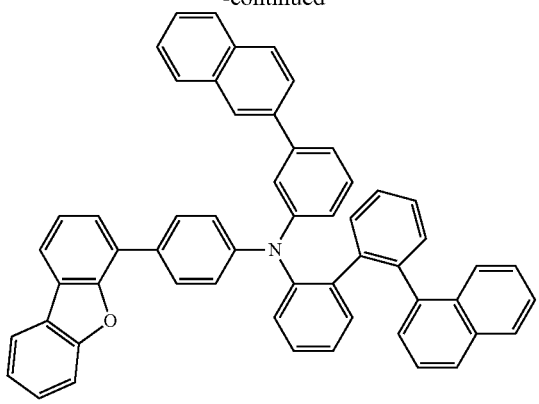
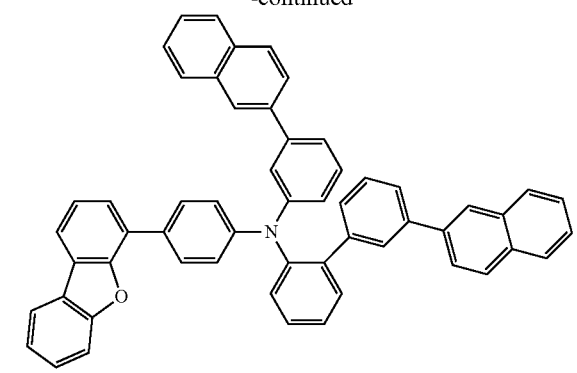
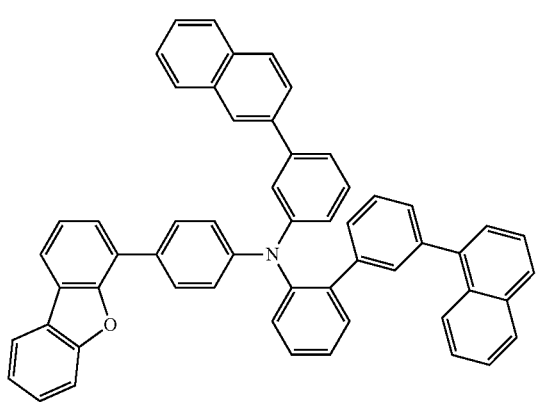
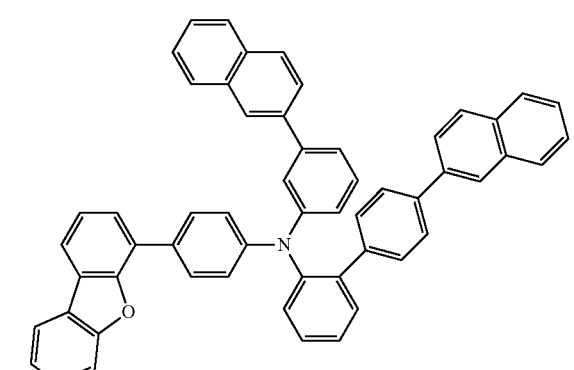
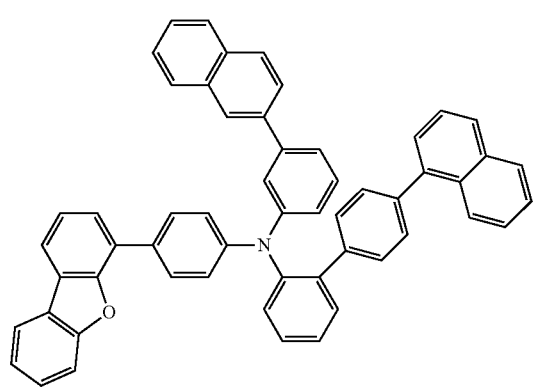
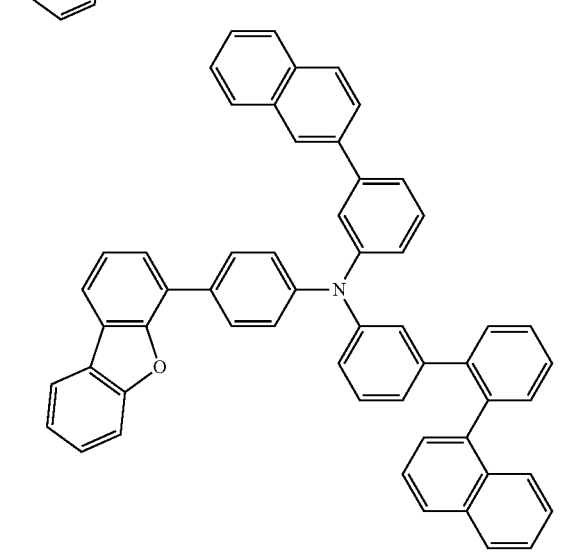
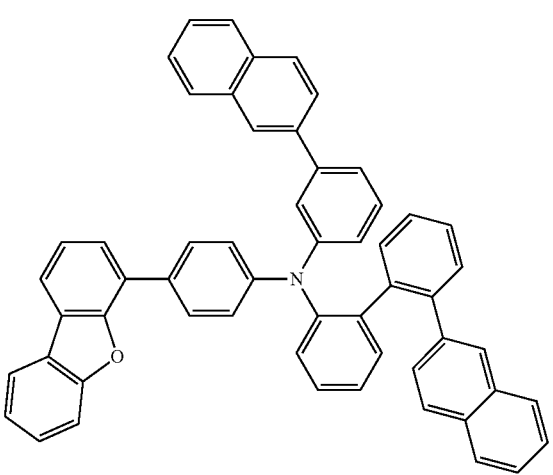
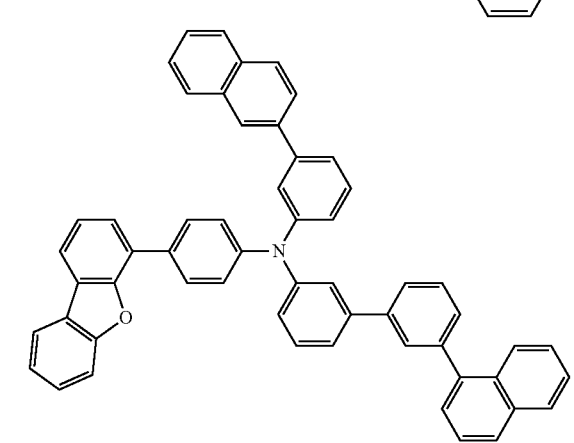

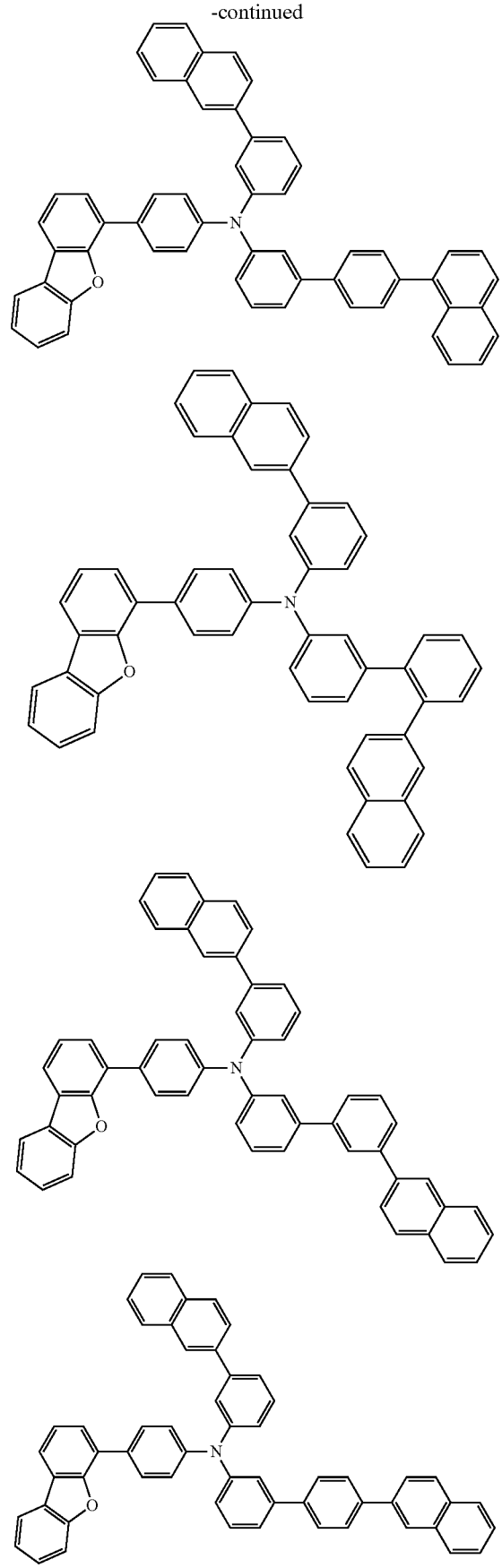
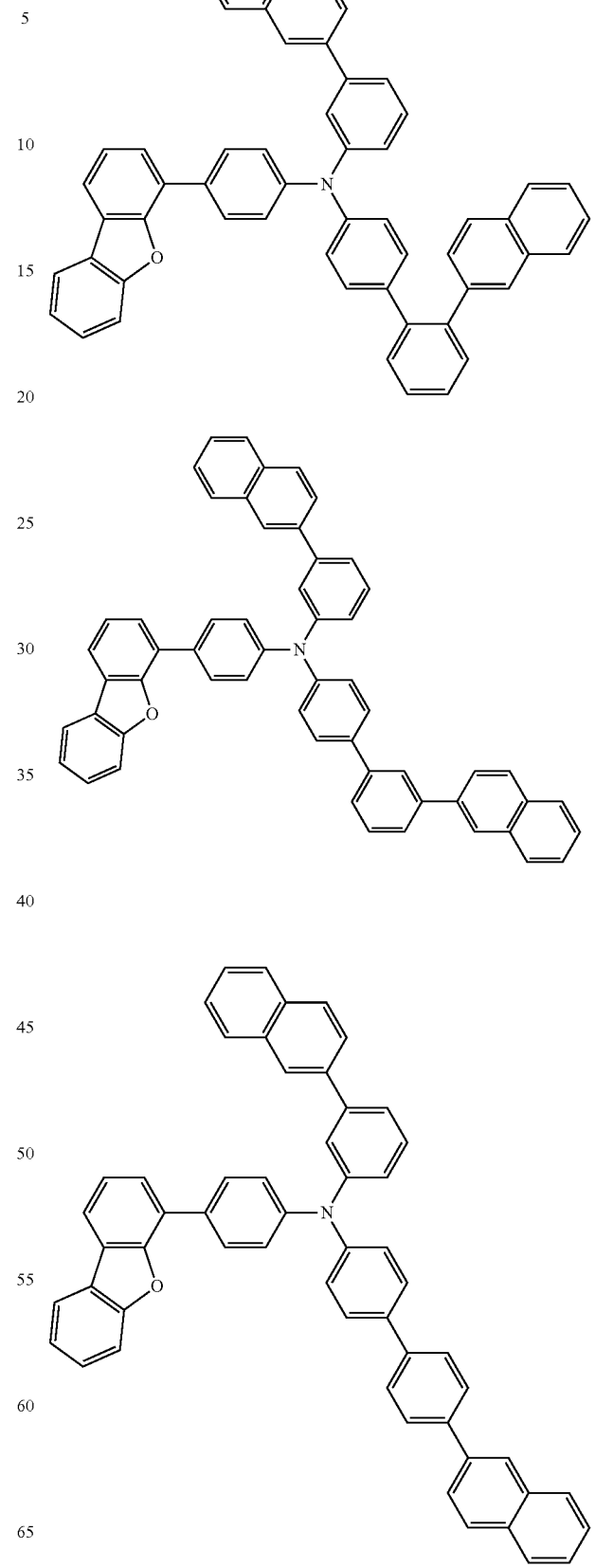

-continued
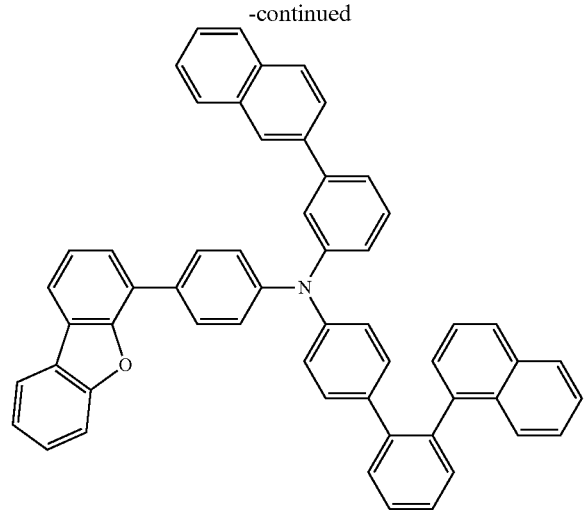
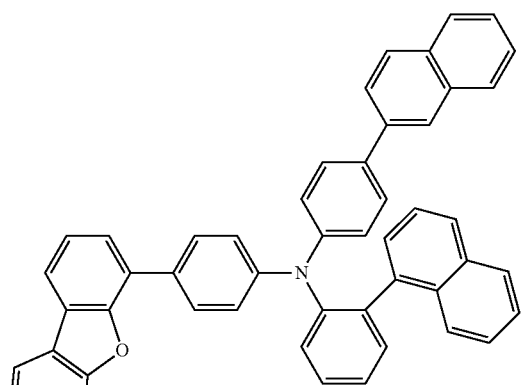
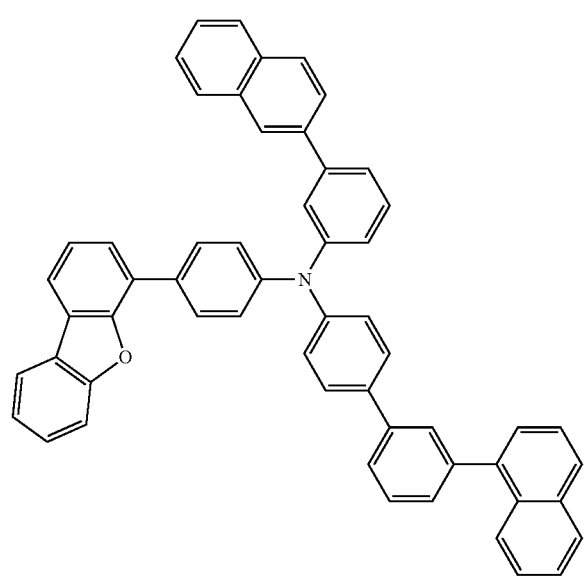
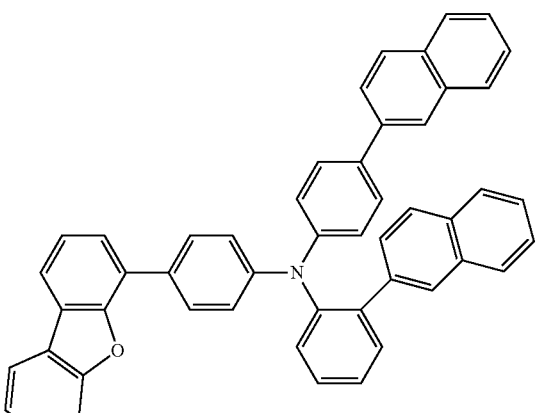
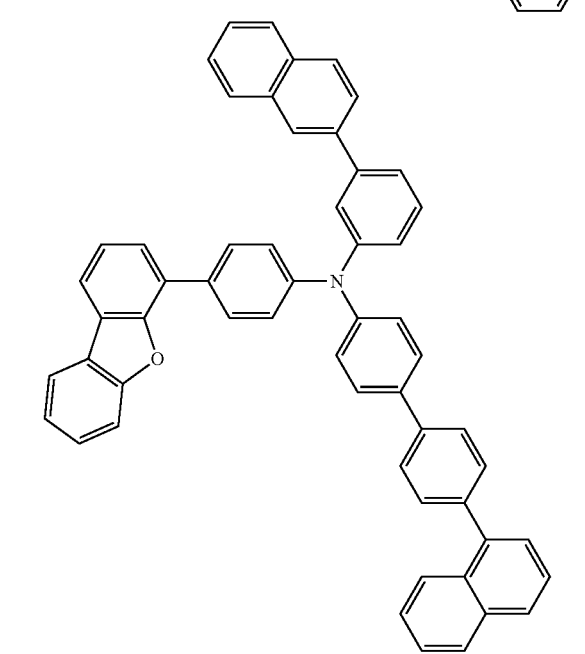
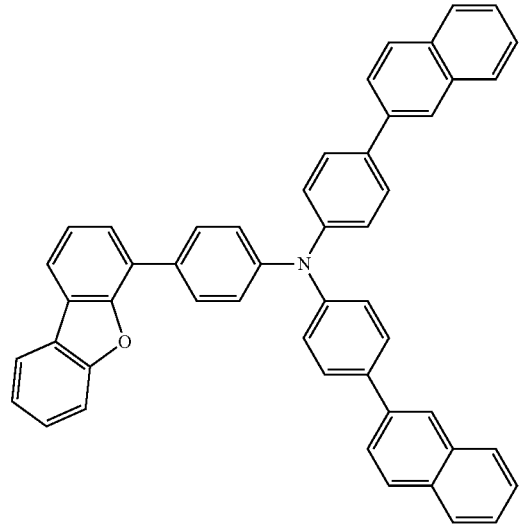

-continued
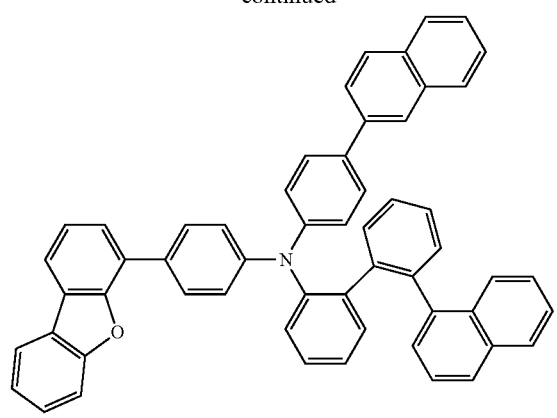
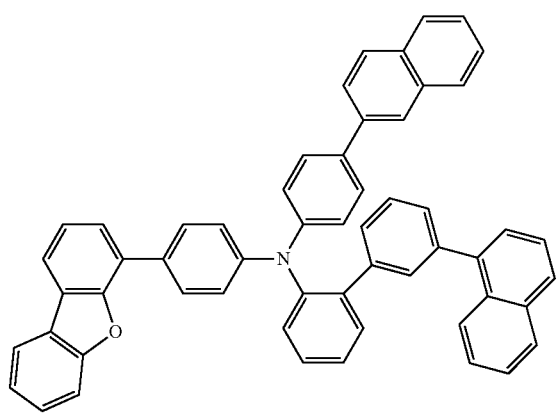
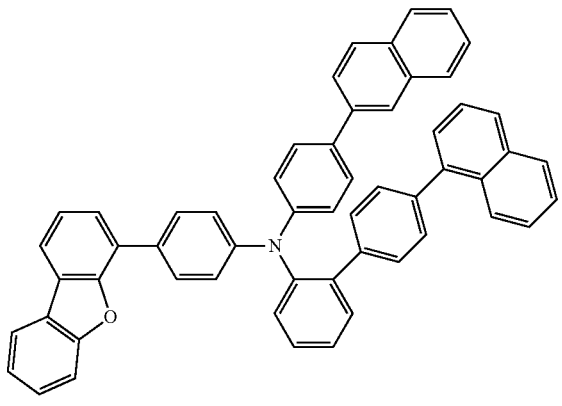
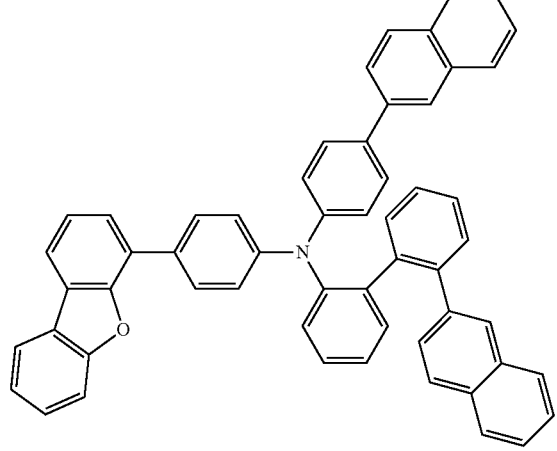
-continued
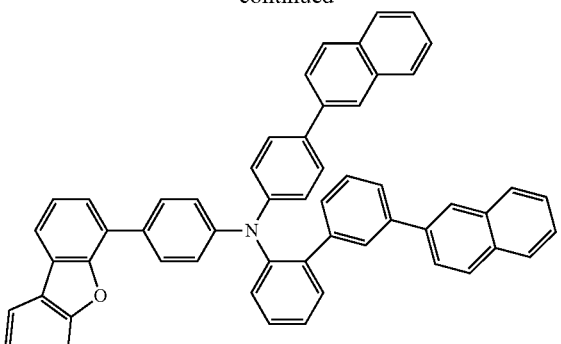
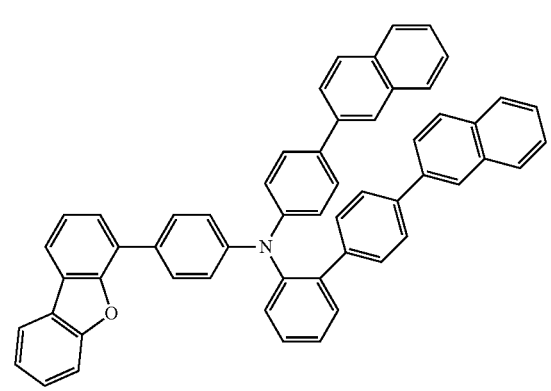
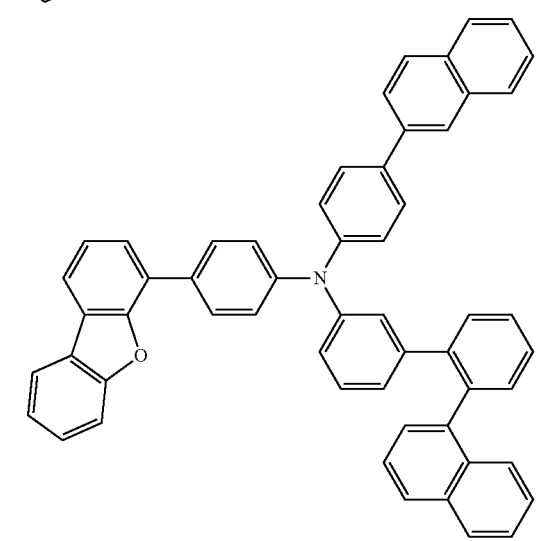
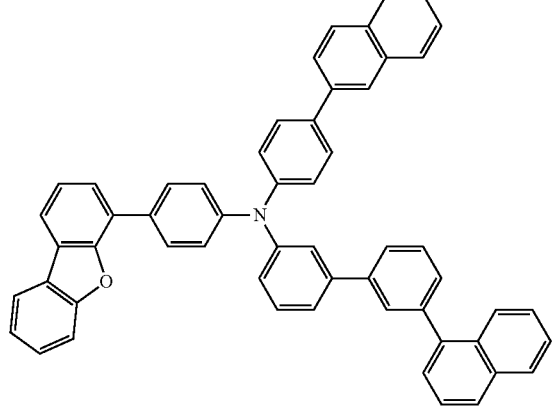

57
-continued
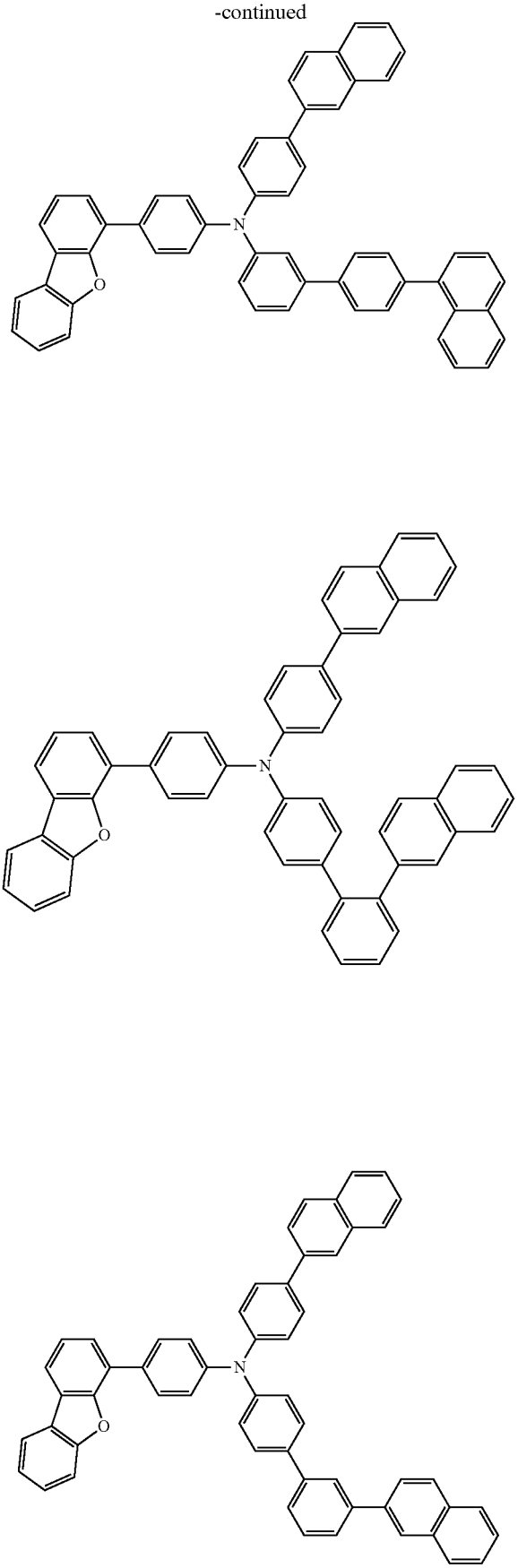
58
-continued
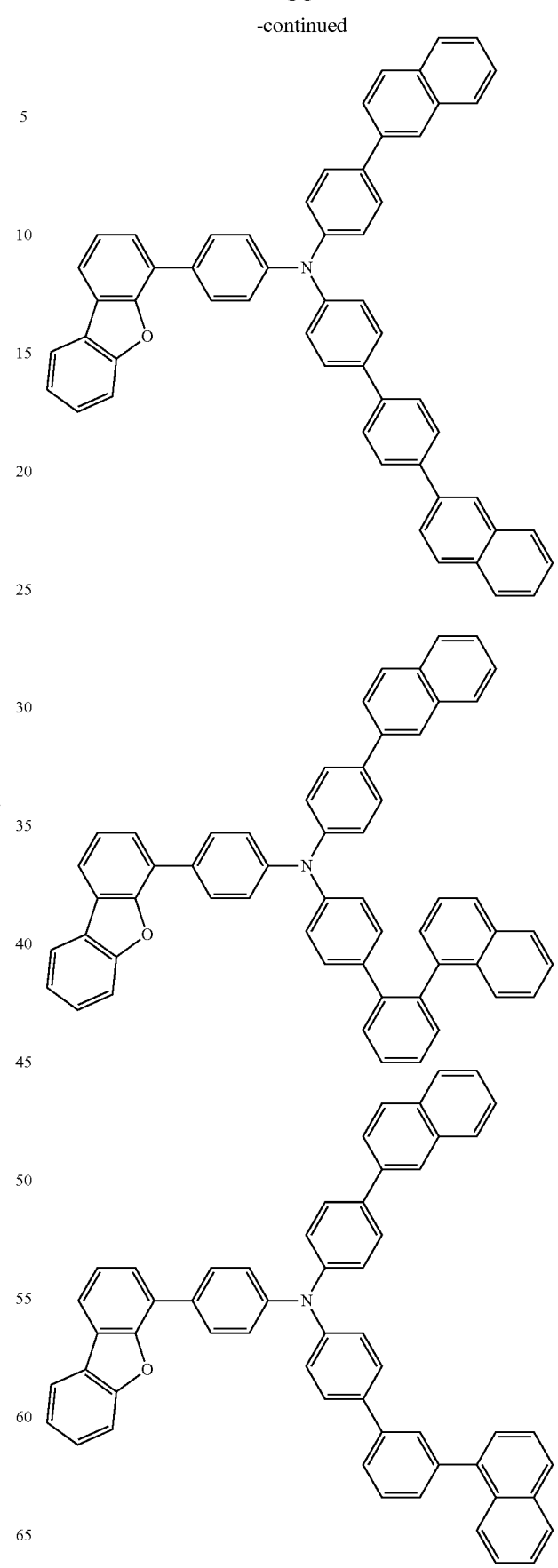

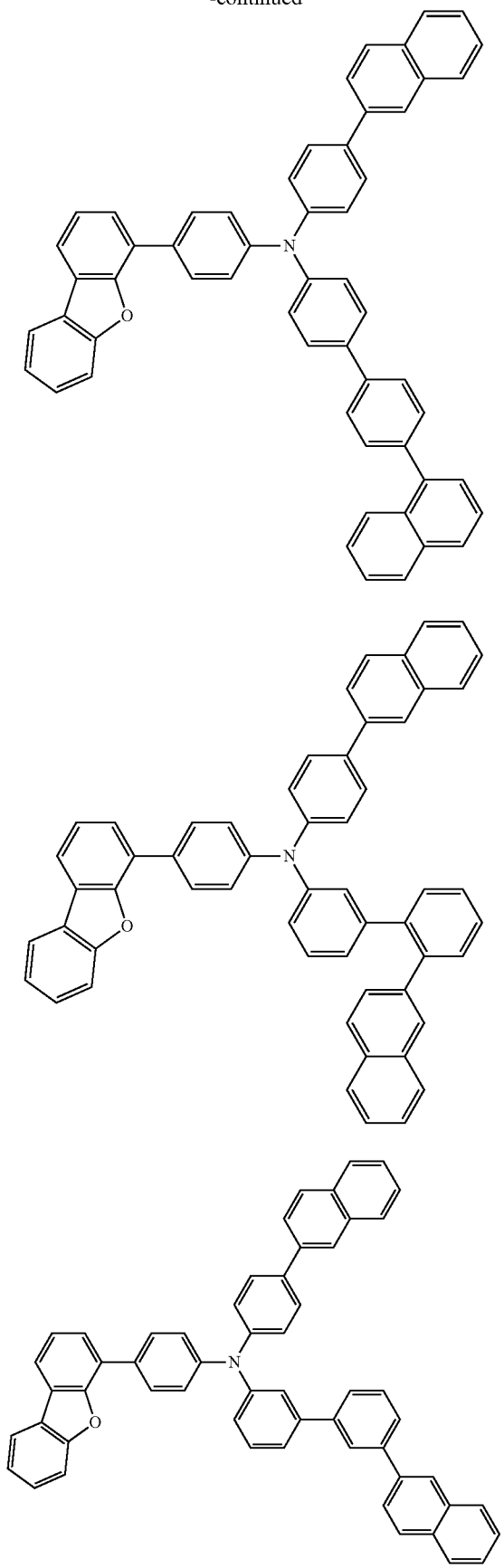
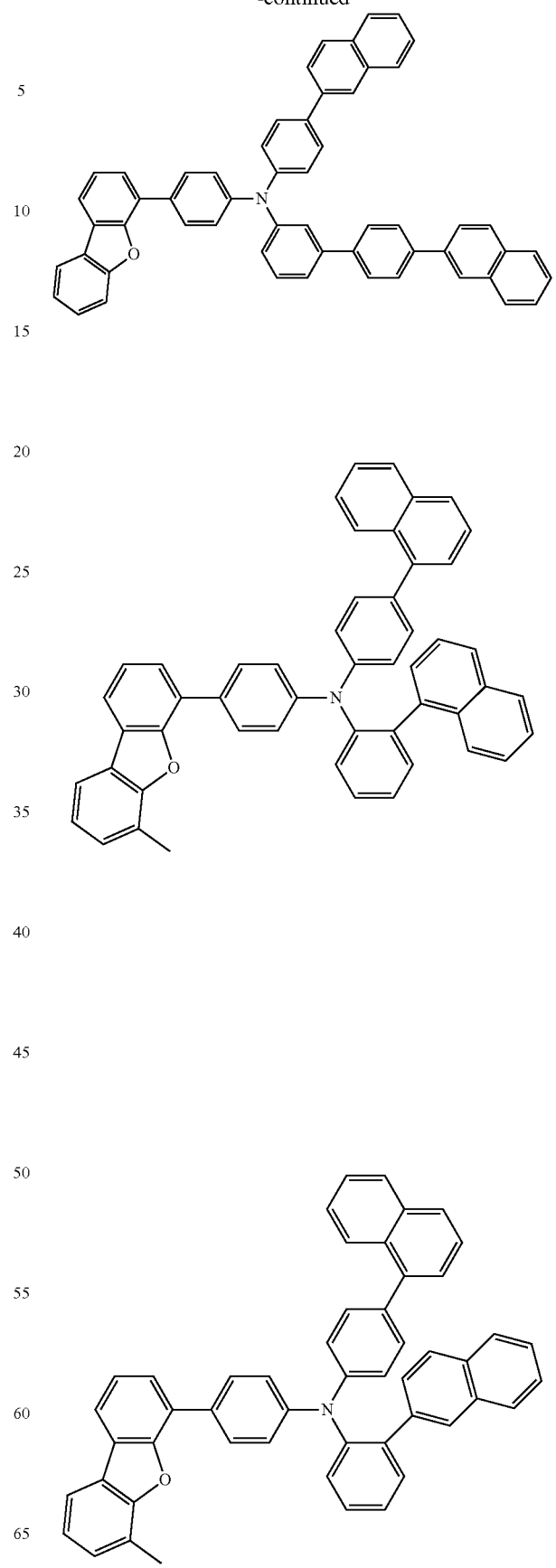

61
-continued
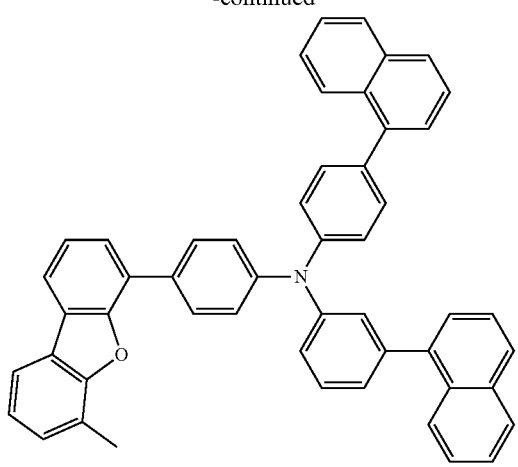
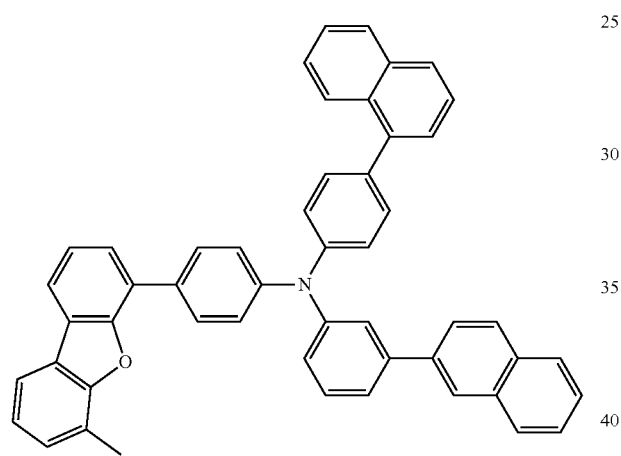
62
-continued
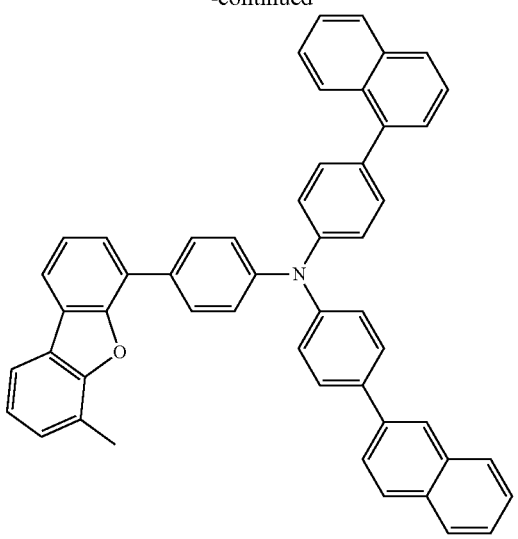
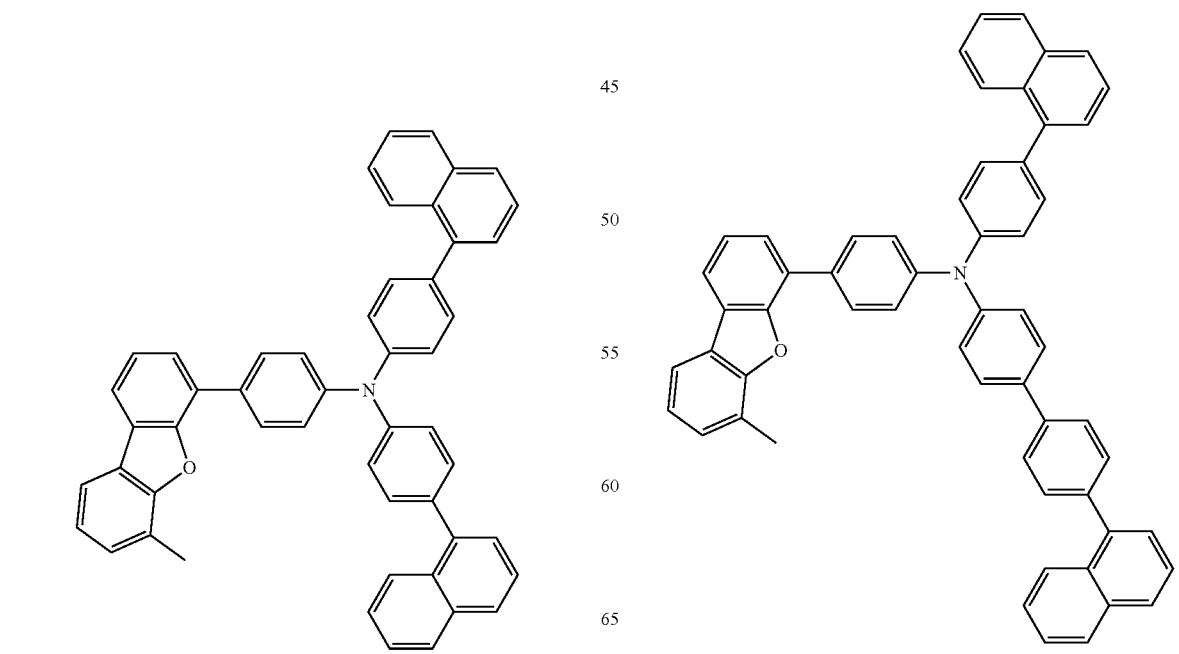

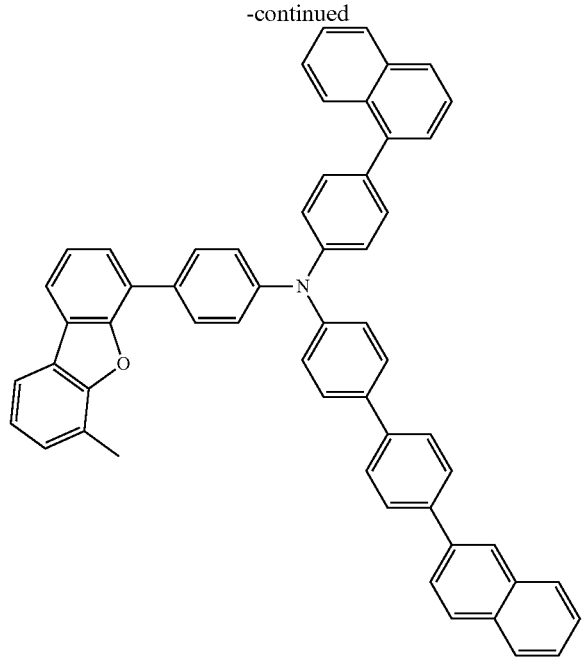
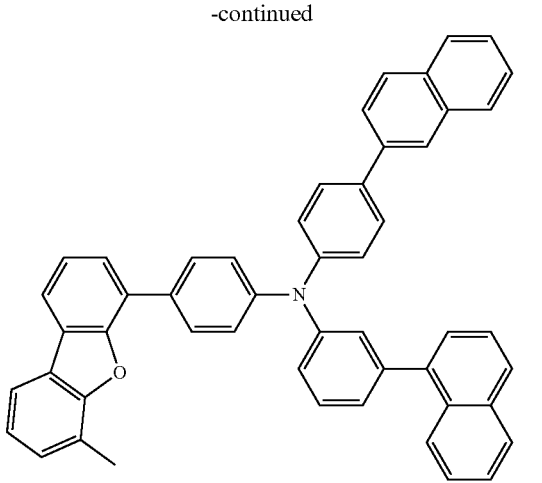
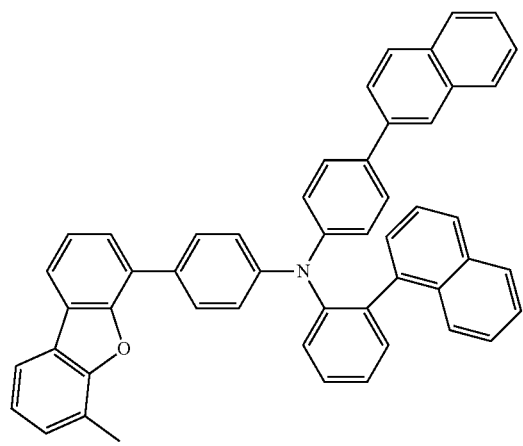
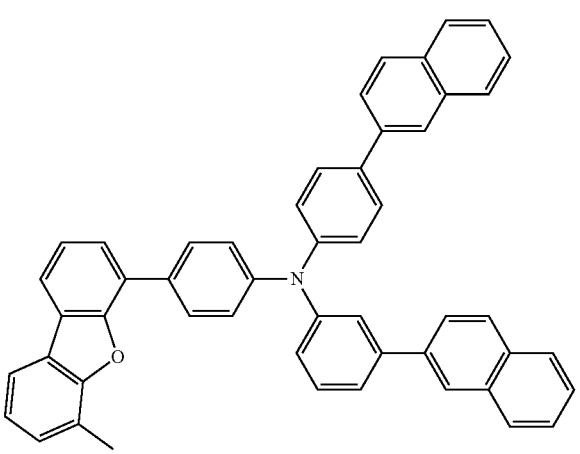
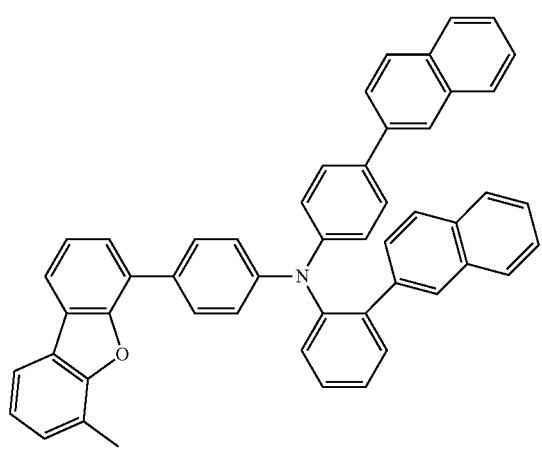
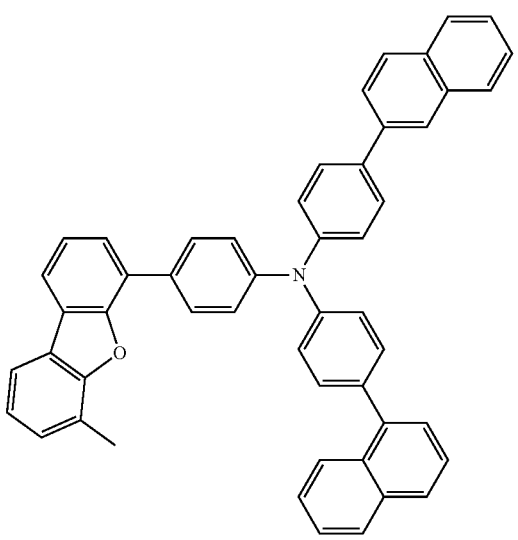

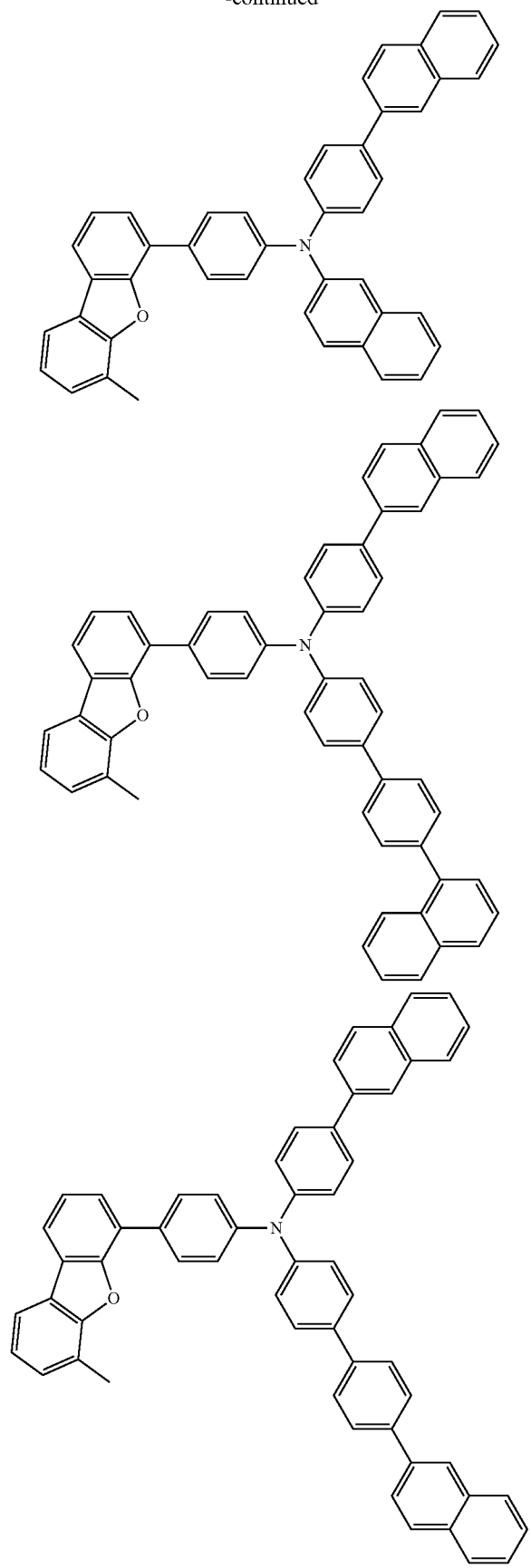
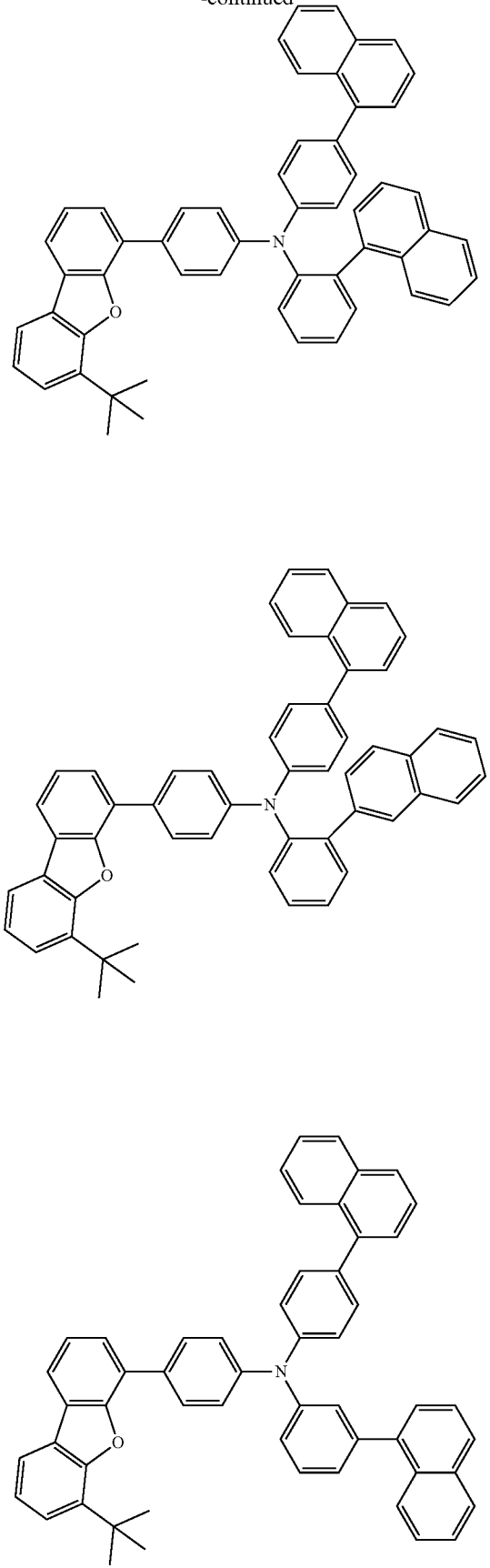

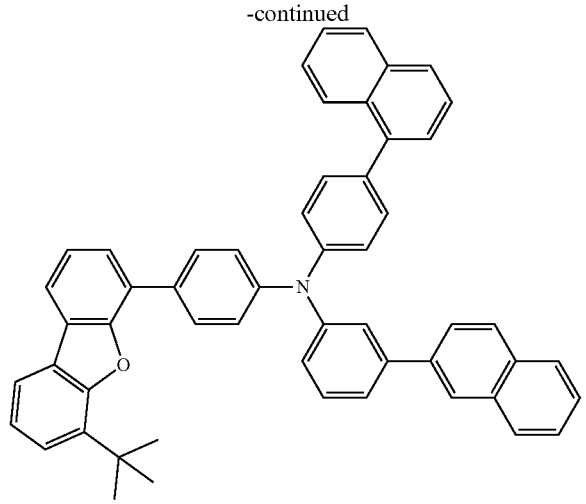
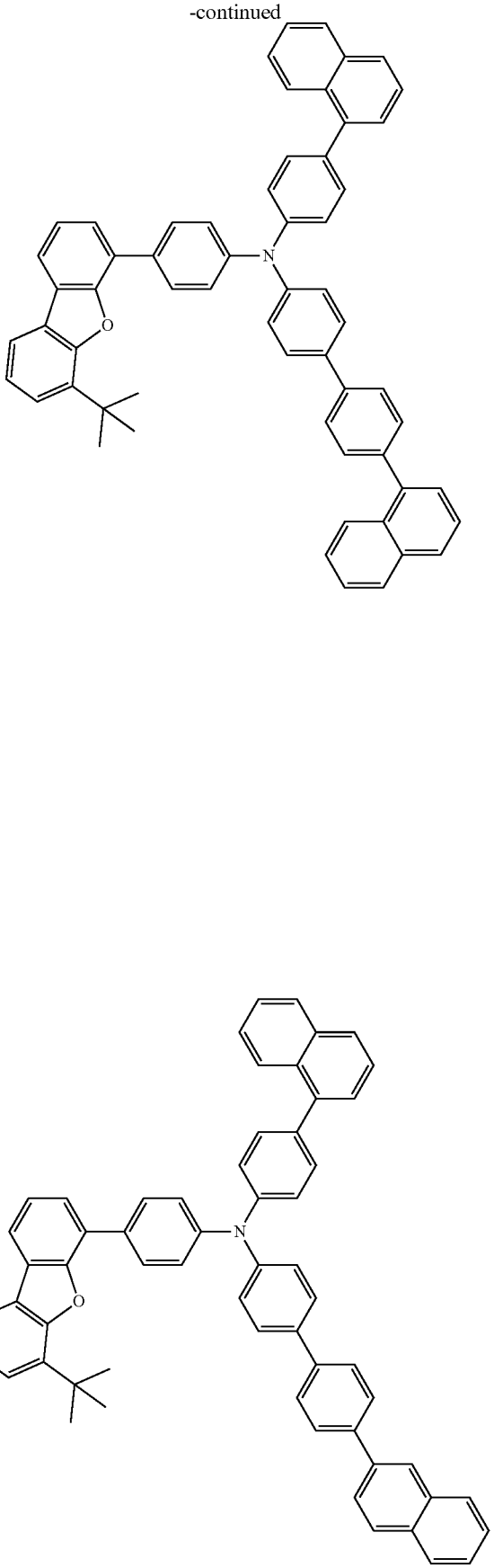

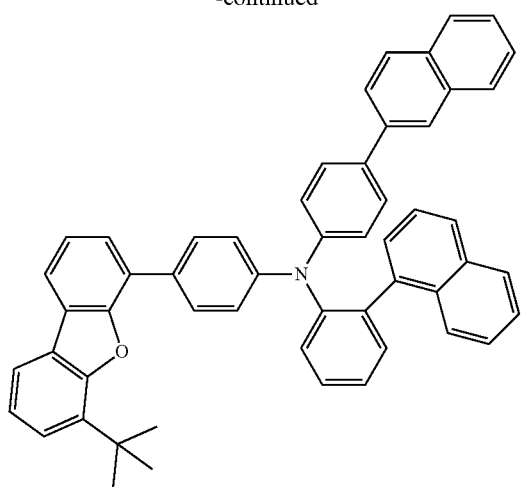
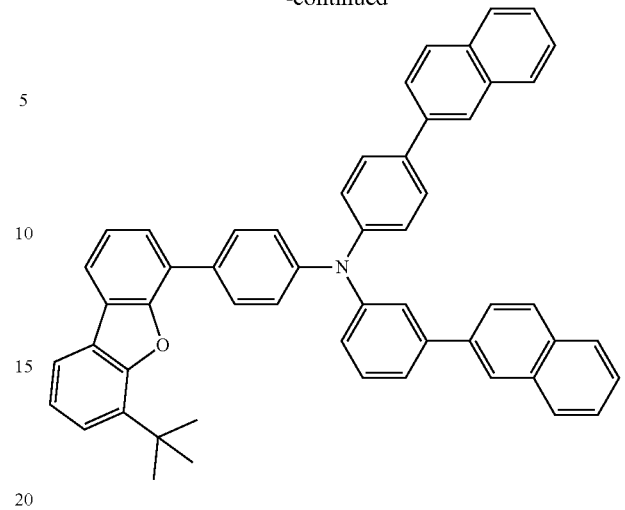
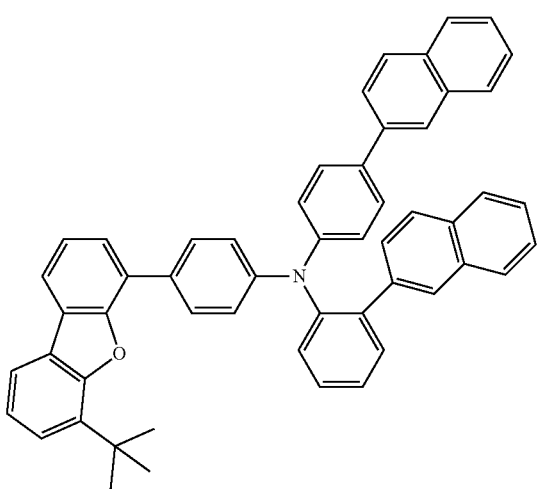
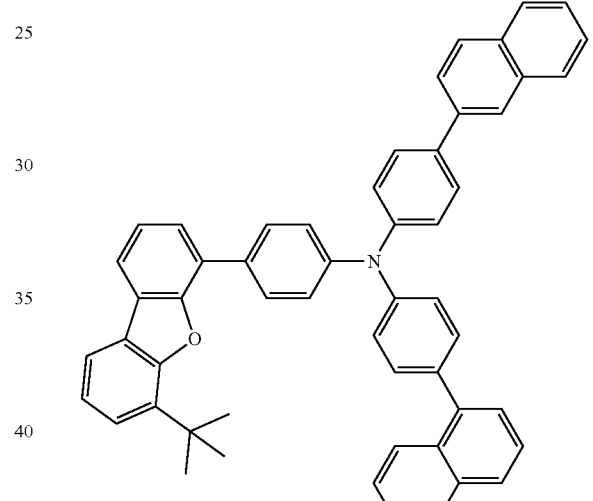
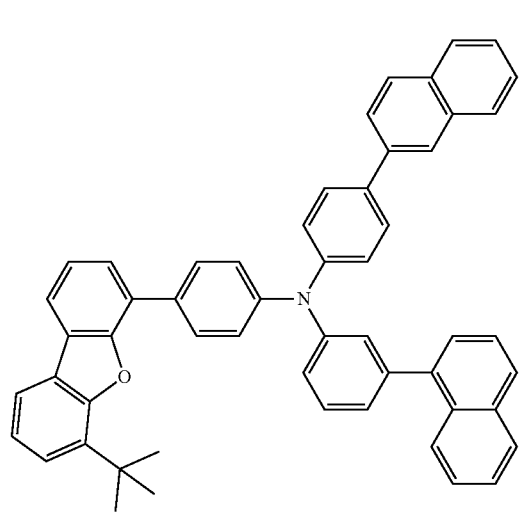
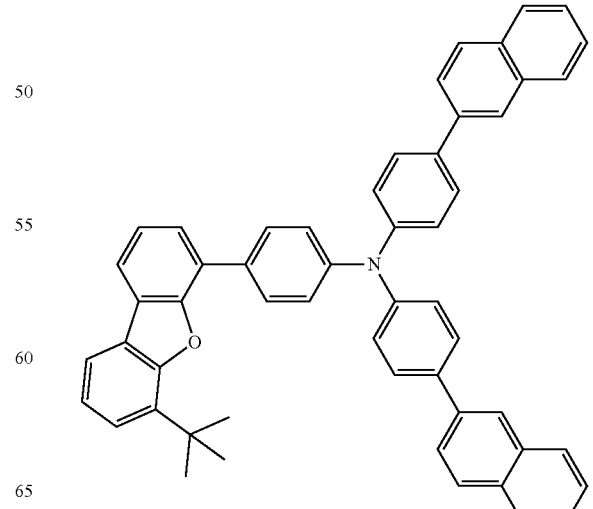

71
-continued
72
-continued
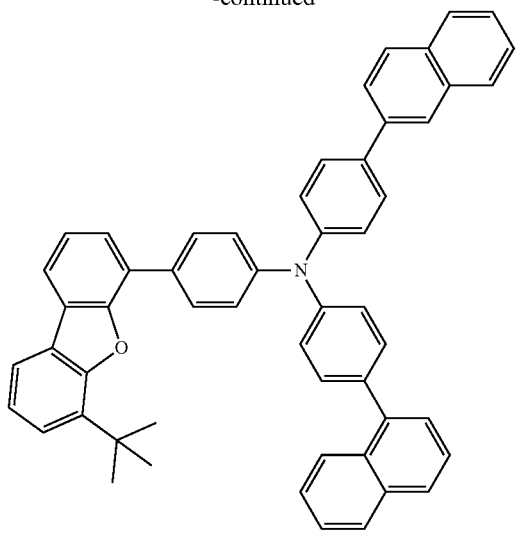
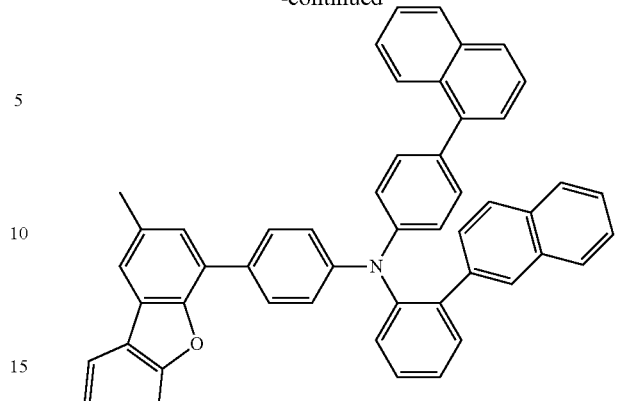
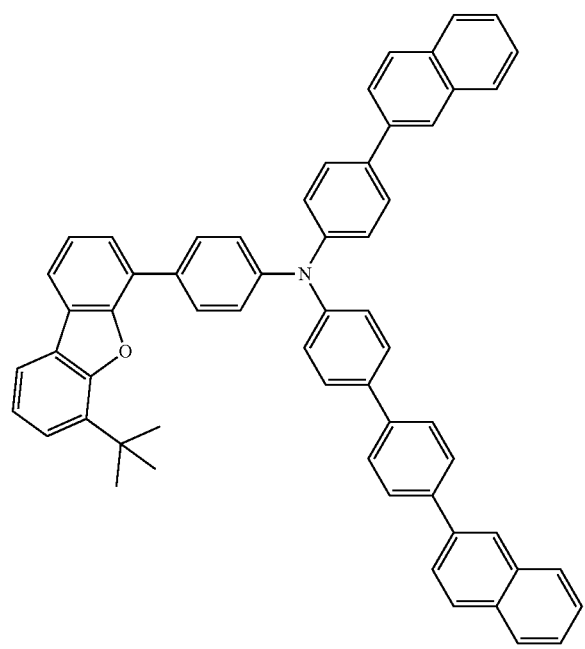
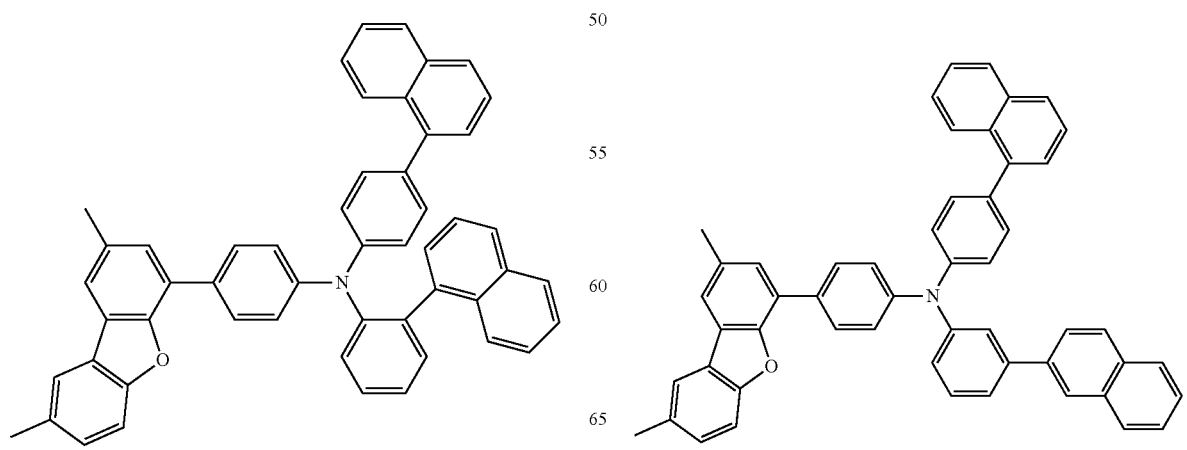

73
-continued
74
-continued
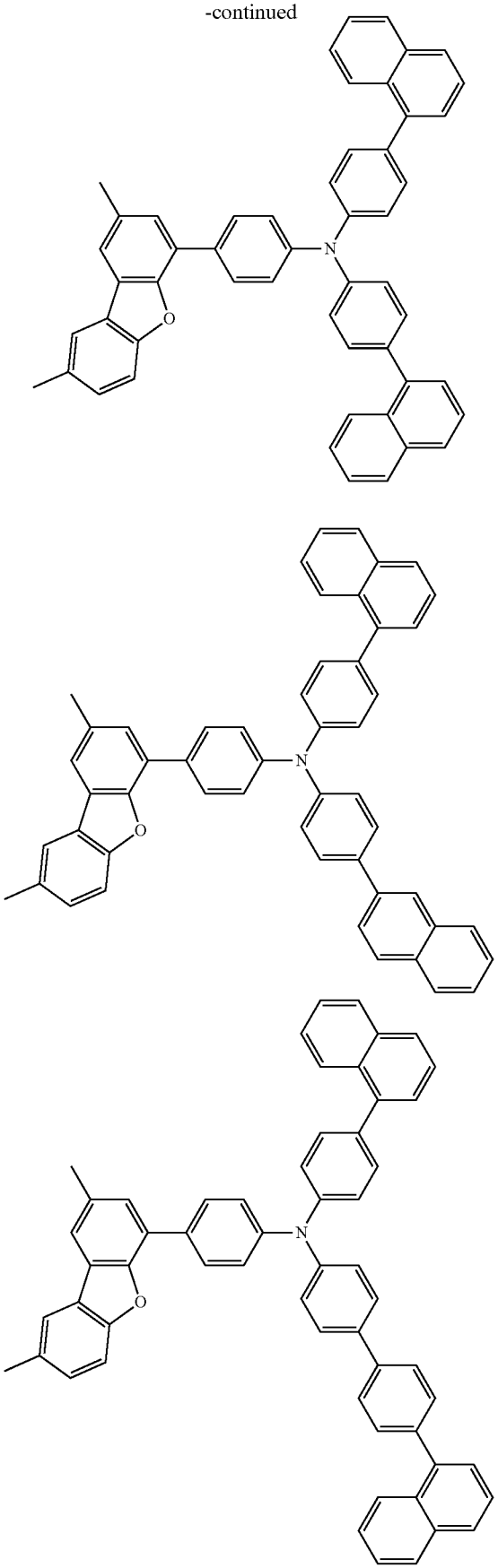
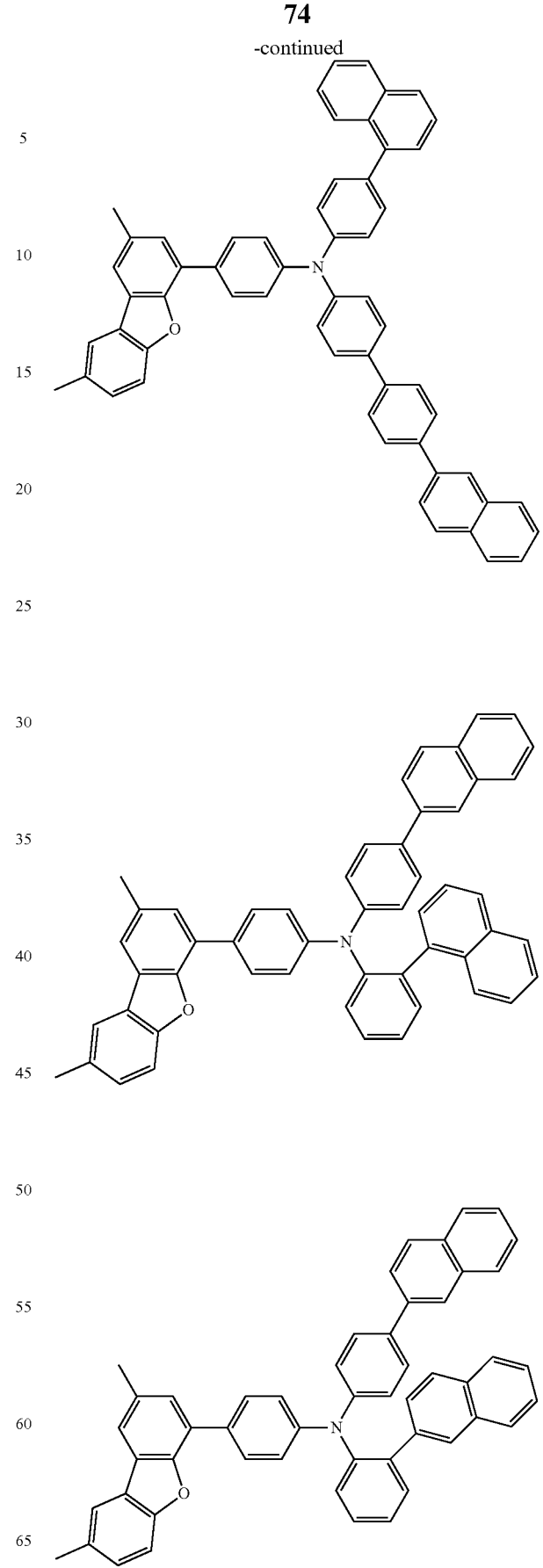

75
-continued
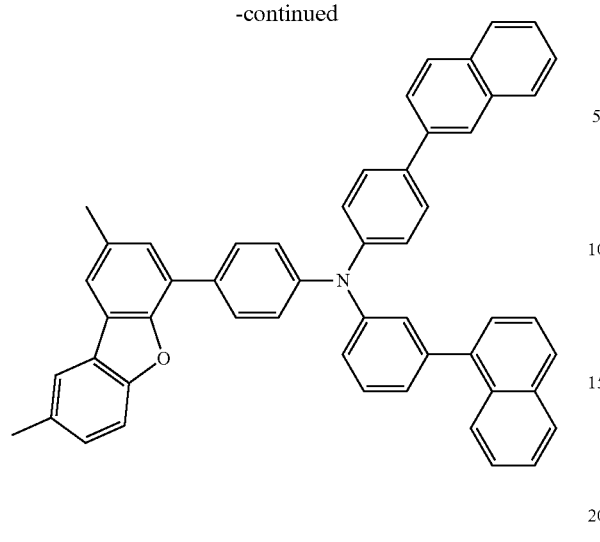
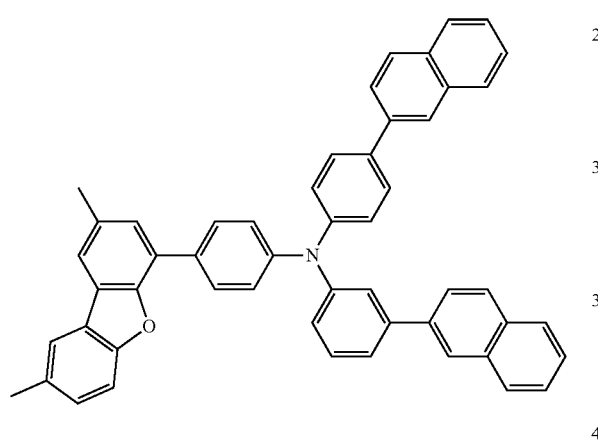
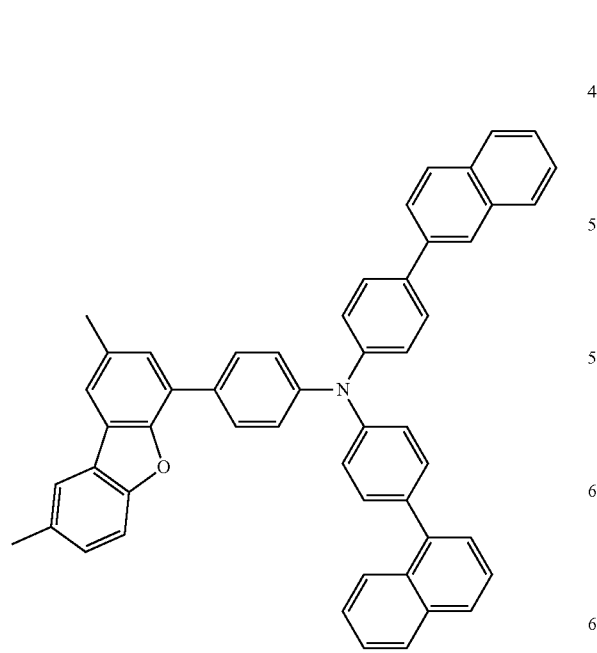
76
-continued
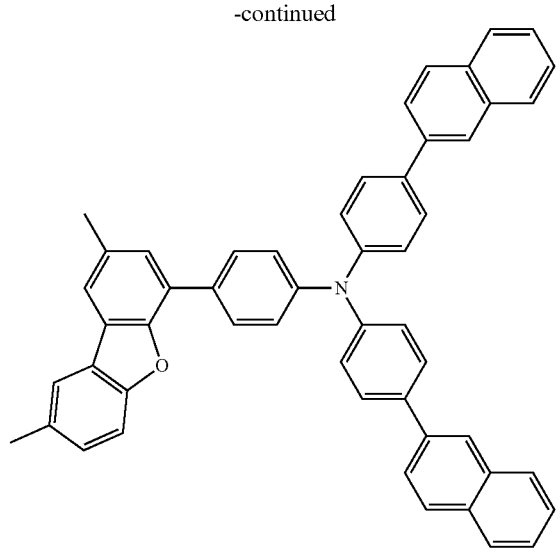
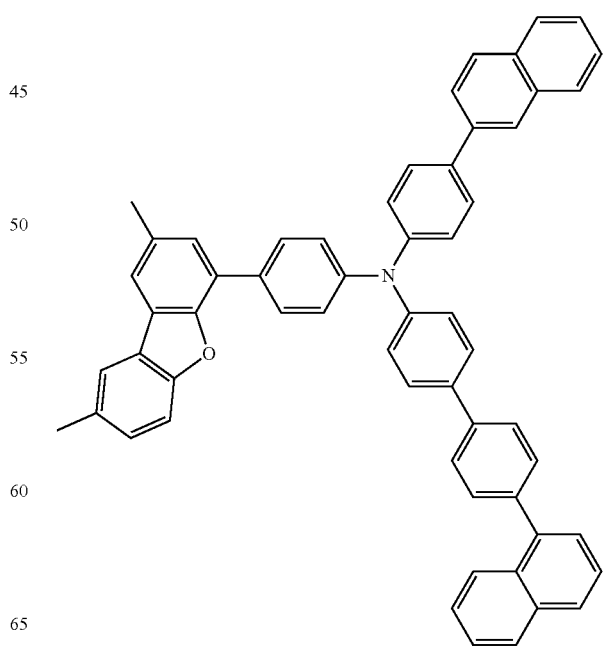

77
-continued
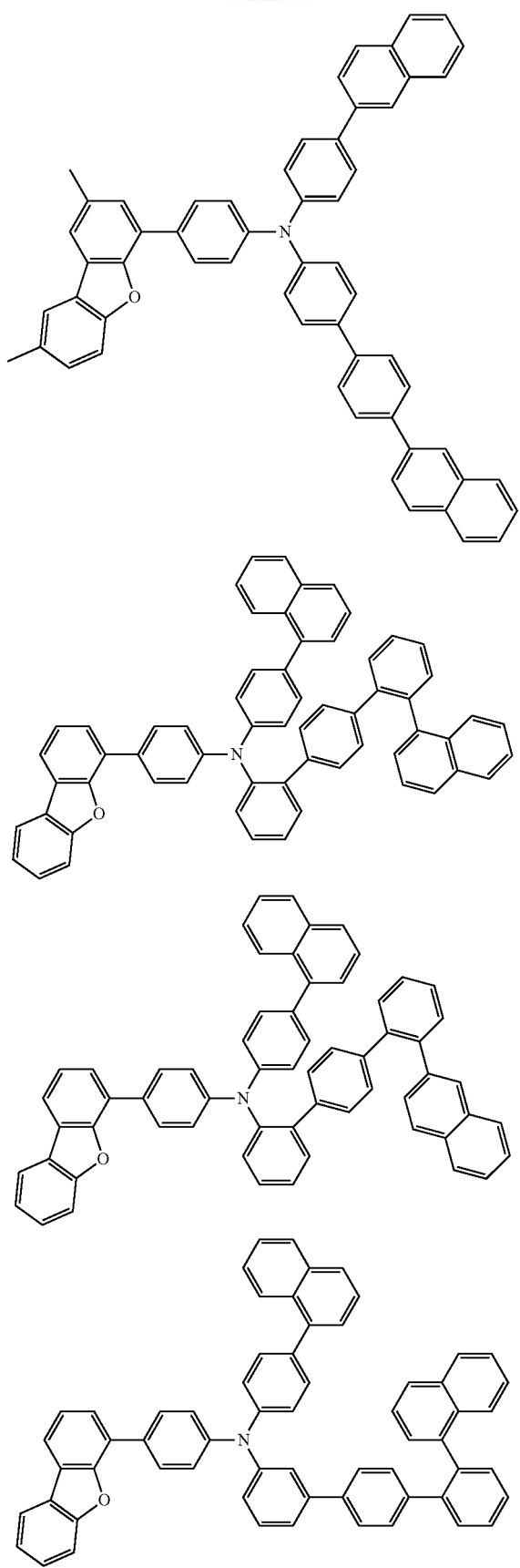
78
-continued
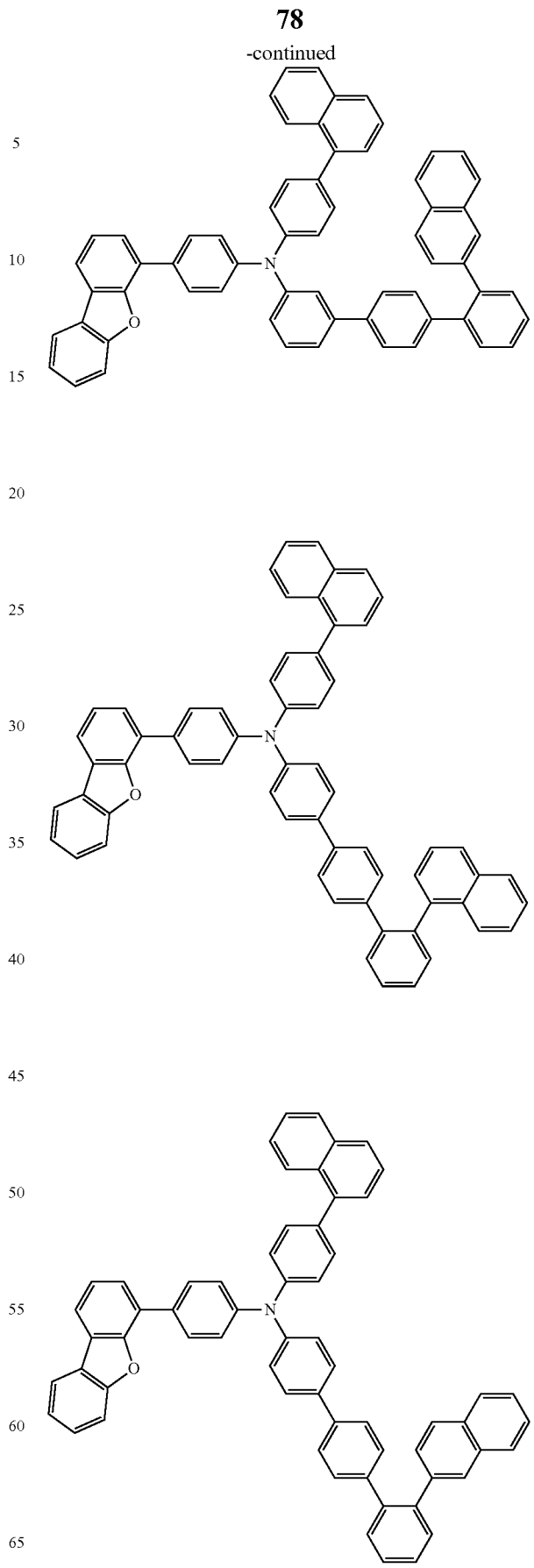

-continued
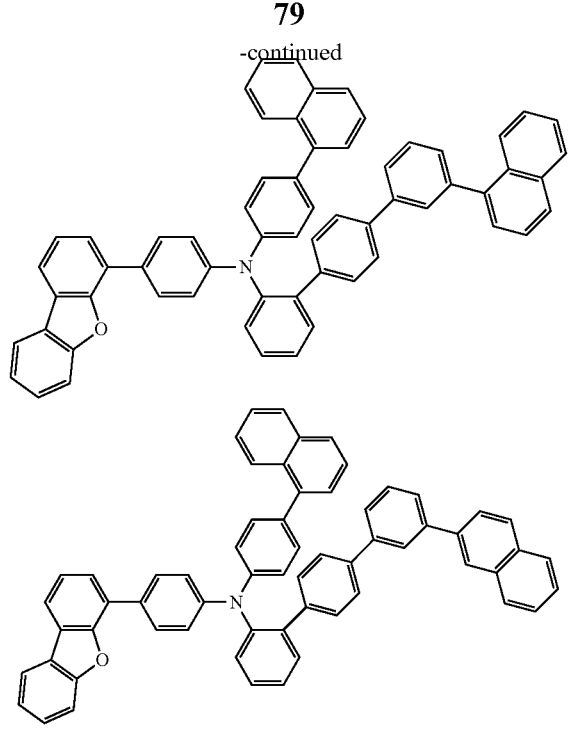
-continued
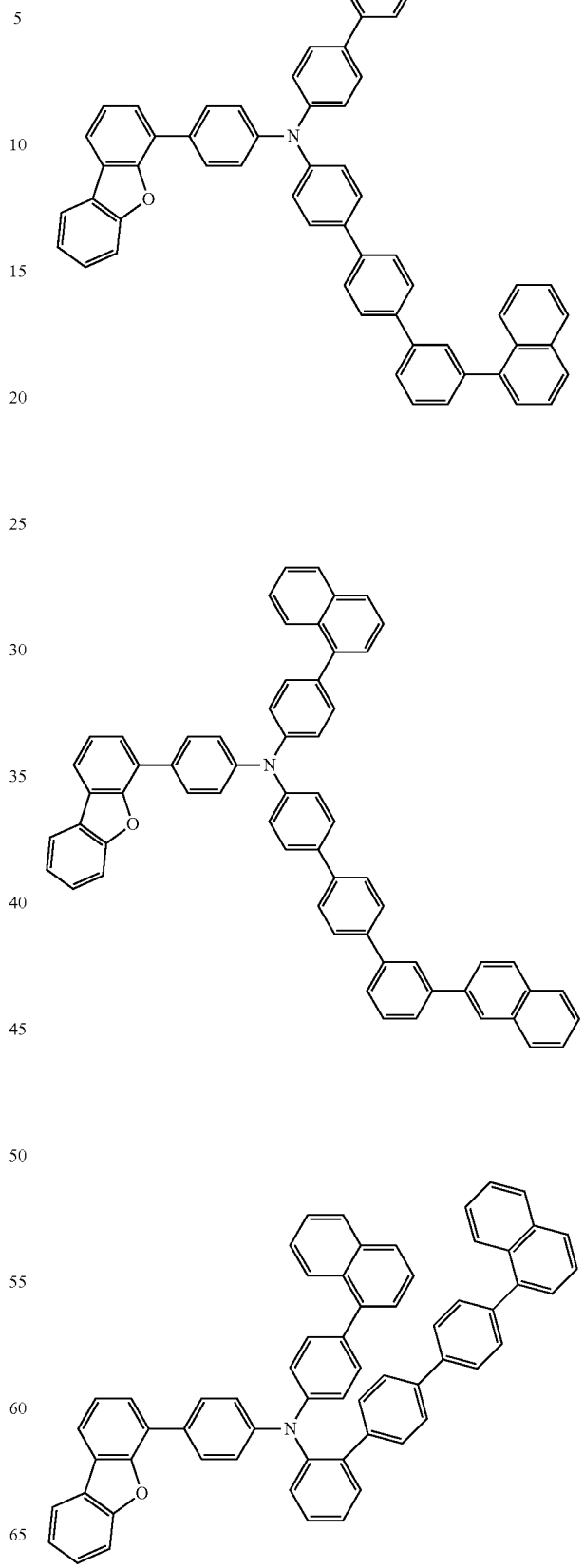

81
-continued
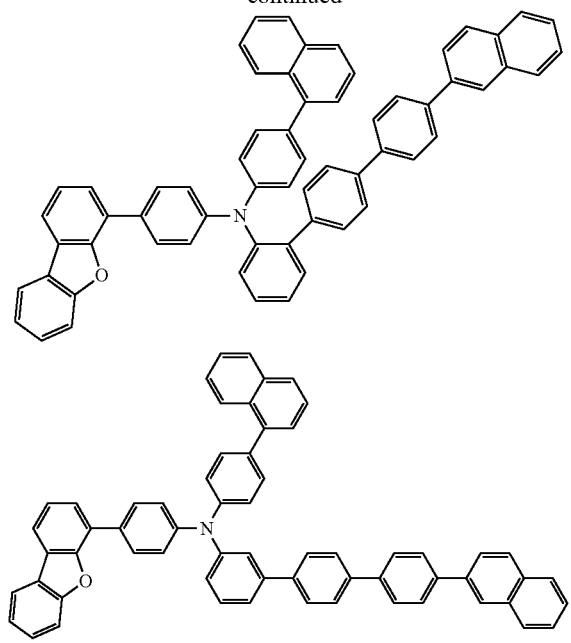
82
-continued
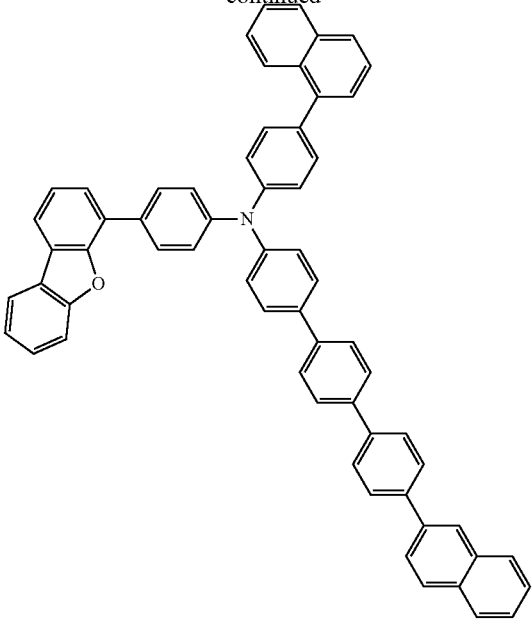
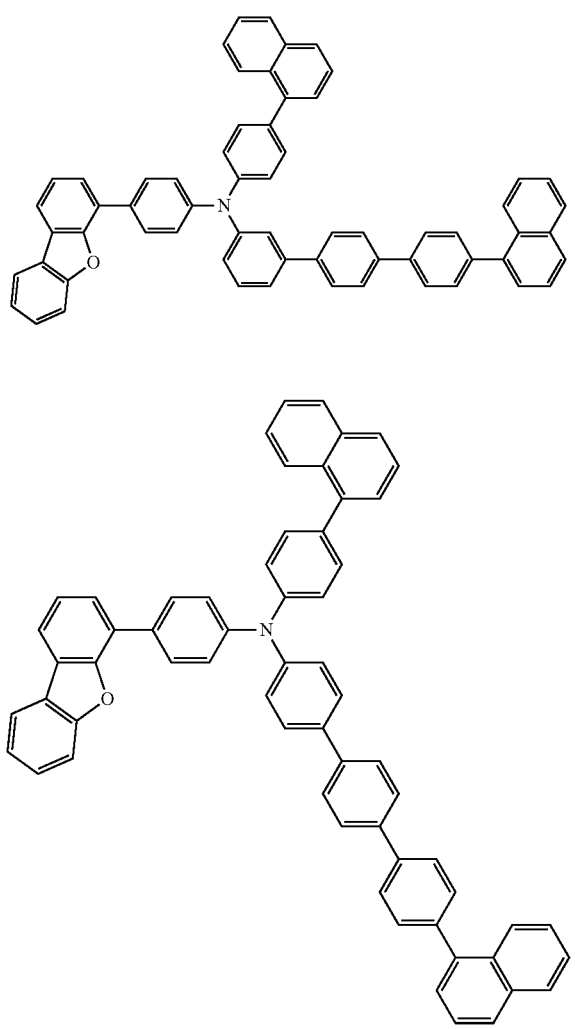
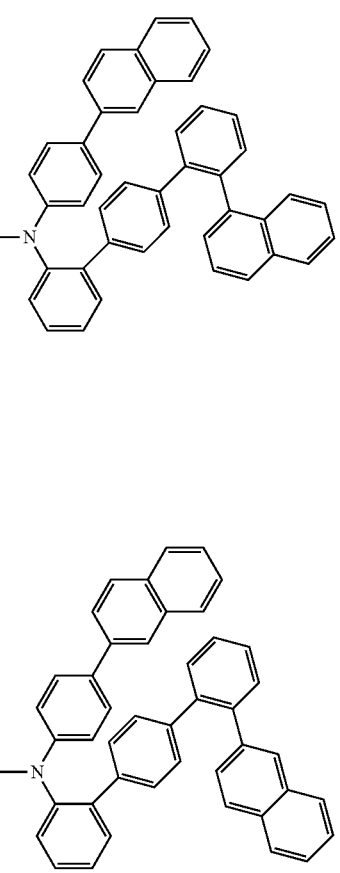

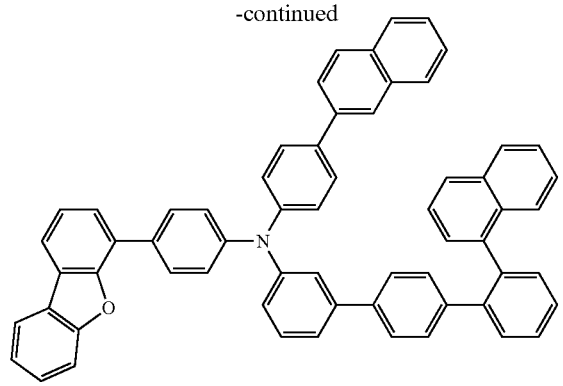
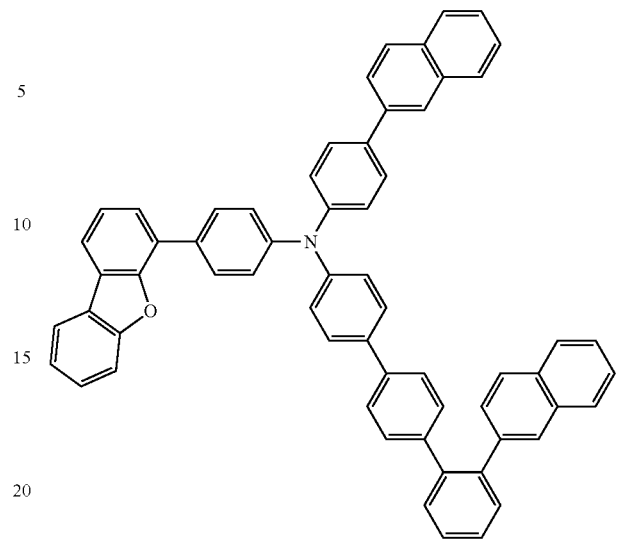
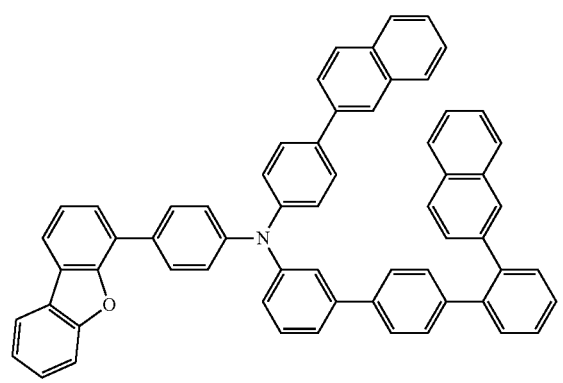
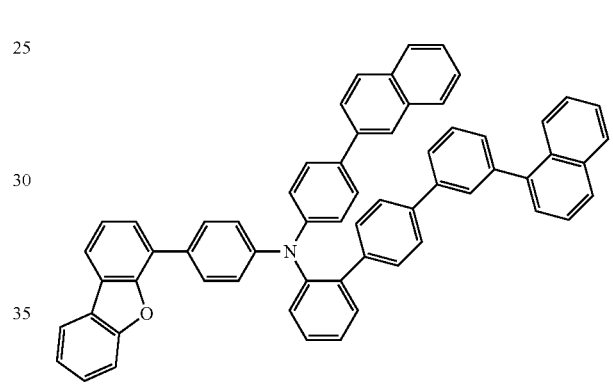
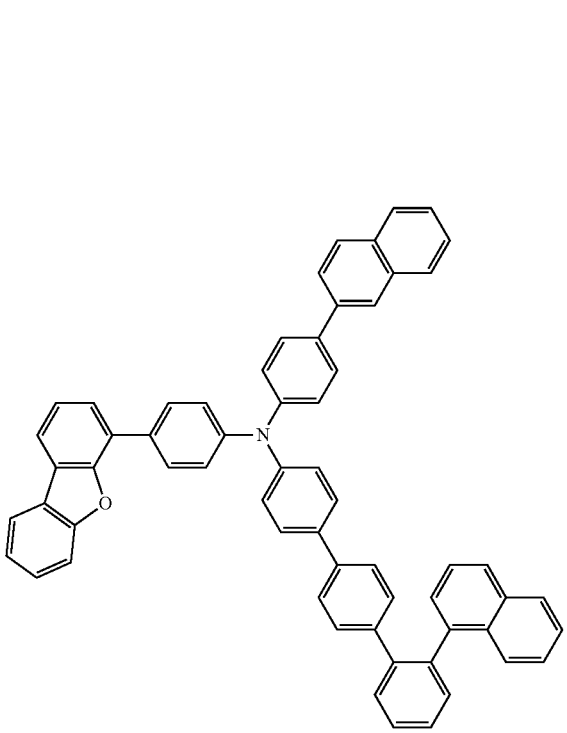
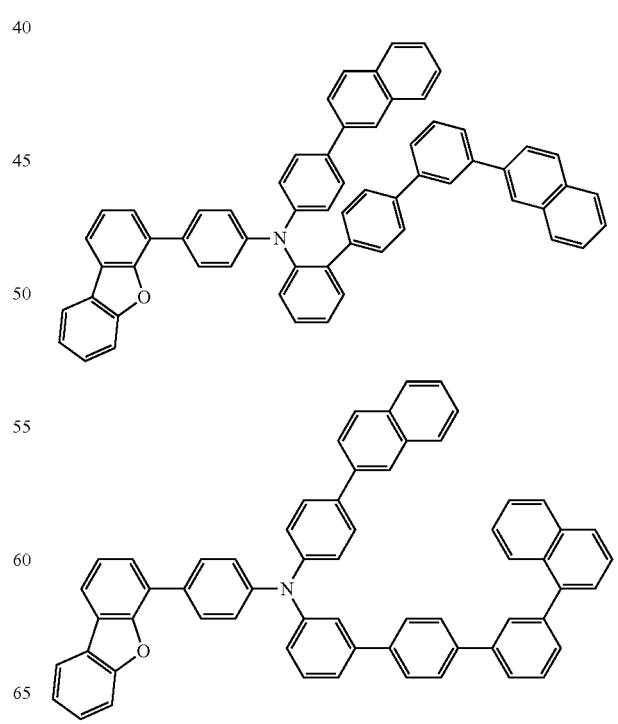

85
-continued
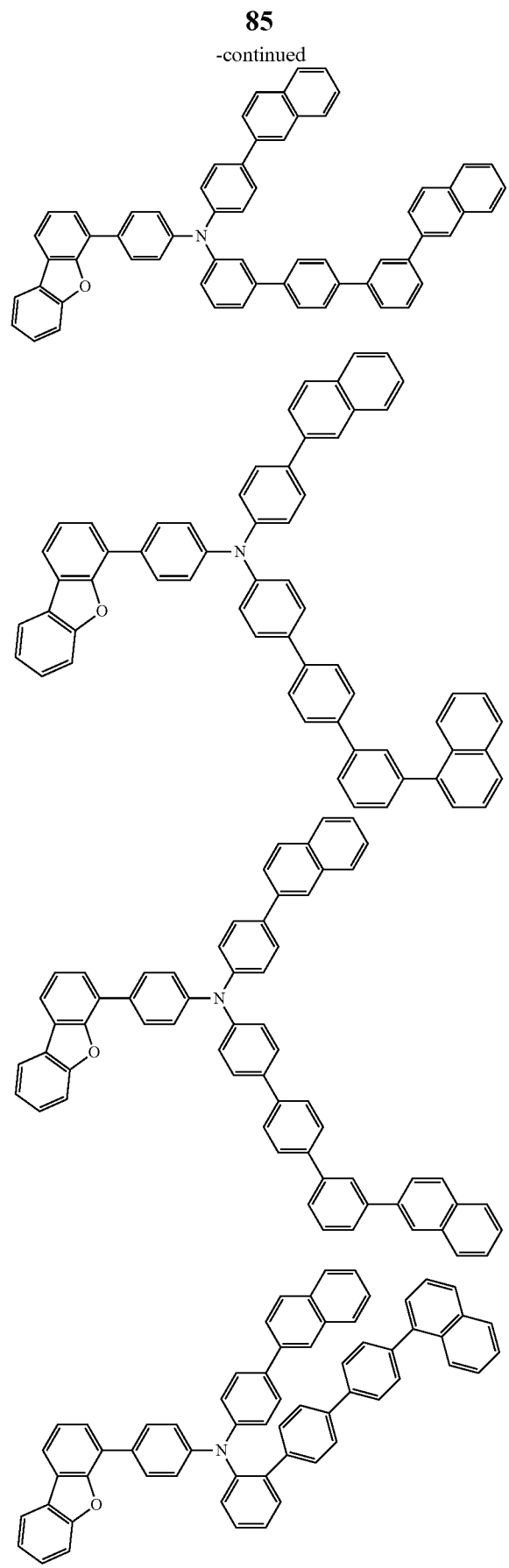
86
-continued
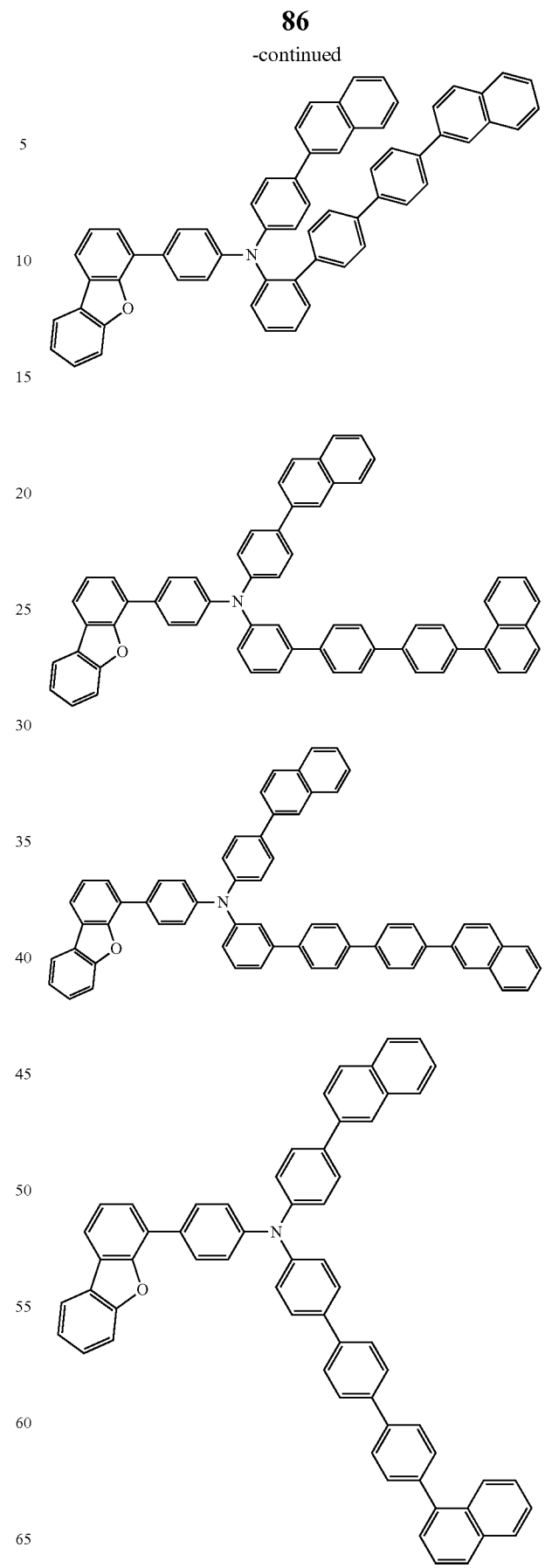

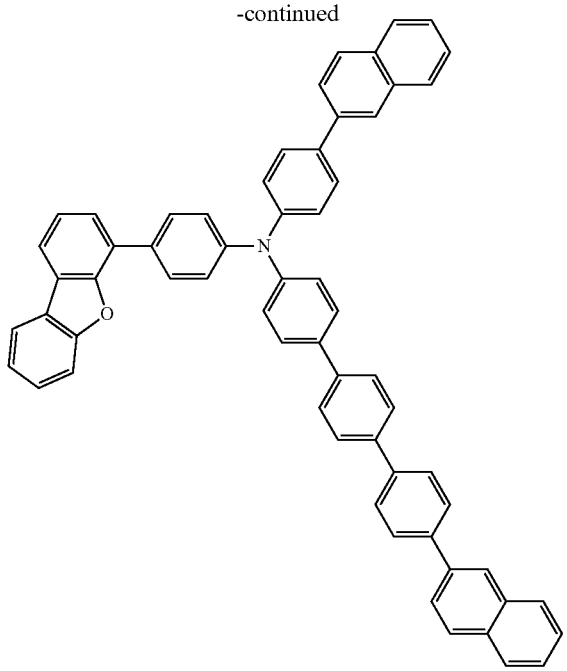

The compound (1) is useful as a material for an organic EL device, a hole transporting material, and a material for an organic layer provided between an anode and a light emitting layer, such as a hole injection layer and a hole transporting layer. The production method of the compound (1) is not particularly limited, and a person skilled in the art can easily produce the compound by using and modifying known synthesis reactions with reference to the examples in the description herein.

The organic EL device will be described below.

Representative examples of the device structure of the organic EL device include the following (1) to (13), but the structure is not particularly limited thereto. The device structure (8) is preferably used.

(1) anode/light emitting layer/cathode
(2) anode/hole injection layer/light emitting layer/cathode
(3) anode/light emitting layer/electron injection layer/cathode
(4) anode/hole injection layer/light emitting layer/electron injection layer/cathode
(5) anode/organic semiconductor layer/light emitting layer/cathode
(6) anode/organic semiconductor layer/electron blocking layer/light emitting layer/cathode
(7) anode/organic semiconductor layer/light emitting layer/adhesion improving layer/cathode
(8) anode/hole injection layer/hole transporting layer/light emitting layer/(electron transporting layer/) electron injection layer/cathode
(9) anode/insulating layer/light emitting layer/insulating layer/cathode
(10) anode/inorganic semiconductor layer/insulating layer/light emitting layer/insulating layer/cathode
(11) anode/organic semiconductor layer/insulating layer/light emitting layer/insulating layer/cathode
(12) anode/insulating layer/hole injection layer/hole transporting layer/light emitting layer/insulating layer/cathode
(13) anode/insulating layer/hole injection layer/hole transporting layer/light emitting layer/(electron transporting layer/)electron injection layer/cathode The compound (1) may be used in any of the organic layers of the organic EL device, and is preferably used in the hole injection layer or the hole transporting layer, and more preferably used in a hole transporting layer, from the standpoint of the contribution of the compound to the enhancement of the external quantum efficiency and the lifetime.

The content of the compound (1) in the organic layer, preferably the hole injection layer or the hole transporting layer, is preferably 30 to 100% by mol, more preferably 50 to 100% by mol, further preferably 80 to 100% by mol, and particularly preferably substantially 100% by mol, based on the total molar amount of the organic layer.

The layers of the organic EL device using the compound (1) in the hole injection layer and the hole transporting layer will be described below for example.

(Substrate)

The substrate is used as a support of the organic EL device. Examples of the substrate include plates of glass, quartz, and plastics. The substrate may be a flexible substrate. The flexible substrate means a foldable substrate, and examples thereof include plastic substrates formed of polycarbonate, polyarylate, polyether sulfone, polypropylene, polyester, polyvinyl fluoride, and polyvinyl chloride. An inorganic vapor-deposition film may also be used.

(Anode)

The anode formed on the substrate is preferably a metal, an alloy, a conductive compound, and a mixture thereof, each having a large work function (which is specifically 4.0 eV or more). Examples of the material for the anode include indium oxide-tin oxide (ITO: indium tin oxide), indium oxide-tin oxide containing silicon or silicon oxide, indium oxide-zinc oxide, indium oxide containing tungsten oxide and zinc oxide, and graphene. Examples thereof also include gold (Au), platinum (Pt), nickel (Ni), tungsten (W), chromium (Cr), molybdenum (Mo), iron (Fe), cobalt (Co), copper (Cu), palladium (Pd), titanium (Ti), and nitrides of these metals (such as titanium nitride).

The material may be formed into a film generally by a sputtering method. For example, indium oxide-zinc oxide can be formed by using a target containing indium oxide having 1 to 10% by weight of zinc oxide added thereto, and indium oxide containing tungsten oxide and zinc oxide can be formed by using a target containing indium oxide containing 0.5 to 5% by weight of tungsten oxide and 0.1 to 1% by weight of zinc oxide, by the sputtering method. The anode may also be formed by a vacuum vapor deposition method, a coating method, an ink-jet method, a spin coating method, and the like.

A hole injection layer formed in contact with the anode is formed of a material capable of readily injecting holes irrespective of the work function of the anode, and therefore, the anode may be formed of a material that is generally used as an electrode material (such as a metal, an alloy, an electroconductive compound, a mixture thereof, and an element of the group 1 or 2 in the periodic table).

Elements of the groups 1 and 2 in the periodic table i.e., an alkali metal, such as lithium (Li) and cesium (Cs), an alkaline earth metal, such as magnesium (Mg), calcium (Ca), and strontium (Sr), and an alloy containing them (such as MgAg and AlLi), and a rare earth metal, such as europium (Eu) and ytterbium (Yb), and an alloy containing them, which are materials having a small work function, may also be used. In the case where the anode is formed by using an alkali metal, an alkaline earth metal, or an alloy containing them, a vacuum vapor deposition or a sputtering method may be used. In the case where a silver paste or the like is used, a coating method, an ink-jet method, or the like may be used.

(Hole Injection Layer)

The hole injection layer is a layer containing a material having a high hole injection capability. The compound (1) may be used in the hole injection layer, alone or as a combination with the following compounds.

Examples of the material having a high hole injection capability used include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Examples of the hole injection layer material also include aromatic compounds, which are low molecular weight compounds, for example,
4,4',4''-tris(N,N-diphenylamino)triphenylamine (abbr: TDATA),
4,4',4''-tris[N-(3-methylphenyl)-N-phenylamino]triphenylamine (abbr: MTDATA),
4,4'-bis[N-(4-diphenylaminophenyl)-N-phenylamino]biphenyl (abbr: DPAB),
4,4'-bis(N-{4-[N'-(3-methylphenyl-N'-phenylamino]phenyl}-N-phenylamino)biphenyl (abbr: DNTPD),
1,3,5-tris[N-(4-diphenylaminophenyl)-N-phenylamino]benzene (abbr: DPA3B),
3-[N-(9-phenylcarbazole-3-yl)-N-phenylamino]-9-phenylcarbazole (abbr: PCzPCA1), 3,6-bis[N-(9-phenylcarbazole-3-yl)-N-phenylamino]-9-phenylcarbazole (abbr: PCzPCA2), and
3-[N-(1-naphthyl)-N-(9-phenylcarbazole-3-yl)amino]-9-phenylcarbazole (abbr: PCzPCN1).

A high molecular weight compound (such as an oligomer, a dendrimer, and a polymer) may also used. Examples of the high molecular weight compound include poly(N-vinylcarbazole) (abbr: PVK), poly(4-vinyltriphenylamine) (abbr: PVTPA),
poly[N-(4-{N'-[4-(4-diphenylamino)phenyl]phenyl-N'-phenylamino}phenyl)methacrylamide] (abbr: PTPDMA), and
poly[N,N'-bis(4-butylphenyl)-N,N'-bis(phenyl)benzidine] (abbr: Poly-TPD). A high molecular weight compound having an acid added thereto, such as poly(3,4-ethylenedioxythiophene)/poly(styrenesulfonic acid) (PEDOT/PSS) and polyaniline/poly(styrenesulfonic acid) (PAni/PSS), may also be used.

(Hole Transporting Layer)

The hole transporting layer is a layer containing a material having a high hole transporting capability. The compound (1) may be used in the hole transporting layer, alone or as a combination with the following compounds.

An aromatic compound, a carbazole derivative, an anthracene derivative, and the like may be used in the hole transporting layer. Specific examples thereof used include aromatic compounds, such as
4,4'-bis[N-(1-naphthyl)-N-phenylamino]biphenyl (abbr: NPB),
N,N'-bis(3-methylphenyl)-N,N'-diphenyl-[1,1'-biphenyl]-4,4'-diamine (abbr: TPD),
4-phenyl-4'-(9-phenylfluoren-9-yl)triphenylamine (abbr: BAFLP),
4,4'-bis[N-(9,9-dimethylfluoren-2-yl)-N-phenylamino]biphenyl (abbr: DFLDPBi), 4,4',4''-tris(N,N-diphenylamino)triphenylamine (abbr: TDATA), 4,4',4''-tris[N-(3-methylphenyl)-N-phenylamino]triphenylamine (abbr: MTDATA), and 4,4'-bis[N-(spiro-9,9'-bifluoren-2-yl)-N-phenylamino]biphenyl (abbr: BSPB). The substances described herein are substances having a hole mobility of $10^{-6}$ cm$^2$/Vs or more.

A carbazole derivative, such as CBP, CzPA, and PCzPA, and an anthracene derivative, such as t-BuDNA, DNA, and DPAnth, may also be used in the hole transporting layer. A high molecular weight compound, such as poly(N-vinylcarbazole) (abbr: PVK) and poly(4-vinyltriphenylamine) (abbr: PVTPA), may also be used.

Other materials than described herein that have a higher transporting capability for holes than that for electrons may be used. The layer containing the material having a high hole transporting capability may be not only a single layer but also two or more layers laminated each formed of the aforementioned substance. For example, the hole transporting layer may have a two-layer structure including a first hole transporting layer (on the side of the anode) and a second hole transporting layer (on the side of the cathode). In this case, the compound (1) may be contained in any of the first hole transporting layer and the second hole transporting layer, and is preferably contained in the second hole transporting layer disposed on the side of the light emitting layer (i.e., the side of the cathode) from the standpoint of facilitating the exhibition of the effects of the present invention.

(Guest Material of Light Emitting Layer)

The light emitting layer is a layer containing a substance having a high light emission capability (i.e., a guest material), and various materials may be used therein. For example, a fluorescent compound or a phosphorescent compound may be used as the guest material. The fluorescent compound is a compound capable of emitting light from a singlet excited state, and the phosphorescent compound is a compound capable of emitting light from a triplet excited state.

Examples of the blue fluorescent light emitting material that can be used in the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N,N'-diphenylstilbene-4,4'-diamine (abbr: YGA2S), 4-(9H-carbazole-9-yl)-4'-(10-phenyl-9-anthryl)triphenylamine (abbr: YGAPA), and
4-(10-phenyl-9-anthryl)-4'-(9-phenyl-9H-carbazole-3-yl)triphenylamine (abbr: PCBAPA).

Examples of the green fluorescent light emitting material that can be used in the light emitting layer include an aromatic amine derivative. Specific examples thereof include
N-(9,10-diphenyl-2-anthryl)-N,9-diphenyl-9H-carbazole-3-amine (abbr: 2PCAPA),
N-[9,10-bis(1,1'-biphenyl-2-yl)-2-anthryl]-N,9-diphenyl-9H-carbazole-3-amine (abbr: 2PCABPhA),
N-(9,10-diphenyl-2-anthryl)-N,N',N'-triphenyl-1,4-phenylenediamine (abbr: 2DPAPA),
N-[9,10-bis(1,1'-biphenyl-2-yl)-2-anthryl]-N,N',N'-triphenyl-1,4-phenylenediamine (abbr: 2DPABPhA),
N-[9,10-bis(1,1'-biphenyl-2-yl)]-N-[4-(9H-carbazole-9-yl)phenyl]-N-phenylanthracene-2-amine (abbr: 2YGABPhA), and N,N,9-triphenylanthracene-9-amine (abbr: DPhAPhA).

Examples of the red fluorescent light emitting material that can be used in the light emitting layer include a tetracene derivative and a diamine derivative. Specific examples thereof include
N,N,N',N'-tetrakis(4-methylphenyl)tetracene-5,11-diamine (abbr: p-mPhTD) and 7,14-diphenyl-N,N,N',N'- tetrakis(4-methylphenyl)acenaphtho[1,2-a]fluoranthene-3,10-diamine (abbr: p-mPhAFD).

Examples of the blue phosphorescent light emitting material that can be used in the light emitting layer include a metal complex, such as an iridium complex, an osmium complex, and a platinum complex. Specific examples thereof include bis[2-(4',6'-difluorophenyl)pyridinato-N,C2']iridium(III) tetrakis(1-pyrazolyl)borato (abbr: FIr6), bis[2-(4',6'-difluorophenyl)pyridinato-N,C2']iridium(III) picolinato (abbr: FIrpic), bis[2-(3',5'-bistrifluoromethylphenyl)pyridinato-N,C2']iridium(III) picolinato (abbr: Ir(CF3ppy)2(pic)), and bis[2-(4',6'-difluorophenyl)pyridinato-N,C2']iridium(III) acetylacetonato (abbr: FIracac).

Examples of the green phosphorescent light emitting material that can be used in the light emitting layer include an iridium complex. Specific examples thereof include tris(2-phenylpyridinato-N,C2')iridium(III) (abbr: Ir(ppy)3), bis(2-phenylpyridinato-N,C2')iridium(III) acetylacetonato (abbr: Ir(ppy)2(acac)), bis(1,2-diphenyl-1H-benzimidazolato)iridium(III) acetylacetonato (abbr: Ir(pbi)2(acac)), and bis(benzo[h]quinolinato)iridium(III) acetylacetonato (abbr: Ir(bzq)2(acac)).

Examples of the red phosphorescent light emitting material that can be used in the light emitting layer include a metal complex, such as an iridium complex, a platinum complex, a terbium complex, and a europium complex. Specific examples thereof include an organometallic complex, such as bis[2-(2'-benzo[4,5-α]thienyl)pyridinato-N,C3']iridium(III) acetylacetonato (abbr: Ir(btp)2(acac)), bis(1-phenylisoquinolinato-N,C2')iridium(III) acetylacetonato (abbr: Ir(piq)2(acaa)), (acetylacetonato)bis[2,3-bis(4-fluorophenyl)quinoxalinato]iridium(III) (abbr: Ir(Fdpq)2(acac)), and 2,3,7,8,12,13,17,18-octaethyl-21H,23H-porphyrin platinum(II) (abbr: PtOEP).

A rare earth metal complex, such as tris(acetylacetonato)(monophenanthroline)terbium(III) (abbr: Tb(acac)3(Phen)), tris (1,3-diphenyl-1,3-propanedionato)(monophenanthroline)europium(III) (abbr: Eu(DBM)3(Phen)), and tris[1-(2-thenoyl)-3,3,3-trifluoroacetonato](monophenanthroline)europium(III) (abbr: Eu(TTA)3(Phen)), emits light from the rare earth metal ion (i.e., the electron transition between different multiplicities), and therefore can be used as the phosphorescent compound.

(Host Material of Light Emitting Layer)

The light emitting layer may have a structure having the aforementioned guest material dispersed in another substance (i.e., a host material). Various materials may be used as the host material, and a substance that has a higher lowest unoccupied molecular orbital level (LUMO level) and a lower highest occupied molecular orbital level (HOMO level) than the guest material is preferably used.

Examples of the host material used include:
(1) a metal complex, such as an aluminum complex, a beryllium complex, and a zinc complex;
(2) a heterocyclic compound, such as an oxadiazole derivative, a benzimidazole derivative, and a phenanthroline derivative;
(3) a condensed aromatic compound, such as a carbazole derivative, an anthracene derivative, a phenanthrene derivative, a pyrene derivative, and a chrysene derivative; and
(4) an aromatic compound, such as a triarylamine derivative and a condensed aromatic polycyclic amine derivative.

Specific examples thereof used include: a metal complex, such as tris(8-quinolinolato)aluminum(III) (abbr: Alq), tris(4-methyl-8-quinolinolato)aluminum(III) (abbr: Almq3), bis(10-hydroxybenzo[h] quinolinato)beryllium (abbr: BeBq2), bis(2-methyl-8-quinolinolato)(4-phenylphenolato)aluminum(III) (abbr: BAlq), bis(8-quinolinolato)zinc(II) (abbr: Znq), bis[2-(2-benzoxazolyl)phenolato]zinc(II) (abbr: ZnPBO), and bis[2-(2-benzothiazolyl)phenolato]zinc(II) (abbr: ZnBTZ); a heterocyclic compound, such as 2-(4-biphenylyl)-5-(4-tert-butylphenyl)-1,3,4-oxadiazole (abbr: PBD), 1,3-bis[5-(p-tert-butylphenyl)-1,3,4-oxadiazole-2-yl]benzene (abbr: OXD-7), 3-(4-biphenylyl)-4-phenyl-5-(4-tert-butylphenyl)-1,2,4-triazole (abbr: TAZ), 2,2',2"-(1,3,5-benzenetriyl)tris(1-phenyl-1H-benzimidazole) (abbr: TPBI), bathophenanthroline (abbr: BPhen), and bathocuproine (abbr: BCP); a condensed aromatic compound, such as 9-[4-phenyl-9-anthryl)phenyl]-9H-carbazole (abbr: CzPA), 3,6-diphenyl-9-[4-(10-phenyl-9-anthryl)phenyl]-9H-carbazole (abbr: DPCzPA), 9,10-bis(3,5-diphenylphenyl)anthracene (abbr: DPPA), 9,10-di(2-naphthyl)anthracene (abbr: DNA), 2-tert-butyl-9,10-di(2-naphthyl)anthracene (abbr: t-BuDNA), 9,9'-bianthryl (abbr: BANT), 9,9'-(stilbene-3,3'-diyl)diphenanthrene (abbr: DPNS), 9,9'-(stilbene-4,4'-diyl)diphenanthrene (abbr: DPNS2), 3,3',3"-(benzene-1,3,5-triyl)tripyrene (abbr: TPB3), 9,10-diphenylanthracene (abbr: DPAnth), and 6,12-dimethoxy-5,11-diphenylchrysene; and an aromatic compound, such as N,N-diphenyl-9-[4-(10-phenyl-9-anthryl)phenyl]-9H-carbazole-3-amine (abbr: CzA1PA), 4-(10-phenyl-9-anthryl) triphenylamine (abbr: DPhPA), N,9-diphenyl-N-[4-(10-phenyl-9-anthryl)phenyl3]-9H-carbazole-3-amine (abbr: PCAPA), N,9-diphenyl-N-{4-[4-(10-phenyl-9-anthryl)phenyl]phenyl}-9H-carbazole-3-amine (abbr: PCAPBA), N-(9,10-diphenyl-2-anthryl)-N,9-diphenyl-9H-carbazole-3-amine (abbr: 2PCAPA), NPB (or α-NPD), TPD, DFLDPBi, and BSPB. Plural kinds of the host materials may be used.

(Electron Transporting Layer)

The electron transporting layer is a layer containing a substance having a high electron transporting capability. The electron transporting layer may contain:
(1) a metal complex, such as an aluminum complex, a beryllium complex, and a zinc complex;
(2) an aromatic heterocyclic compound, such as an imidazole derivative, a benzimidazole derivative, an azine derivative, a carbazole derivative, and a phenanthroline derivative; and
(3) a high molecular weight compound.

Specific examples thereof used include a metal complex as a low molecular weight organic compound, such as Alq, tris(4-methyl-8-quinolinolato)aluminum (abbr: Almq3), bis(10-hydroxybenzo[h]quinolinato)beryllium (abbr: BeBq$_2$), BAlq, Znq, ZnPBO, and ZnBTZ. In addition to the metal complex, an aromatic heterocyclic compound may be used, examples of which include 2-(4-biphenylyl)-5-(4-tert-butylphenyl)-1,3,4-oxadiazole (abbr: PBD), 1,3-bis[5-(p-tert-butylphenyl)-1,3,4-oxadiazole-2-yl]benzene (abbr: OXD-7), 3-(4-tert-butylphenyl)-4-phenyl-5-(4-biphenylyl)-1,2,4-triazole (abbr: TAZ), 3-(4-tert-butylphenyl)-4-(4-ethylphenyl)-5-(4-biphenylyl)-1,2,4-triazole (abbr: p-EtTAZ), bathophenanthroline (abbr: BPhen), bathocuproine (abbr: BCP), and 4,4'-bis(5-methylbenzoxazole-2-yl)stilbene (abbr: BzOs). These materials are mainly materials having an electron mobility of $101^{-6}$ cm$^2$/Vs or more. Other materials than described herein that have a higher electron transporting capability than that than the hole transporting capability may also be used. The electron transporting layer may be not only a single layer but also two or more layers each formed of the aforementioned material laminated.

A high molecular weight compound may also be used in the electron transporting layer, examples of which include poly[(9,9-dihexylfluorene-2,7-diyl)-co-(pyridine-3,5-diyl)] (abbr: PF-Py) and poly[(9,9-dioctylfluorene-2,7-diyl)-co-(2,2'-bipyridine-6,6'-diyl)] (abbr: PF-BPy).

(Electron Injection Layer)

The electron injection layer is a layer containing a substance having a high electron injection capability. The electron injection layer may contain an alkali metal, an alkaline earth metal, or a compound thereof, such as lithium (Li), cesium (Cs), calcium (Ca), lithium fluoride (LiF), cesium fluoride (CsF), calcium fluoride (CaF$_2$), and lithium oxide (LiO$_x$). In addition, a material having an electron transporting capability containing an alkali metal, an alkaline earth metal, or a compound thereof, specifically Alq containing magnesium (Mg), may also be used. In this case, the electron injection from the cathode can be performed with high efficiency.

A composite material obtained by mixing an organic compound and an electron donor may also be used in the electron injection layer. The composite material is excellent in the electron injecting capability and the electron transporting capability since the organic compound receives electrons from the electron donor. In this case, the organic compound is preferably a compound excellent in transporting the received electrons, and specifically the material constituting the electron transporting layer described above (such as a metal complex and a heterocyclic aromatic compound) may be used. It suffices that the electron donor is a material that exhibits an electron donating capability to the organic compound. Specifically, an alkali metal, an alkaline earth metal, and a rare earth metal are preferred, and examples thereof include lithium, cesium, magnesium, calcium, erbium, and ytterbium. An alkali metal oxide and an alkaline earth metal oxide are also preferred, and examples thereof include a lithium oxide, a calcium oxide, and a barium oxide. A Lewis base, such as magnesium oxide, may also be used. An organic compound, such as tetrathiafulvalene (abbr: TTF), may also be used.

(Cathode)

The cathode is preferably formed of a metal, an alloy, a conductive compound, or a mixture thereof, each having a small work function (specifically 3.8 eV or less). Specific examples of the cathode material include an element of the group 1 or 2 in the periodic table, for example, an alkali metal, such as lithium (Li) and cesium (Cs), an alkaline earth metal, such as magnesium (Mg), calcium (Ca), and strontium (Sr), an alloy containing them (such as MgAg and AlLi), a rare earth metal, such as europium (Eu) and ytterbium (Yb), and an alloy containing the same.

In the case where the cathode is formed by using an alkali metal, an alkaline earth metal, or an alloy containing them, a vacuum vapor deposition or a sputtering method may be used. In the case where a silver paste or the like is used, a coating method, an ink-jet method, or the like may be used.

In the case where the electron injecting layer is formed, the cathode may be formed by using various conductive materials irrespective of the extent of the work function, such as Al, Ag, ITO, graphene, and indium oxide-tin oxide containing silicon or silicon oxide. The conductive materials may be formed into a film by a sputtering method, an inkjet method, a spin coating method, or the like.

(Insulating Layer)

In the organic EL device, an electric field is applied to the ultrathin films thereof, and therefore pixel defects tend to occur due to leakage and short circuit. For the prevention thereof, an insulating layer formed of a thin film layer having insulating property may be inserted between a pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture and a laminate of these materials may also be used.

A protective layer may be provided on the surface of the organic EL device, and the organic EL device may be protected with a silicon oil, a resin, or the like, from the standpoint of the enhancement of the stability of the organic EL device against the temperature, the humidity, the environment, and the like.

The layers of the organic EL device may be formed by any method of a dry film forming method, such as vacuum vapor deposition, sputtering, plasma, and ion plating, and a wet film forming method, such as spin coating, dipping and flow coating.

In the wet film forming method, the materials forming each of the layers are dissolved or dispersed in a suitable solvent, such as ethanol, chloroform, tetrahydrofuran, or dioxane, to form a solution or a dispersion liquid, with which the thin film is formed. The solution or the dispersion may contain a resin or an additive for the enhancement of the film forming capability and the prevention of pinholes in the film. Examples of the resin include an insulating resin and a copolymer thereof, such as polystyrene, polycarbonate, polyarylate, polyester, polyamide, polyurethane, polysulfone, polymethyl methacrylate, polymethyl acrylate, and cellulose, a photoconductive resin, such as poly-N-vinylcarbazole and polysilane, and a conductive resin, such as polythiophene and polypyrrole. Examples of the additive include an antioxidant, an ultraviolet ray absorbent, and a plasticizer.

The thicknesses of the layers are not particularly limited, and may be selected to provide a good device performance. With a too large thickness, a large applied voltage may be required for providing a certain optical output, which deteriorates the efficiency. With a too small thickness, pinholes and the like may form, failing to provide a sufficient light emission luminance on application of an electric field. The thickness is generally 5 nm to 10 μm, and more preferably 10 nm to 0.2 μm.

The organic EL device obtained by using the compound (1) can be used in an electronic device, for example, a display component, such as an organic EL panel module; a display device of a television set, a mobile phone, a personal computer, and the like; and a light emitting device of an illumination device and a lighting equipment for vehicles.

EXAMPLES

The present invention will be described with reference to examples below, but the present invention is not limited thereto.

Synthesis Example 1 (Synthesis of Compound 1)

(1) Synthesis of Intermediate 1

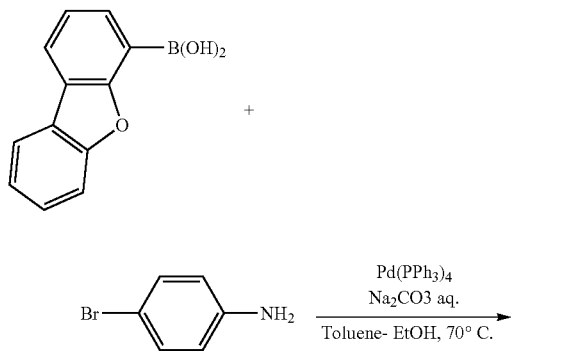

In an argon atmosphere, a mixture of 23.7 g (138 mmol) of 4-bromoaniline, 29.2 g (138 mmol) of dibenzofuran-4-yl boronate, 3.18 g (2.75 mmol) of tetrakis(triphenylphosphine) palladium(0), a 2 M sodium carbonate aqueous solution (138 mL), toluene (300 mL), and ethanol (100 mL) was agitated at 70° C. for 2 hours. After returning to room temperature, the reaction solution was extracted with toluene, and the toluene layer was dried over anhydrous magnesium sulfate, then filtered, and concentrated under reduced pressure. The resulting residue was purified by silica gel column chromatography and recrystallization to provide an intermediate 1 (20.9 g). The yield was 58%.

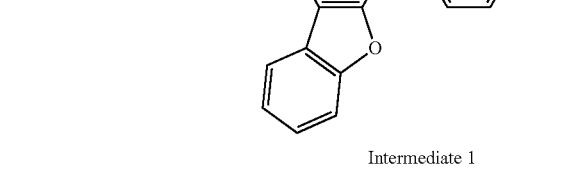

Intermediate 1

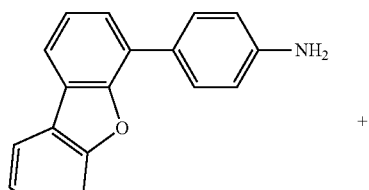

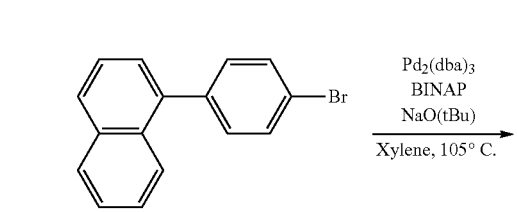

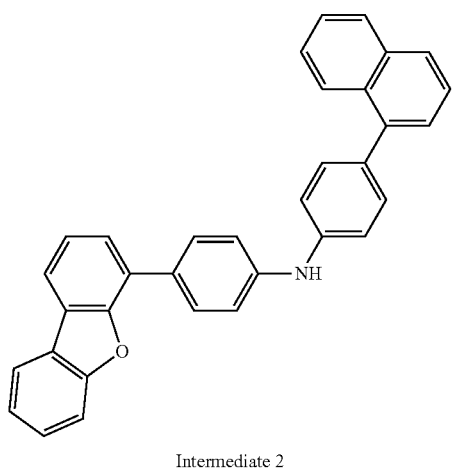

Intermediate 2

In an argon atmosphere, a solution of 20.9 g (80.6 mmol) of the intermediate 1 and 17.6 g (62 mmol) of 1-(4-bromophenyl)naphthalene in xylene (350 mL) was heated to 85° C., to which 852 mg (0.93 mmol) of tris(dibenzylideneacetone) dipalladium(0), 1.16 g (1.86 mmol) of 2,2'-bis(diphenylphosphino)-1,1'-binaphthyl, and 11.9 g (124 mmol) of sodium t-butoxide were added, and the mixture was heated to 105° C., followed by agitating for 16 hours. After returning to room temperature, water was added to the reaction liquid, the mixture was separated, the organic layer was concentrated under reduced pressure and then purified by column chromatography to provide an intermediate 2 (17.8 g). The yield was 60%.

(3) Synthesis of Compound 1

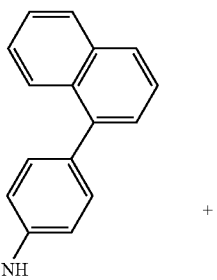

Intermediate 2

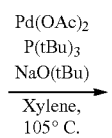

-continued

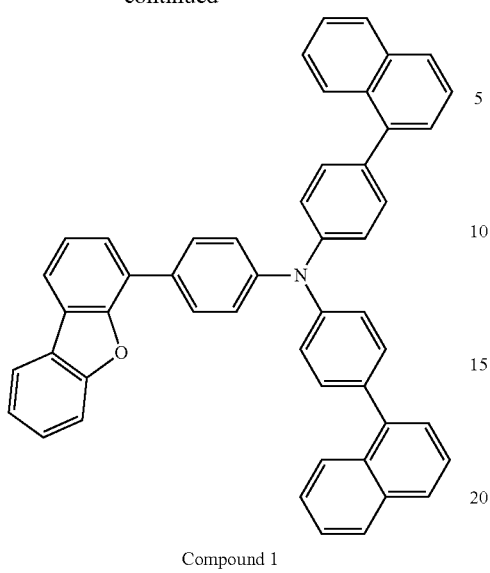

Compound 1

In an argon atmosphere, a solution of 89 mg (0.39 mmol) of palladium(II) acetate and 160 mg (0.79 mmol) of tri-t-butylphosphine in xylene (140 mL) was agitated at room temperature for 30 minutes. 9.1 g (19.7 mmol) of the intermediate 2 and 5.58 g (19.7 mmol) of 1-(4-bromophenyl)naphthalene were added to the reaction liquid, which was agitated at 90° C., and then 2.27 g (23.7 mmol) of sodium t-butoxide was added, followed by agitating at 105° C. for 2.5 hours. After returning to room temperature, methanol was added to the reaction liquid, and the solid matter formed was collected by filtration. The resulting solid matter was purified by silica gel column chromatography and recrystallization to provide a white solid matter (9.3 g).

The analysis of the resulting solid matter by mass spectrum revealed that the solid matter was the target compound 1. The value m/e was 633 for the molecular weight of 633.26. The yield was 71%.

Synthesis Example 2 (Synthesis of Compound 2)

(1) Synthesis of Intermediate 3

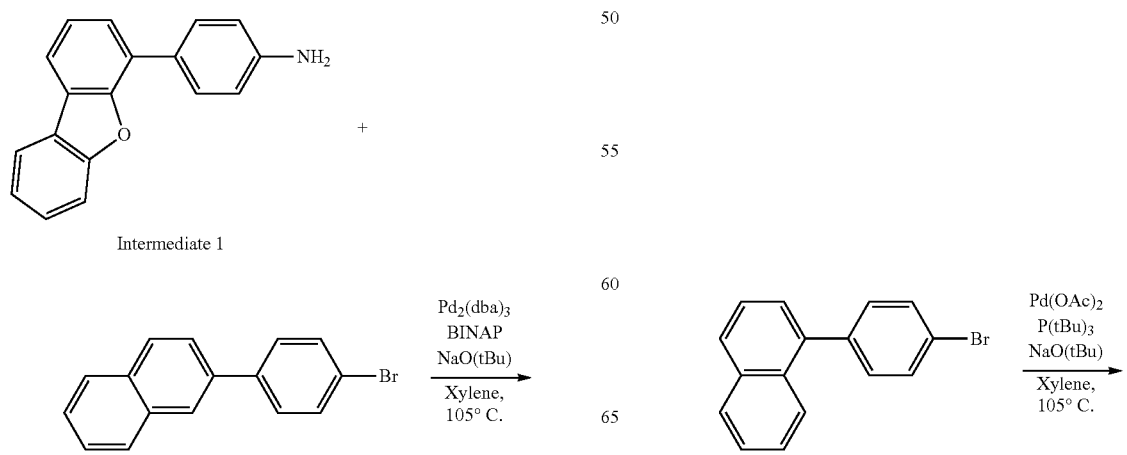

-continued

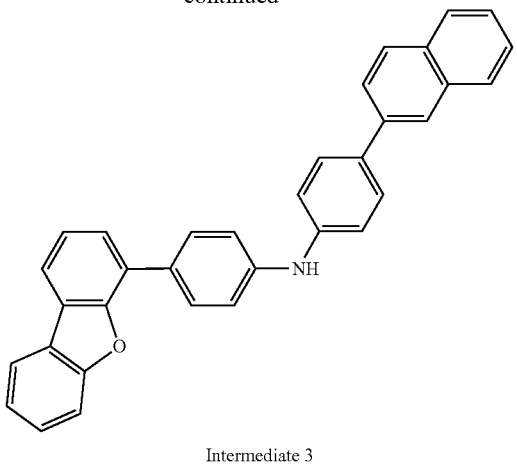

Intermediate 3

An intermediate 3 was obtained in the same procedures as in the synthesis of the intermediate 2 except that 2-(4-bromophenyl)naphthalene was used instead of 1-(4-bromophenyl)naphthalene in the synthesis of the intermediate 2.

(2) Synthesis of Compound 2

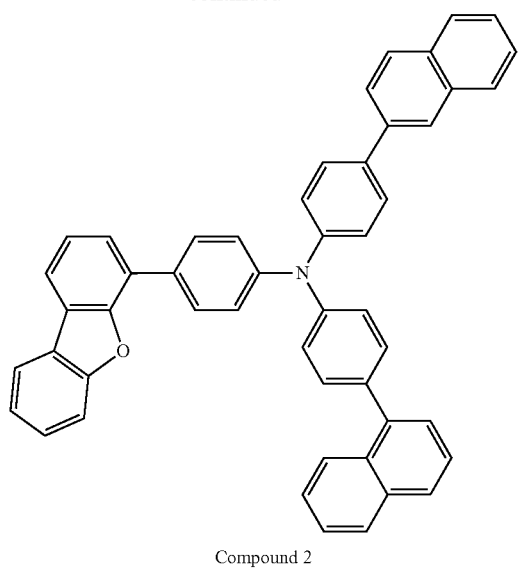

Compound 2

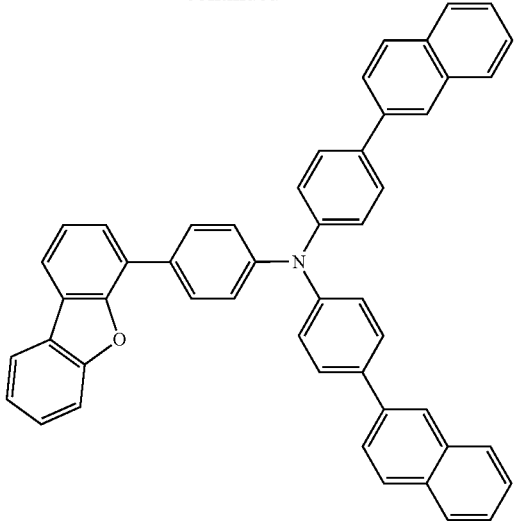

Compound 3

A white solid matter was obtained in the same procedures as in Synthesis Example 1 (3) except that the intermediate 3 was used instead of the intermediate 2 in Synthesis Example 1 (3).

The analysis of the resulting solid matter by mass spectrum revealed that the solid matter was the target compound 2. The value m/e was 633 for the molecular weight of 633.26. The yield was 68%.

A white solid matter was obtained in the same procedures as in Synthesis Example 1 (3) except that the intermediate 3 was used instead of the intermediate 2, and 2-(4-bromophenyl)naphthalene was used instead of 1-(4-bromophenyl)naphthalene, in Synthesis Example 1 (3).

The analysis of the resulting solid matter by mass spectrum revealed that the solid matter was the target compound 3. The value m/e was 633 for the molecular weight of 633.26. The yield was 70%.

Synthesis Example 3 (Synthesis of Compound 3)

Synthesis Example 4 (Synthesis of Compound 4)

(1) Synthesis of Intermediate 4

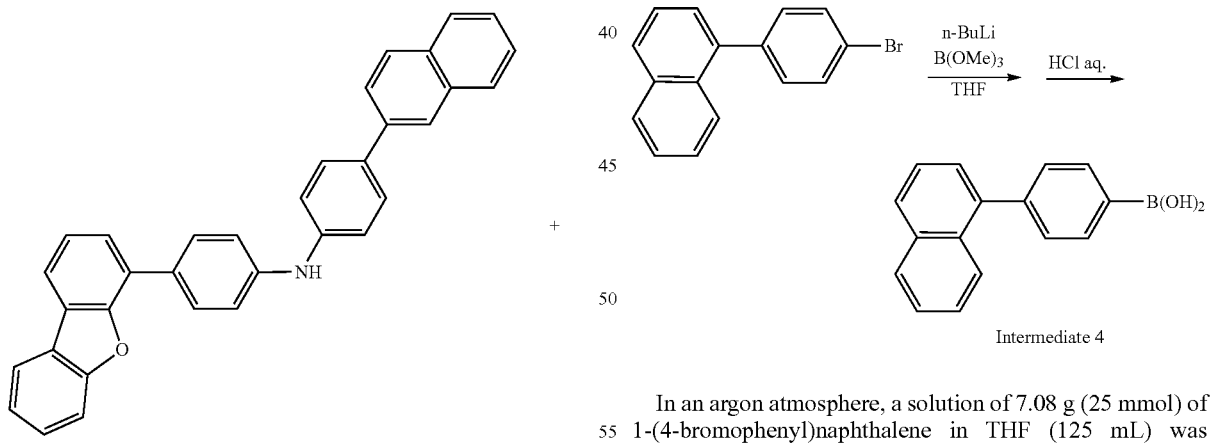

Intermediate 3

Intermediate 4

In an argon atmosphere, a solution of 7.08 g (25 mmol) of 1-(4-bromophenyl)naphthalene in THF (125 mL) was cooled over a dry ice/acetone bath, to which 17.2 mL (27.5 mmol) of a 1.6 M n-butyllithium hexane solution was added dropwise, and the mixture was agitated for 2 hours. A solution of 3.35 mL (30 mmol) of trimethyl borate in THF (10 mL) was added dropwise thereto, followed by agitating for 1 hour, and then the temperature thereof was increased to room temperature by detaching the dry ice/acetone bath. The reaction liquid was cooled over an ice bath, to which 2 M hydrochloric acid was added, and then the temperature thereof was increased to room temperature, followed by agitating for 1 hour. The resulting reaction liquid was extracted with ethyl acetate, and the organic layer was

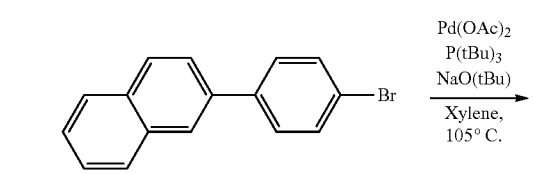

washed with water, then dried over anhydrous sodium sulfate, and concentrated under reduced pressure. The resulting residue was crystallized to provide 4.03 g of the intermediate 4. The yield was 65%.

(2) Synthesis of Intermediate 5

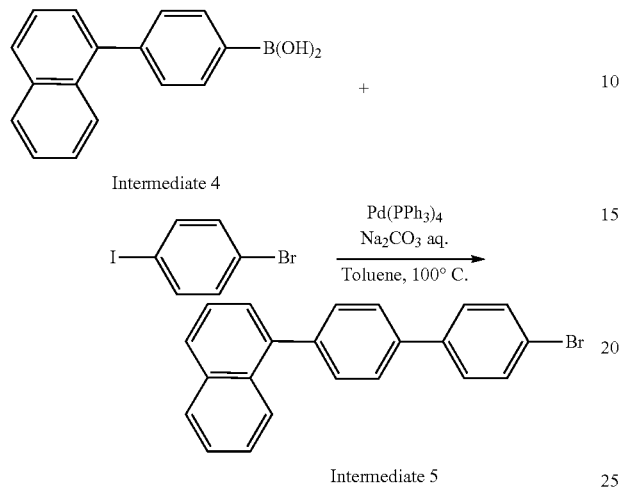

In an argon atmosphere, a mixture of 3.72 g (15 mmol) of the intermediate 4, 4.24 g (15 mmol) of 4-bromoiodobenzene, 347 mmol (0.30 mmol) of tetrakis(triphenylphosphine) palladium(0), 22.5 mL of a 2 M sodium carbonate aqueous solution, and 45 mL of toluene was agitated at 100° C. for 7 hours. After returning to room temperature, water was added thereto, the mixture was extracted with toluene, and the resulting toluene layer was dried over anhydrous sodium sulfate and concentrated under reduced pressure. The resulting residue was purified by silica gel column chromatography to provide 2.96 g of the intermediate 5. The yield was 55%.

(3) Synthesis of Compound 4

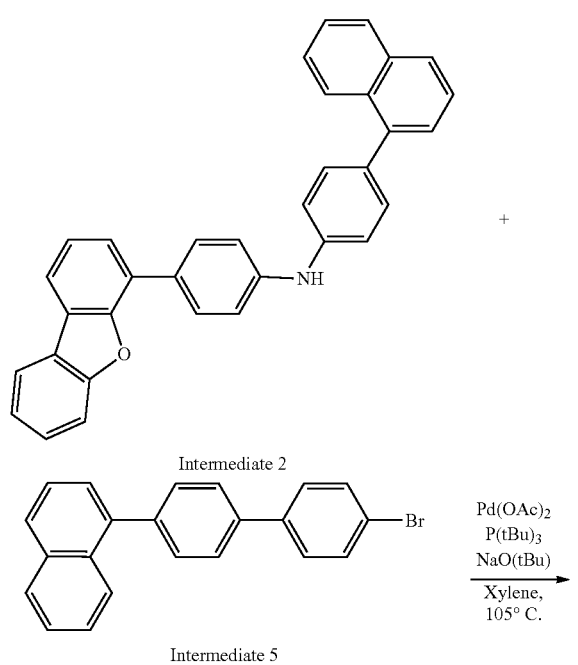

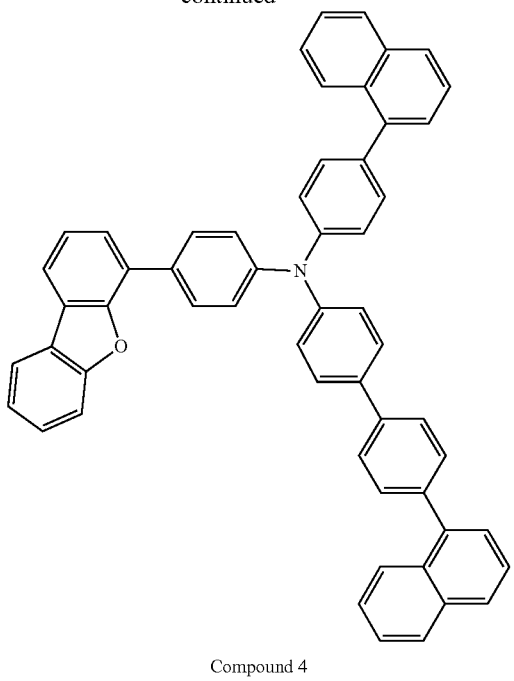

Compound 4

A white solid matter was obtained in the same procedures as in Synthesis Example 1 (3) except that the intermediate 5 was used instead of 1-(4-bromophenyl)naphthalene in Synthesis Example 1 (3).

The analysis of the resulting solid matter by mass spectrum revealed that the solid matter was the target compound 4. The value m/e was 739 for the molecular weight of 739.29. The yield was 62%.

Synthesis Example 5 (Synthesis of Compound 5)

(1) Synthesis of Intermediate 6

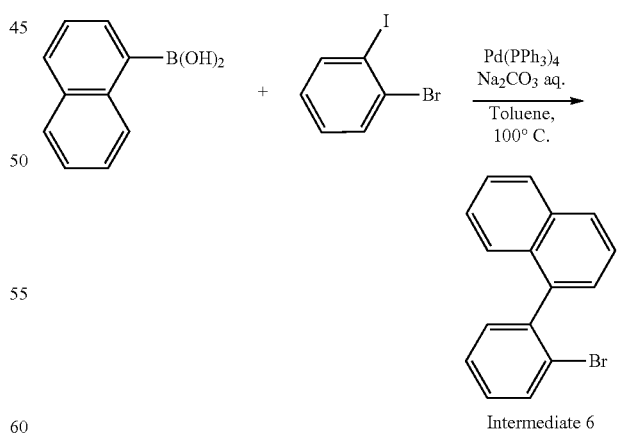

An intermediate 6 was obtained in the same procedures as in the synthesis of the intermediate 5 except that 1-naphthaleneboronic acid was used instead of the intermediate 4, and 2-bromoiodobenzene was used instead of 4-bromoiodobenzene, in the synthesis of the intermediate 5.

(2) Synthesis of Compound 5

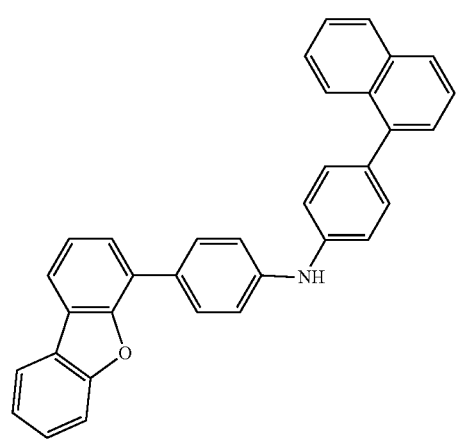

Intermediate 2

+

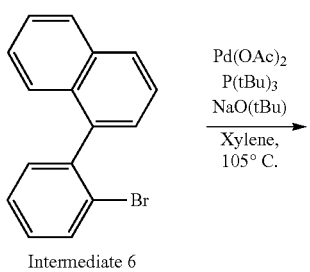

Intermediate 6

Pd(OAc)₂
P(tBu)₃
NaO(tBu)
───────→
Xylene,
105° C.

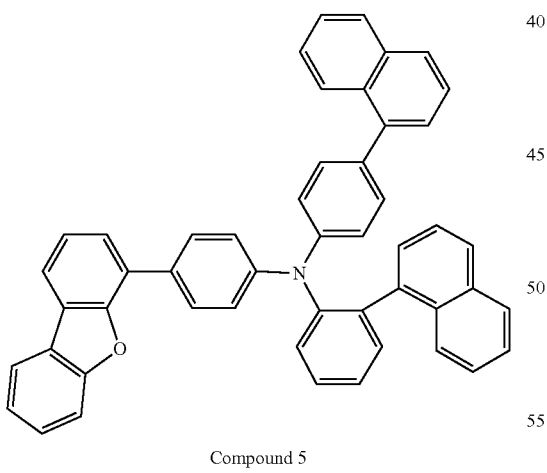

Compound 5

A white solid matter was obtained in the same procedures as in Synthesis Example 1 (3) except that the intermediate 6 was used instead of 1-(4-bromophenyl)naphthalene in Synthesis Example 1 (3).

The analysis of the resulting solid matter by mass spectrum revealed that the solid matter was the target compound 5. The value m/e was 633 for the molecular weight of 633.26. The yield was 58%.

Synthesis Example 6 (Synthesis of Compound 6)

(1) Synthesis of Intermediate 7

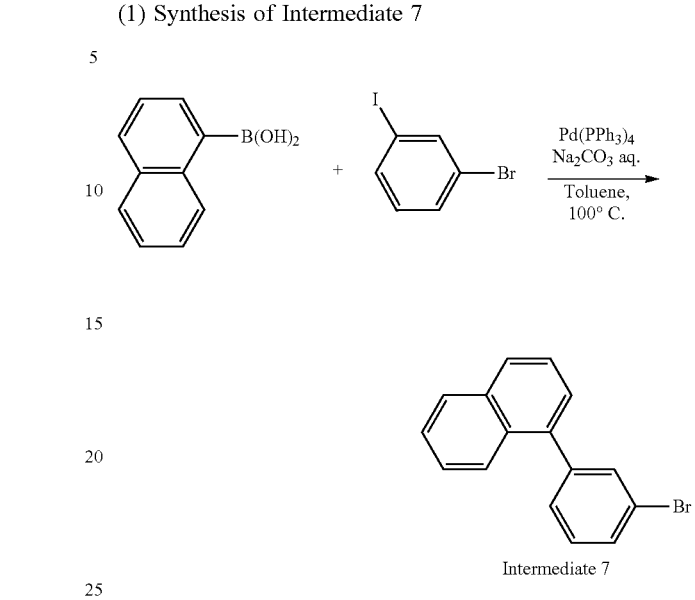

An intermediate 7 was obtained in the same procedures as in the synthesis of the intermediate 5 except that 1-naphthaleneboronic acid was used instead of the intermediate 4, and 3-bromoiodobenzene was used instead of 4-bromoiodobenzene, in the synthesis of the intermediate 5.

(2) Synthesis of Compound 6

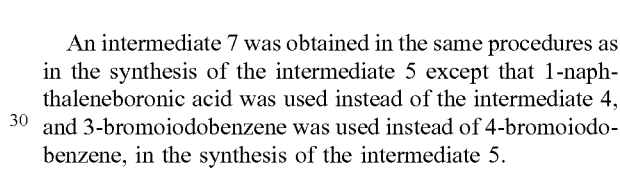

Intermediate 2

+

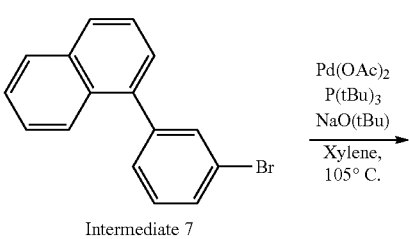

Intermediate 7

Pd(OAc)₂
P(tBu)₃
NaO(tBu)
───────→
Xylene,
105° C.

-continued

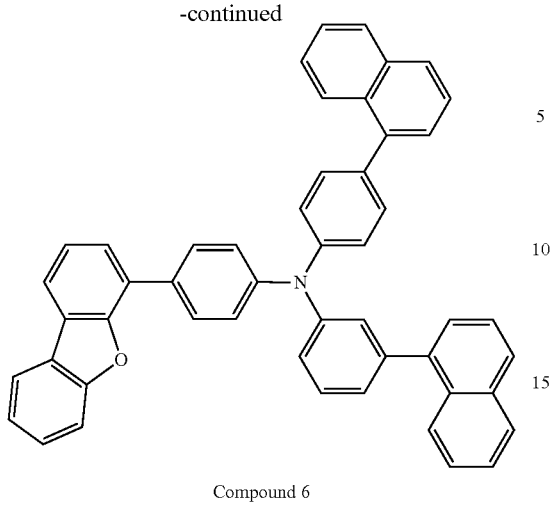

Compound 6

A white solid matter was obtained in the same procedures as in Synthesis Example 1 (3) except that the intermediate 7 was used instead of 1-(4-bromophenyl)naphthalene in Synthesis Example 1 (3).

The analysis of the resulting solid matter by mass spectrum revealed that the solid matter was the target compound 6. The value m/e was 633 for the molecular weight of 633.26. The yield was 66%.

<Production of Organic EL Device>

An organic EL device was produced in the following manner.

EXAMPLE 1

A glass substrate having a dimension of 25 mm×75 mm×1.1 mm in thickness having an ITO transparent electrode (anode) (produced by Geomatec Co., Ltd.) was subjected to ultrasonic cleaning in isopropyl alcohol for 5 minutes, and then subjected to UV ozone cleaning for 30 minutes. The thickness of ITO was 130 nm.

The cleaned glass substrate was mounted on a substrate holder of a vacuum vapor deposition device, and HI-1 was vapor-deposited on the surface thereof on the side having transparent electrode lines formed thereon to cover the transparent electrode, so as to form a hole injection layer having a thickness of 5 nm.

On the hole injection layer, HT-1 was vapor-deposited to form a first hole transporting layer having a thickness of 80 nm. On the first hole transporting layer, the compound 1 obtained in Synthesis Example 1 was vapor-deposited to form a second hole transporting layer having a thickness of 10 nm. Subsequently, on the second hole transporting layer, BH-1 (host material) and BD-1 (dopant material) were vapor-co-deposited to form a light emitting layer having a thickness of 25 nm. The concentration of BD-1 (dopant material) in the light emitting layer was 4% by mass.

Subsequently, on the light emitting layer, ET-1 was vapor-deposited to form a first electron transporting layer having a thickness of 10 nm. Subsequently, on the first electron transporting layer, ET-2 was vapor-deposited to form a second electron transporting layer having a thickness of 15 nm.

Furthermore, on the second electron transporting layer, lithium fluoride (LiF) was vapor-deposited to form an electron injecting electrode having a thickness of 1 nm.

Finally, on the electron injecting electrode, metallic aluminum (Al) was vapor-deposited to form a metallic cathode having a thickness of 80 nm.

The organic EL device of Example 1 had the following structure.

ITO (130)/HI-1 (5)/HT-1 (80)/Compound 1 (10)/BH-1/BD-1 (25/4% by mass)/ET-1 (10)/ET-2 (15)/LiF (1)/Al (80)

The numerals in parentheses show the thicknesses (unit: nm).

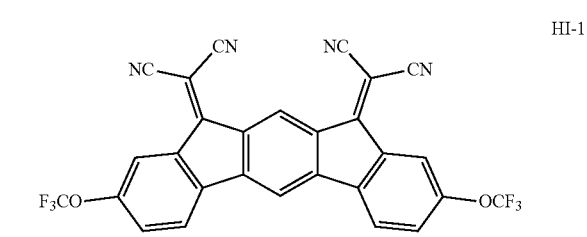

HI-1

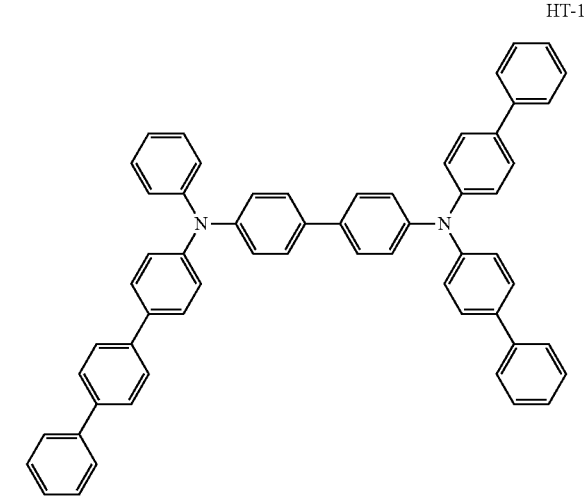

HT-1

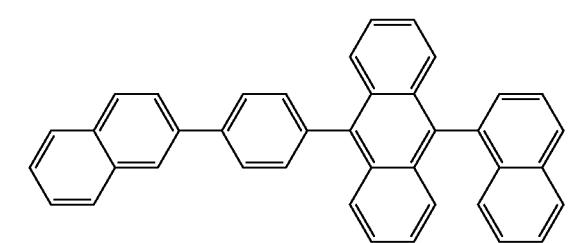

BH-1

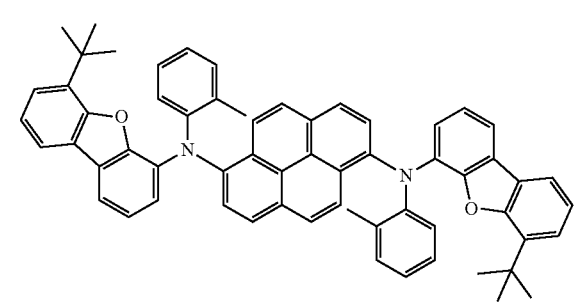

BD-1

-continued

ET-1

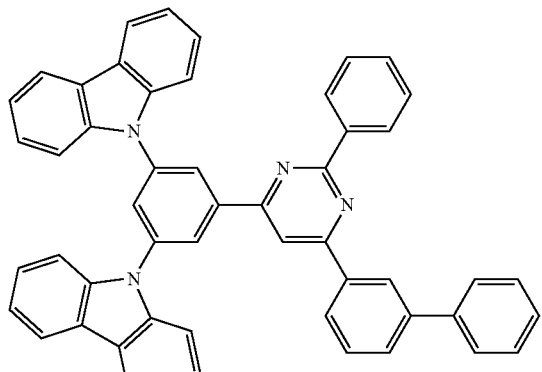

ET-2

EXAMPLE 2

An organic EL device was produced in the same manner as in Example 1 except that the compound 2 obtained in Synthesis Example 2 was used instead of the compound 1 used in the second hole transporting layer of Example 1.

EXAMPLE 3

An organic EL device was produced in the same manner as in Example 1 except that the compound 3 obtained in Synthesis Example 3 was used instead of the compound 1 used in the second hole transporting layer of Example 1.

EXAMPLE 4

An organic EL device was produced in the same manner as in Example 1 except that the compound 4 obtained in Synthesis Example 4 was used instead of the compound 1 used in the second hole transporting layer of Example 1.

EXAMPLE 5

An organic EL device was produced in the same manner as in Example 1 except that the compound 5 obtained in Synthesis Example 5 was used instead of the compound 1 used in the second hole transporting layer of Example 1.

EXAMPLE 6

An organic EL device was produced in the same manner as in Example 1 except that the compound 6 obtained in Synthesis Example 6 was used instead of the compound 1 used in the second hole transporting layer of Example 1.

Comparative Example 1

An organic EL device was produced in the same manner as in Example 1 except that the following comparative compound 1 was used instead of the compound 1 used in the second hole transporting layer of Example 1.

Comparative Example 2

An organic EL device was produced in the same manner as in Example 1 except that the following comparative compound 2 was used instead of the compound 1 used in the second hole transporting layer of Example 1.

Comparative Example 3

An organic EL device was produced in the same manner as in Example 1 except that the following comparative compound 3 was used instead of the compound 1 used in the second hole transporting layer of Example 1.

Comparative Example 4

An organic EL device was produced in the same manner as in Example 1 except that the following comparative compound 4 was used instead of the compound 1 used in the second hole transporting layer of Example 1.

Comparative Example 5

An organic EL device was produced in the same manner as in Example 1 except that the following comparative compound 5 was used instead of the compound 1 used in the second hole transporting layer of Example 1.

Comparative Example 6

An organic EL device was produced in the same manner as in Example 1 except that the following comparative compound 6 was used instead of the compound 1 used in the second hole transporting layer of Example 1.

Comparative Example 7

An organic EL device was produced in the same manner as in Example 1 except that the following comparative compound 7 was used instead of the compound 1 used in the second hole transporting layer of Example 1.

Comparative Example 8

An organic EL device was produced in the same manner as in Example 1 except that the following comparative compound 8 was used instead of the compound 1 used in the second hole transporting layer of Example 1.

Comparative Example 9

An organic EL device was produced in the same manner as in Example 1 except that the following comparative compound 9 was used instead of the compound 1 used in the second hole transporting layer of Example 1.

Comparative Compound 1
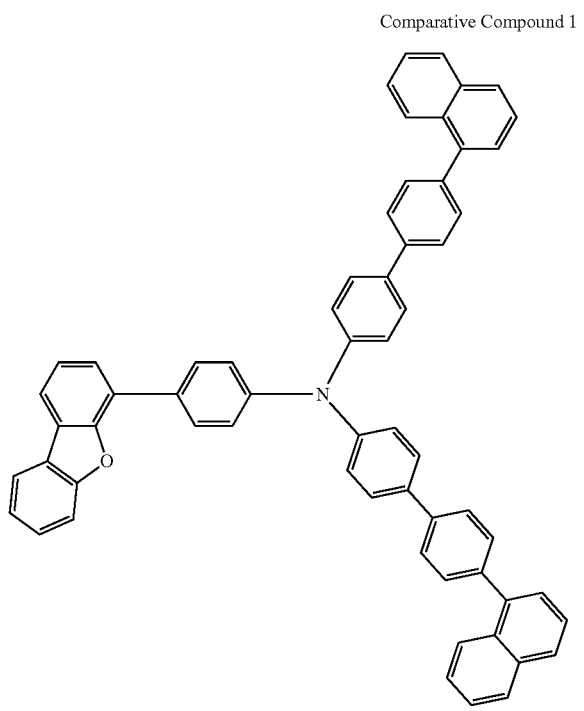
Comparative Compound 2
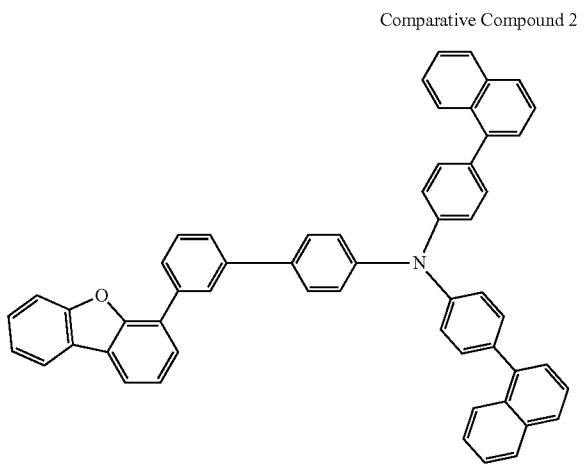
Comparative Compound 3
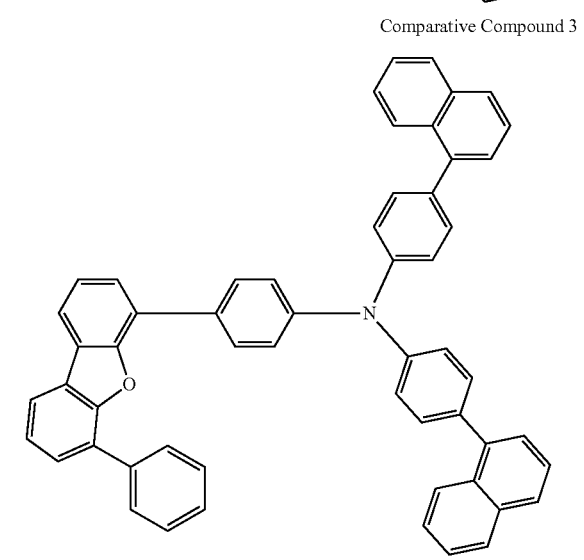
Comparative Compound 4
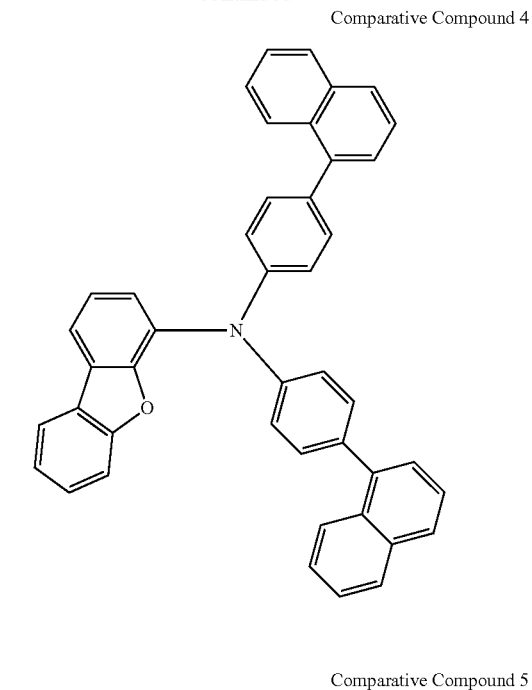
Comparative Compound 5
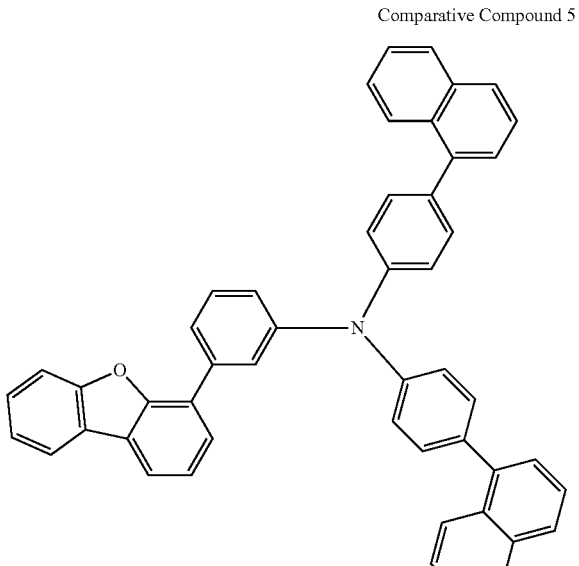
Comparative Compound 6
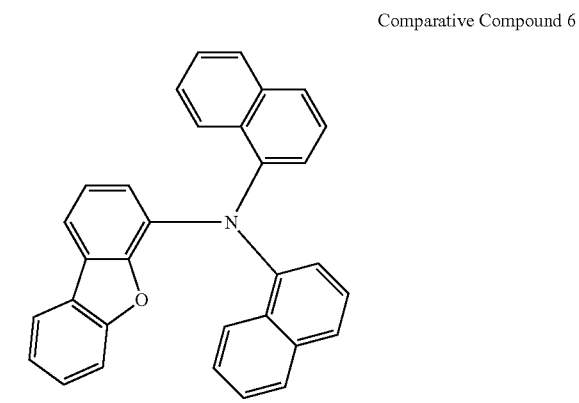

-continued

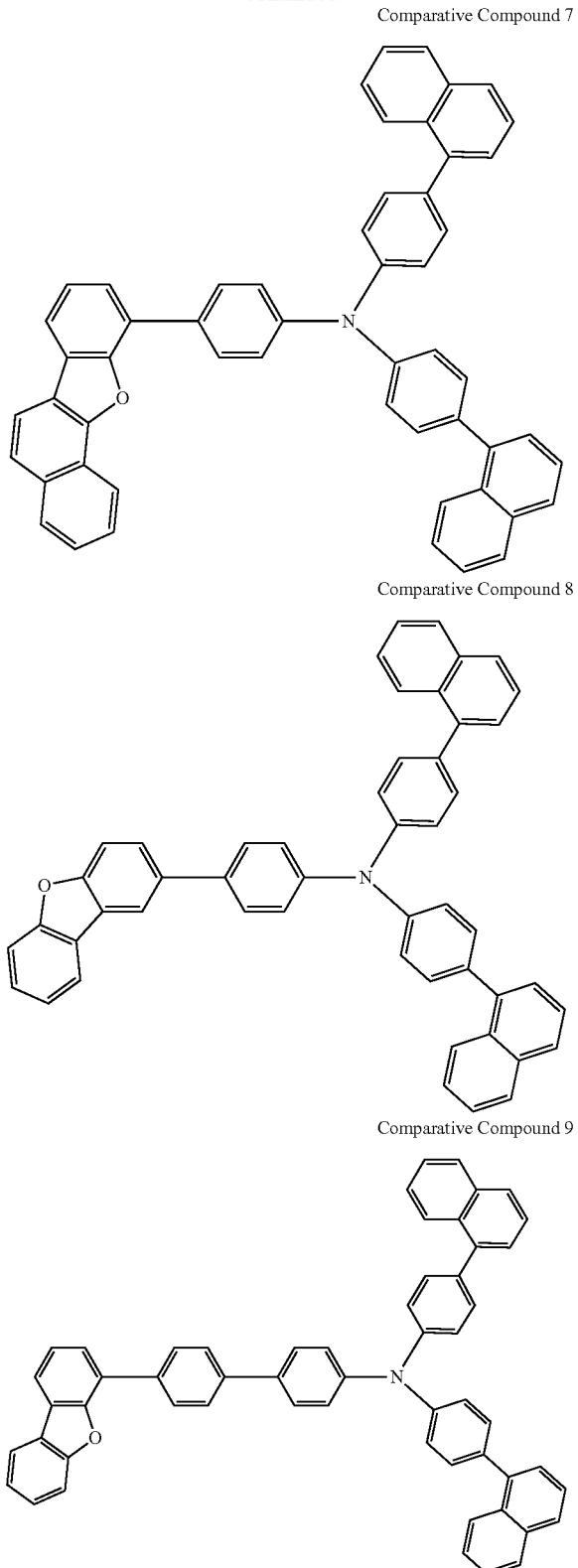

Comparative Compound 7

Comparative Compound 8

Comparative Compound 9

<Evaluation of Organic EL Device 1>

For each of the organic EL device produced, a voltage was applied to the organic EL device to make a current density of 10 mA/cm², and the external quantum efficiency was evaluated. A voltage was applied to the organic EL device to make a current density of 50 mA/cm², and the 90% lifetime (LT90) was evaluated. The results are shown in Table 1. The 90% lifetime (LT90) herein means the period of time (hr) until the luminance is decreased to 90% in constant current driving.

TABLE 1

|  | Hole transporting material | External quantum efficiency (%) | 90% Lifetime (hr) |
| --- | --- | --- | --- |
| Example 1 | Compound 1 | 9.5 | 170 |
| Example 2 | Compound 2 | 9.4 | 160 |
| Example 3 | Compound 3 | 9.4 | 150 |
| Example 4 | Compound 4 | 9.2 | 170 |
| Example 5 | Compound 5 | 9.6 | 130 |
| Example 6 | Compound 6 | 9.5 | 140 |
| Comparative Example 1 | Comparative Compound 1 | 8.6 | 130 |
| Comparative Example 2 | Comparative Compound 2 | 9.2 | 80 |
| Comparative Example 3 | Comparative Compound 3 | 8.7 | 130 |
| Comparative Example 4 | Comparative Compound 4 | 9.0 | 70 |
| Comparative Example 5 | Comparative Compound 5 | 9.0 | 80 |
| Comparative Example 6 | Comparative Compound 6 | 8.8 | 75 |
| Comparative Example 7 | Comparative Compound 7 | 8.4 | 90 |
| Comparative Example 8 | Comparative Compound 8 | 9.3 | 50 |
| Comparative Example 9 | Comparative Compound 9 | 8.5 | 130 |

Synthesis Example 7 (Synthesis of Compound 7)

(1) Synthesis of Intermediate 8

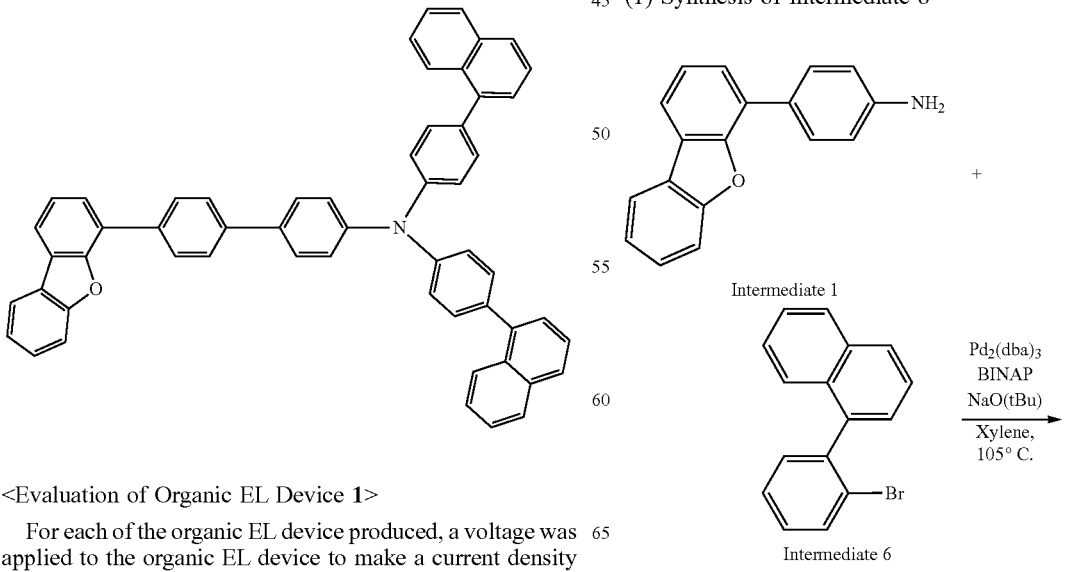

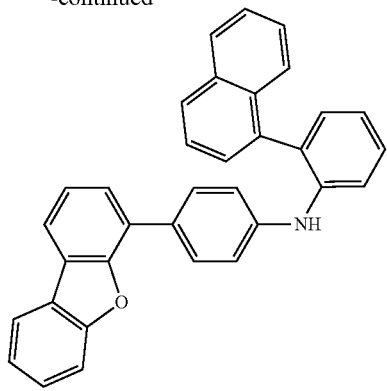

Intermediate 8

An intermediate 8 was obtained in the same procedures as in the synthesis of the intermediate 2 except that the intermediate 6 was used instead of 1-(4-bromophenyl)naphthalene in the synthesis of the intermediate 2.

(2) Synthesis of Compound 7

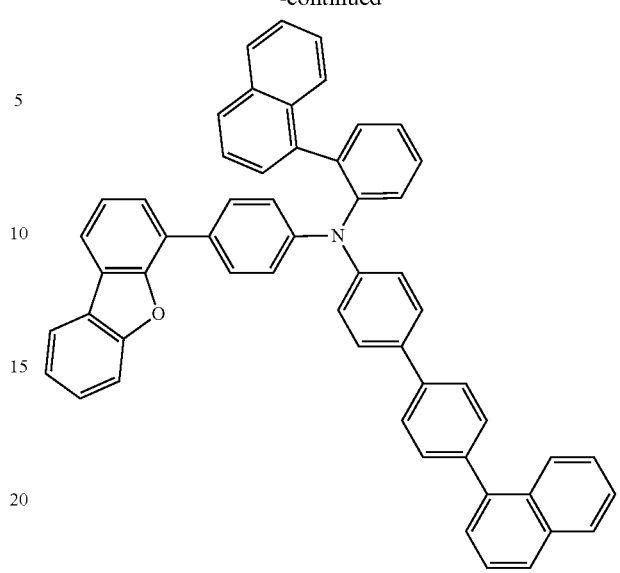

Compound 7

A white solid matter was obtained in the same procedures as in Synthesis Example 1 (3) except that the intermediate 8 was used instead of the intermediate 2, and the intermediate 5 was used instead of 1-(4-bromophenyl)naphthalene, in Synthesis Example 1 (3).

The analysis of the resulting solid matter by mass spectrum revealed that the solid matter was the target compound 7. The value m/e was 739 for the molecular weight of 739.29. The yield was 55%.

Synthesis Example 8 (Synthesis of Compound 8)

(1) Synthesis of Intermediate 9

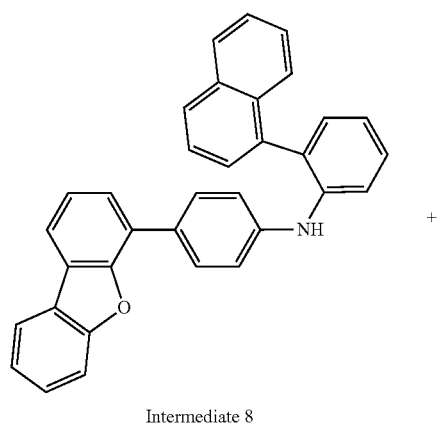

Intermediate 8

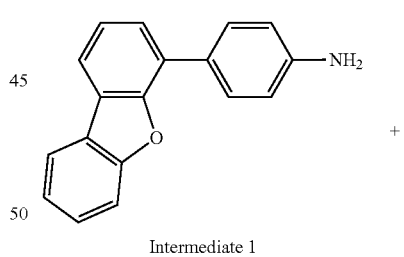

Intermediate 1

+

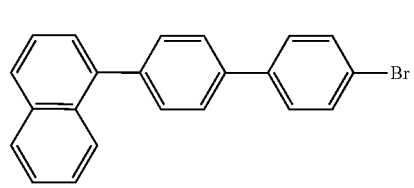

Intermediate 5

Pd(OAc)₂
P(tBu)₃
NaO(tBu)
Xylene,
105° C.

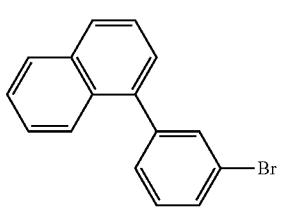

Intermediate 7

Pd₂(dba)₃
BINAP
NaO(tBu)
Xylene,
105° C.

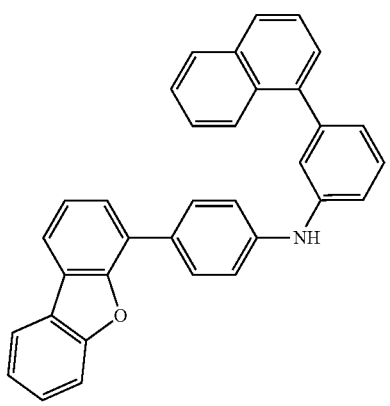

Intermediate 9

An intermediate 9 was obtained in the same procedures as in the synthesis of the intermediate 2 except that the intermediate 7 was used instead of 1-(4-bromophenyl)naphthalene in the synthesis of the intermediate 2.

(2) Synthesis of Compound 8

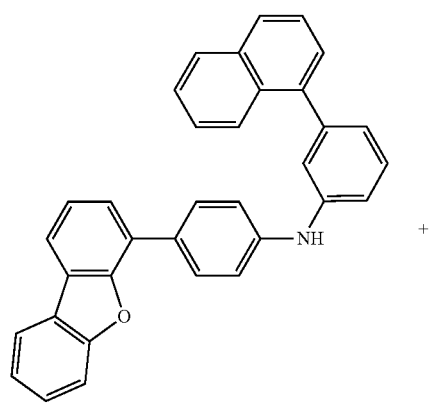

Intermediate 9

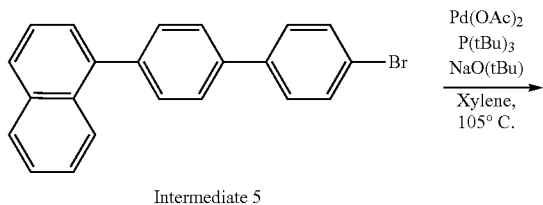

Intermediate 5

Compound 8

A white solid matter was obtained in the same procedures as in Synthesis Example 1 (3) except that the intermediate 9 was used instead of the intermediate 2, and the intermediate 5 was used instead of 1-(4-bromophenyl)naphthalene, in Synthesis Example 1 (3).

The analysis of the resulting solid matter by mass spectrum revealed that the solid matter was the target compound 8. The value m/e was 739 for the molecular weight of 739.29. The yield was 60%.

EXAMPLE 7

An organic EL device was produced in the same manner as in Example 1 except that the compound 7 obtained in Synthesis Example 7 was used instead of the compound 1 used in the second hole transporting layer of Example 1.

EXAMPLE 8

An organic EL device was produced in the same manner as in Example 1 except that the compound 8 obtained in Synthesis Example 8 was used instead of the compound 1 used in the second hole transporting layer of Example 1.

<Evaluation of Organic EL Device 2>

The organic EL devices produced were evaluated for the external quantum efficiency and the 90% lifetime (LT90) in the same manner as in Examples 1 to 6. The results are shown in Table 2.

TABLE 2

|  | Hole transporting material | External quantum efficiency (%) | 90% Lifetime (hr) |
| --- | --- | --- | --- |
| Example 7 | Compound 7 | 9.5 | 150 |
| Example 8 | Compound 8 | 9.4 | 140 |

As apparent from Tables 1 and 2, it is found that the use of the compounds 1 to 8 encompassed in the compound (1) having the particular structure, as a hole transporting material of an organic EL device can provide an organic EL device that simultaneously satisfies a high external quantum efficiency and a long lifetime, which cannot be achieved by the comparative compounds 1 to 9.

It is considered that the material of the present invention retains a large singlet energy gap in such a manner that: plural side chains each having a ring structure having three or more rings connected as in the comparative compound 1 are not included; an aryl substituent or ring condensation introduced to the dibenzofuran moiety having the largest spread of the conjugated system as in the comparative compounds 3 and 7 is not included; and a linker including two benzene rings connected to the nitrogen atom as in the comparative compound 9 is not included, but the number of the benzene ring is limited to one as in the compounds 1 to 8. According to the structure, it is considered that excitons are confined in the light emitting layer, and the energy is converted to light with less loss, achieving a high efficiency. In the case where the site having a relatively high electron accepting capability of a naphthalene ring or a dibenzofuran ring is connected directly to the nitrogen atom as in the comparative compounds 4 and 6, it is considered that electrons accepted by the material strongly act on the center nitrogen atom to make the material unstable, and therefore it is considered that the structure of the present invention achieves a long lifetime by connecting these rings to the amine atom through the linker. Furthermore, it is considered that the bent linker for dibenzofuran having the largest electron accepting capability as in the comparative compounds 2 and 5 makes the molecule unstable in accepting electrons, and therefore it is considered that the material of the present invention having the p-phenylene linker achieves a long lifetime. Moreover, it is considered that the dibenzofuran ring connected to the center nitrogen atom by extension from the 2-position thereof as in the comparative compound 8 is not included, but the dibenzofuran ring is connected to the center nitrogen atom by extension from the 4-position thereof as in the compounds 1 to 8, so as to stabilize the structure, achieving a longer lifetime than the ordinary 2-substituted compound.

REFERENCE SIGN LIST

1 Organic electroluminescence device
2 Substrate
3 Anode
4 Cathode
5 Light emitting layer
6 Hole injection layer/hole transporting layer
7 Electron injection layer/electron transporting layer
10 Light emitting unit

The invention claimed is:

1. A compound represented by the following formula

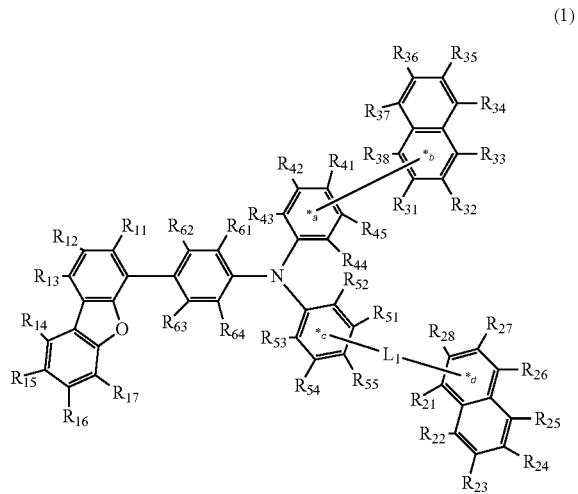

(1)

wherein in the formula (1), $R_{11}$ to $R_{17}$ and $R_{61}$ to $R_{64}$ each independently represent a hydrogen atom, or an unsubstituted alkyl group having 1 to 20 carbon atoms, one of $R_{41}$, $R_{43}$, and $R_{44}$ represents a single bond bonded to *a, the others of $R_{41}$, $R_{43}$, and $R_{44}$ than the single bond bonded to *a each independently represent a hydrogen atom, or an unsubstituted alkyl group having 1 to 20 carbon atoms, and R and $R_{45}$ each represent a hydrogen atom, one of $R_{52}$, $R_{53}$, and $R_{55}$ represents a single bond bonded to *c, and the others of $R_{52}$, $R_{53}$, and $R_{55}$ than the single bond bonded to *c each independently represent a hydrogen atom, or an unsubstituted alkyl group having 1 to 20 carbon atoms, and $R_{51}$ and $R_{54}$ each represent a hydrogen atom, one of $R_{21}$ to $R_{28}$ represents a single bond bonded to *d, and the others of $R_{21}$ to $R_{28}$ than the single bond bonded to *d each independently represent a hydrogen atom, an unsubstituted alkyl group having 1 to 20 carbon atoms, or an unsubstituted aryl group having 6 to 50 ring carbon atoms, one of $R_{31}$ to $R_{38}$ represents a single bond bonded to *b, and the others of $R_{31}$ to $R_{38}$ than the single bond bonded to *b each independently represent a hydrogen atom, an unsubstituted alkyl group having 1 to 20 carbon atoms, or an unsubstituted aryl group having 6 to 50 ring carbon atoms, and $L_1$ represents a single bond, an unsubstituted phenylene group, or an unsubstituted biphenylene group, provided that in $R_{11}$ to $R_{17}$, $R_{21}$ to $R_{28}$, $R_{31}$ to $R_{38}$, $R_{41}$ to $R_{45}$, $R_{51}$ to $R_{55}$, and $R_{61}$ to substituents adjacent to each other are not bonded to each other and do not form a ring.

2. The compound according to claim 1, wherein the compound represented by the formula (1) is represented by the following formula (2-1) or (2-2):
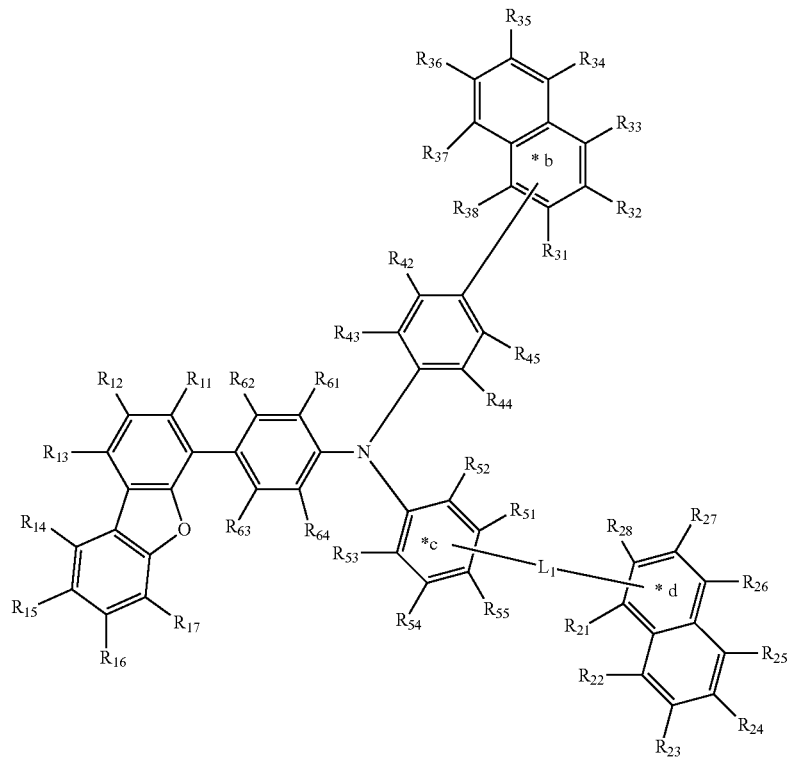
(2-1)
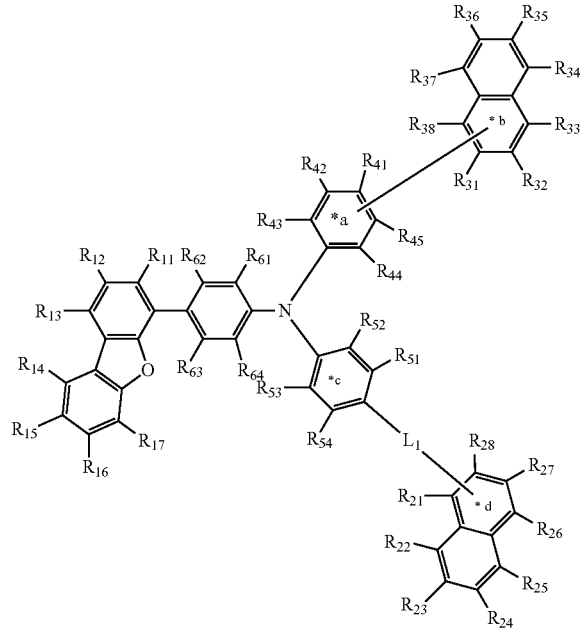
(2-2)
wherein in the formulae (2-1) and (2-2),
$R_{11}$ to $R_{17}$, $R_{21}$ to $R_{28}$, $R_{31}$ to $R_{38}$, $R_{41}$ to $R_{45}$, $R_{51}$ to $R_{55}$, $R_{61}$ to $R_{64}$, and $L_1$ are the same as above.

3. The compound according to claim 1, wherein the compound represented by the formula (I) is represented by the following formula (3-1):

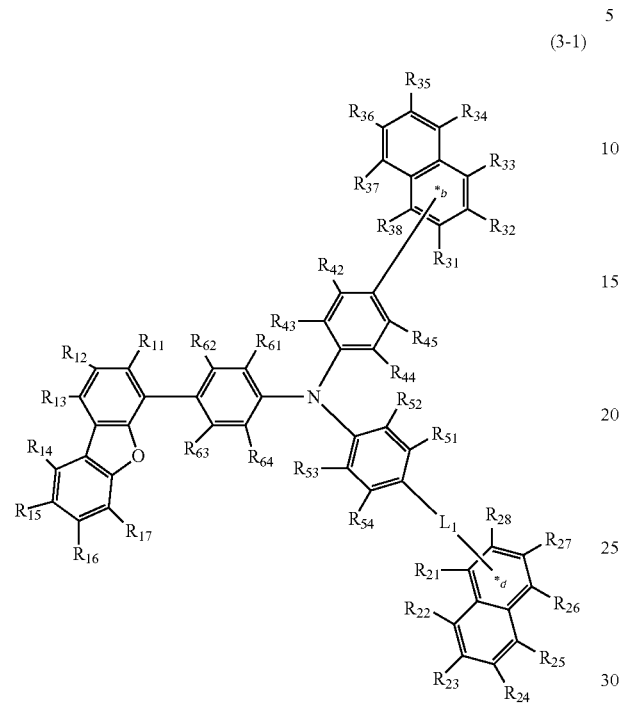

(3-1)

wherein in the formula (3-1),
$R_{11}$ to $R_{17}$, $R_{21}$ to $R_{28}$, $R_{31}$ to $R_{38}$, $R_{42}$ to $R_{45}$, $R_{51}$ to $R_{54}$, $R_{61}$ to $R_{64}$, and $L_1$ are the same as above.

4. The compound according to claim 1, wherein $L_1$ represents an unsubstituted phenylene group.

5. The compound according to claim 1, wherein $L_1$ represents a single bond or an unsubstituted phenylene group.

6. The compound according to claim 1, wherein $L_1$ represents a single bond.

7. The compound according to claim 1, wherein
$R_{11}$ to $R_{17}$ and $R_{61}$ to $R_{64}$ each independently represents a hydrogen atom or an unsubstituted alkyl group having 1 to 5 carbon atoms,
$R_{41}$, $R_{43}$, and $R_{44}$ other than the single bond bonded to *a, and $R_{52}$, $R_{53}$, and $R_{55}$ other than the single bond bonded to *c, each independently represents a hydrogen atom or an unsubstituted alkyl group having 1 to 5 carbon atoms, and
$R_{21}$ to $R_{28}$ other than the single bond bonded to *d and $R_{31}$ to $R_{38}$ other than the single bond bonded to *b each independently represent a hydrogen atom or an unsubstituted alkyl group having 1 to 5 carbon atoms.

8. The compound according to claim 1, wherein $R_{11}$ to $R_{17}$ represent hydrogen atoms.

9. The compound according to claim 1, wherein $R_{41}$ to $R_{45}$ other than the single bond bonded to *a, $R_{51}$ to $R_{55}$ other than the single bond bonded to *c, and $R_{61}$ to $R_{64}$ represent hydrogen atoms.

10. The compound according to claim 1, wherein $R_{21}$ to $R_{28}$ other than the single bond bonded to *d and $R_{31}$ to $R_{38}$ other than the single bond bonded to *b are hydrogen atoms.

11. The compound according to claim 1, wherein the compound is selected from the group consisting of the following compounds 1 to 5:

Compound 1

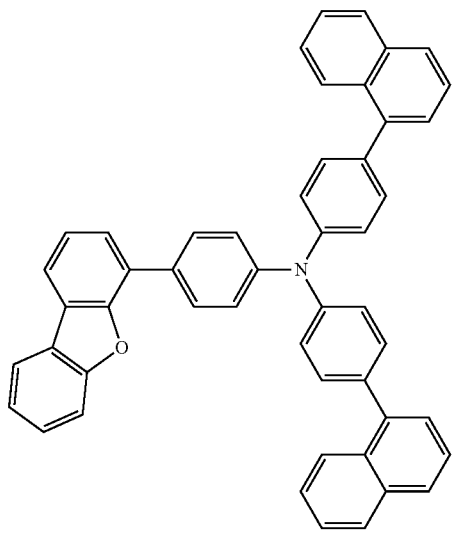

Compound 2

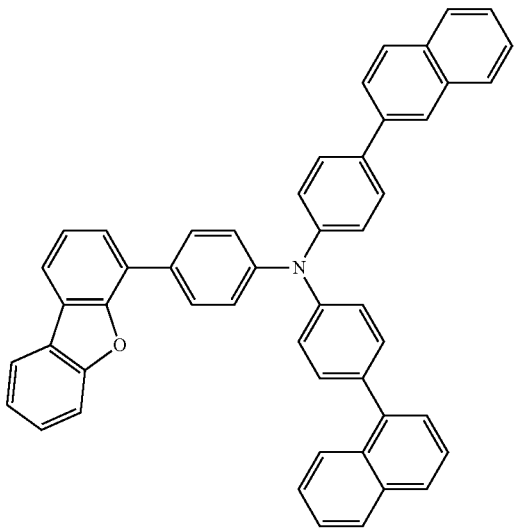

Compound 3

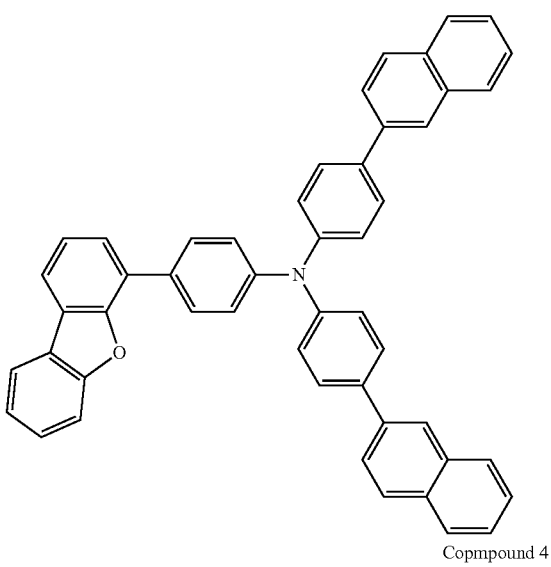

Compound 4

Compound 5

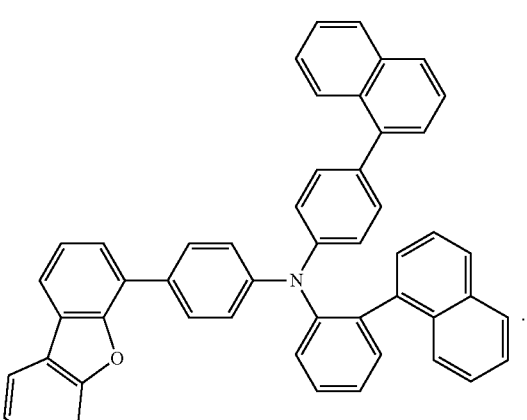

12. A material for an organic EL device, comprising the compound according to claim 1.

13. An organic electroluminescence device comprising an anode, a cathode, and an organic layer between the anode and the cathode, the organic layer including a light emitting layer, at least one layer of the organic layer including the compound according to claim 1.

14. The organic electroluminescence device according to claim 13, wherein an organic layer is between the anode and the light emitting layer, and the organic layer includes the compound.

15. The organic electroluminescence device according to claim 13, wherein the organic layer includes the light emitting layer and a hole transporting layer, the hole transporting layer is between the anode and the light emitting layer, and the hole transporting layer includes the compound.

16. The organic electroluminescence device according to claim 15, wherein the hole transporting layer includes a first hole transporting layer and a second hole transporting layer, and the second hole transporting layer includes the compound.

17. An electronic equipment comprising the organic electroluminescence device according to claim 13.

* * * * *